United States Patent [19]

Kump et al.

[11] Patent Number: 5,180,718
[45] Date of Patent: Jan. 19, 1993

[54] ACYL DERIVATIVES OF OXAZOLORIFAMYCINS

[75] Inventors: Wilhelm Kump, Biel-Benken; Christian Borel, Geneva, both of Switzerland; Jen Chen, Sunnyvale, Calif.; Siem J. Veenstra, Basel, Switzerland; John Francis; Benjamin B. Mugrage, both of Basking Ridge, N.J.

[73] Assignee: Ciba-Geigy Corporation, Ardsley, N.Y.

[21] Appl. No.: 718,894

[22] Filed: Jun. 21, 1991

Related U.S. Application Data

[63] Continuation-in-part of Ser. No. 576,631, Aug. 31, 1990, abandoned, which is a continuation-in-part of Ser. No. 485,345, Feb. 23, 1990, abandoned, which is a continuation-in-part of Ser. No. 454,325, Dec. 21, 1989, abandoned.

[30] Foreign Application Priority Data

Mar. 2, 1989 [CH] Switzerland .................... 776/898
Dec. 12, 1990 [EP] European Pat. Off. ........ 90810980.4

[51] Int. Cl.$^5$ ................. C07D 498/18; A61K 31/495
[52] U.S. Cl. ................................... 514/183; 540/457; 540/458; 540/459; 540/468
[58] Field of Search ............... 514/183; 540/457, 458, 540/459, 468

[56] References Cited

U.S. PATENT DOCUMENTS

| 4,005,077 | 1/1977 | Bickel et al. | 540/268 |
| 4,585,589 | 4/1986 | Malabarba et al. | 514/483 |
| 4,876,258 | 10/1989 | Kump et al. | 514/524 |
| 4,916,126 | 4/1990 | Traxler et al. | 514/183 |
| 4,918,066 | 4/1990 | Kump | 514/183 |
| 5,003,070 | 3/1991 | Kump et al. | 544/368 |
| 5,053,510 | 10/1991 | Kump | 544/368 |
| 5,100,894 | 3/1992 | Taylor et al. | 514/253 |

FOREIGN PATENT DOCUMENTS

| 314041 | 5/1989 | European Pat. Off. |  |
| 314624 | 5/1989 | European Pat. Off. | 514/183 |
| 350445 | 1/1990 | European Pat. Off. |  |
| 385405 | 9/1990 | European Pat. Off. |  |
| 395580 | 10/1990 | European Pat. Off. |  |
| 434621 | 6/1991 | European Pat. Off. |  |
| 9003608 | 2/1991 | South Africa. |  |

OTHER PUBLICATIONS

Chem. Abstract 87, 193990a (1977).
Chem. Abstract 75, 3809e (1977).
Traxler et al. J. Med. Chem. 33, 552 (1990).
Taguchi et al. Chem. Pharm. Bull. vol. 33 No. 5 pp. 2133-2136 (1985).
Kump et al. Chem. Abstr. vol. 111 (19) entry 173911m (1989) abstracting EP 314,624.

*Primary Examiner*—Donald G. Daus
*Attorney, Agent, or Firm*—Norbert Gruenfeld

[57] ABSTRACT

The invention relates to novel acyl derivatives of rifamycins of the formula and the salts thereof, in which the structural elements $-A_1-A_2-$, $-A_3-A_4-$ and $-A_5-A_6-$ each denote ethylene or vinylene or the elements $-A_1-A_2-$ and $-A_3-A_4-$ each denote ethylene and $-A_5-A_6-$ denotes vinylene; X represents $>C(R_6)-$ or $>N-$ and $R_6$ denotes hydrogen or alkyl; alk denotes an aliphatic hydrocarbon radical; $R_1$ denotes hydrogen or acyl; $R_2$ denotes acyl, or alkyl which is optionally substituted by an aromatic radical, and $R_3$ and $R_3'$ represent a common bond, or $R_3$ denotes hydrogen or acyl, and $R_3'$ is hydrogen; $R_4$ denotes hydrogen, cycloalkyl or aryl; $R_5$ denotes hydrogen or acetyl; $R_7$ denotes hydrogen or alkyl, which can be used as active compounds in medicaments, the preparation and use thereof, and pharmaceutical products and the preparation thereof.

33 Claims, No Drawings

ACYL DERIVATIVES OF OXAZOLORIFAMYCINS

CROSS REFERENCE TO RELATED APPLICATIONS

This is a continuation-in-part of application Ser. No. 576,631 filed Aug. 31, 1990, now abandoned, which is a continuation-in-part application of Ser. No. 485,345, filed Feb. 23, 1990, now abandoned, which is a continuation-in-part application of Ser. No. 454,325, filed Dec. 21, 1989, now abandoned.

SUMMARY

The invention relates to novel acyl derivatives of rifamycins of the formula

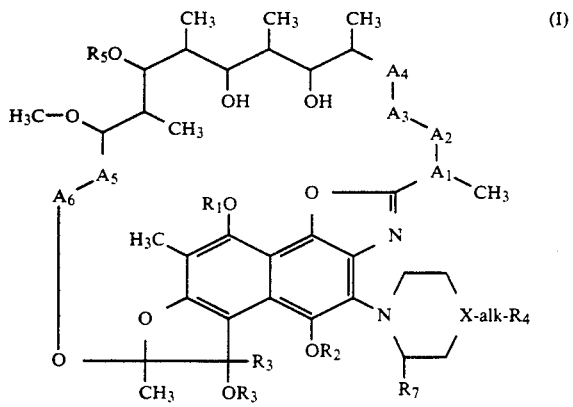

and the salts thereof, in which the structural elements $-A_1-A_2-$, $-A_3-A_4-$ and $-A_5-A_6-$ each denote ethylene or vinylene, or the elements $-A_1-A_2-$ and $-A_3-A_4-$ each denote ethylene and $-A_5-A_6-$ denotes vinylene; X represents $>C(R_6)-$ or $>N-$ and $R_6$ denotes hydrogen or alkyl; alk denotes an aliphatic hydrocarbon radical; $R_1$ denotes hydrogen or acyl; $R_2$ denotes acyl, or alkyl which is optionally substituted by an aromatic radical, and $R_3$ and $R_3'$ repesent a common bond, or $R_3$ denotes hydrogen or acyl, and $R_3'$ is hydrogen; $R_4$ denotes hydrogen, cycloalkyl or aryl; $R_5$ denotes hydrogen or acetyl; $R_7$ denotes hydrogen or alkyl; the preparation and use thereof, and pharmaceutical products and the preparation thereof.

The ring system numbering used as a basis essentially corresponds to that employed, for example, in U.S. Pat. No. 4,005,077. The compounds of the formula I have several centres of chirality, and accordingly the present invention embraces the corresponding optical isomers, for example diastereoisomers.

A particular embodiment of the invention relates to derivatives of rifamycin SV of formula Ia

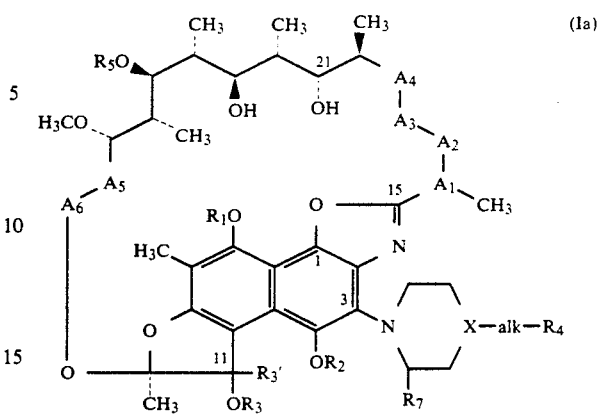

wherein symbols have meaning as defined for formula I above. The configurations at most C-atoms correspond to the known configurations of rifamycin S and rifamycin SV [cf. S. J. Danishefsky et al., J. Am. Chem. Soc. 109 (1987) 862–867]. If $-A_1-A_2-$ represents ethylene there is a further asymmetric centre at C-16. The methyl group bonded to C-16 is preferably in the α-position, i.e. below the plane of the paper like e.g. the 21-hydroxy group. If $R_3$ denotes hydrogen or acyl and $R'_3$ is hydrogen, there is an additional asymmetric centre at C-11. In this case $R'_3$ may be in α- or β-position, but is preferably in α-position ($OR_3$ being β).

DETAILED DESCRIPTION OF THE INVENTION

The compounds of the formula I or Ia can be in the form of salts, especially pharmaceutically utilizable (acceptable) salts. Because the compounds according to the invention have at least one basic centre, they are therefore able to form acid addition salts. The latter are formed, for example, with inorganic acids such as mineral acids, for example sulfuric acid, a phosphorus or hydrohalic acid, or with organic carboxylic acids such as optionally substituted, for example by halogen, $C_1$-$C_4$alkanecarboxylic acids, for example acetic acid, such as optionally unsaturated dicarboxylic acids, for example oxalic, malonic succinic, maleic, fumaric, phthalic or terephthalic acid, such as hydroxy carboxylic acids, for example ascorbic, glycolic, lactic, mallic, tartaric or citric acid, such as amino acids, for example aspartic or glutamic acid, with a benzoic acid or with organic sulfonic acids such as optionally substituted, for example by halogen, $C_1$-$C_4$alkane- or arylsulfonic acids, for example methane-, bromobenzene- or p-toluenesulfonic acid. Appropriate acid addition salts can also be formed with an additional basic centre which is present where appropriate (for example $X=>N-$). Furthermore, the compounds according to the invention which have an acidic phenolic hydroxyl group can form salts ($R_1=H$) with bases, for example alkali metals, such as sodium or potassium salts. In addition, corresponding inner salts can be formed. Also embraced are salts unsuitable for pharmaceutical uses, because the latter can be employed, for example, for the isolation or purification of compounds according to the invention or the pharmaceutically utilizable salts thereof.

The general definitions used hereinbefore and hereinafter have primarily the following meanings, unless defined differently:

An aliphatic hydrocarbon radical denotes, in particular, alkylene, alkenylene and alkynylene, where the multiple bond is located in a position higher than α to the piperazine nitrogen atom (X= >N—).

Acyl is derived, for example, from an organic carboxylic acid, a substituted carbonic acid or an organic sulfonic acid. Examples of such radicals are alkanoyl, halogenoalkanoyl, arylalkanoyl, N,N-dialkylaminoalkanoyl, alkoxyalkanoyl, carbocyclic or heterocyclic aroyl, alkoxycarbonyl, arylalkoxycarbonyl, amino-carbonyl which is optionally mono- or disubstituted by alkyl, or alkanesulfonyl, halogenoalkanesulfonyl, arylalkanesulfonyl, cycloalkanesulfonyl or arylsulfonyl. In this connection, aryl denotes in each case, in particular, phenyl or naphthyl and carbocyclic aroyl, in particular benzoyl or naphthoyl and heterocyclic aroyl, in particular 5- or 6-membered monocyclic monoaza-, monooxa- or monothiaaroyl, such as pyrroloyl, pyridoyl, furoyl or thenoyl, where such aryl or aroyl radicals are unsubstituted or substituted one or more times, for example two or three times, for example by substituents selected from the group consisting of halogen, alkyl, alkoxy, hydroxyl, alkanoyloxy, trifluoromethyl and nitro. Acyl also includes (pyrrolidino-, piperidino-, homopiperidino-, morpholino-, thiomorpholino-) carbonyl, furthermore adamantylcarbonyl, biphenylcarbonyl and bicycloheptylcarbonyl. An aromatic radical is, in particular, phenyl, furthermore naphthyl, which are unsubstituted or substituted one or more times, for example as indicated hereinafter for aryl. A corresponding alkyl substituted by an aromatic radical denotes, for example, phenyl- or naphthyl-($C_1$–$C_7$-)alkyl such as benzyl or 1- or 2-phenylethyl.

Aryl $R_4$ is derived, for example, from a mono- or polycyclic, such as bicyclic, C ring system which has at least one aromatic ring, such as phenyl, biphenylyl such as 2-, 3- or, in particular 4-biphenylyl, or naphthyl such as 1- or 2-naphthyl, and is unsubstituted or substituted, for example one or more times, such as two or three times, for example by substituents selected from the group consisting of halogen, ($C_1$–$C_7$-)alkyl, ($C_1$–$C_7$-)alkoxy, hydroxyl, ($C_2$–$C_8$-)alkanoyloxy, trifluoromethyl and nitro.

Alkyl denotes, in particular, lower alkyl, e.g. $C_1$–$C_7$alkyl and is, for example, methyl, ethyl, propyl, isopropyl, n-butyl, isobutyl, sec-butyl, tert-butyl and furthermore embraces appropriate pentyl, hexyl and heptyl radicals. $C_1$–$C_4$Alkyl is preferred.

Cycloalkyl denotes, in particular, $C_3$–$C_7$cycloalkyl and denotes, for example, cyclopropyl, -butyl, -pentyl, -hexyl or -heptyl. Cyclopentyl and cyclohexyl is preferred. Cycloalkyl may in turn be substituted by lower alkyl.

Alkylene denotes, in particular, $C_1$–$C_7$alkylene and is straight-chain or branched and denotes, for example, methylene, ethylene, propylene and butylene as well as 1,2-propylene, 2-methyl-1,3-propylene or 2,2-dimethyl-1,3-propylene. $C_1$–$C_5$Alkylene is preferred.

Alkenylene denotes, in particular, $C_3$–$C_7$alkenylene and is straight-chain or branched and denotes, for example, 1,3-prop-2-enylene, 1,4-but-2-, 1,4-but-3-enylene, 1,3-but-2-enylene, 2,4-but-3-enylene, 1,5-pent-2-, -3-, -4-enylene, furthermore appropriate hexenylene and heptenylene radicals. $C_3$–$C_5$Alkenylene is preferred.

Alkynylene denotes, in particular, $C_3$–$C_7$alkynylene and is straight-chain or branched and denotes, for example, 1,3-prop-2-ynylene, 1,4-but-2-, 1,4-but-3-ynylene, 1,5-pent-2-, -3- and -5-ynylene, furthermore appropriate hexynylene and heptynylene radicals. $C_3$–$C_5$Alkynylene is preferred.

Alkanoyl denotes, in particular, $C_2$–$C_8$alkanoyl and is, for example, acetyl, propionyl, butyryl, isobutyryl or pivaloyl. Preferred, especially for $R_1$, is branched $C_2$–$C_6$alkanoyl, primarily pivaloyl, whereas $R_2$ and $R_3$ in particular are represented by $C_2$–$C_6$alkanoyl, primarily acetyl or propionyl.

Halogen is, in particular, halogen with atomic number up to and including 35, such as fluorine, chlorine and bromine, furthermore iodine.

Alkoxy denotes, in particular, $C_1$–$C_7$alkoxy and is, for example, methoxy, ethoxy, propyloxy, isopropyloxy, n-butyloxy, isobutyloxy and tert-butyloxy. $C_1$–$C_4$Alkoxy is preferred.

Alkoxyalkanoyl, especially for $R_1$, is preferably 2-alkoxy-$C_2$–$C_8$-alkanoyl, for example 2-alkoxy-2,2-dimethylacetyl such as 2-methoxy-2,2-dimethylacetyl.

Dialkylaminoalkanoyl, especially for $R_1$, is preferably 2-dimethylamino-$C_2$–$C_8$-alkanoyl, for example 2-N,N-dimethylamino-2,2-dimethylacetyl.

Alkoxycarbonyl is, in particular, $C_2$–$C_8$-alkoxycarbonyl and is, for example, methoxy-, ethoxy-, propyloxy- or pivaloyloxy-carbonyl. $C_2$–$C_5$Alkoxycarbonyl is preferred.

Alkanesulphonyl is, in particular, $C_1$–$C_7$alkanesulfinyl or -sulfonyl and is, for example, methane-, ethane-, n-propane- or isopropane-sulfinyl or -sulfonyl. $C_1$–$C_4$Alkanesulfinyl or -sulfonyl is preferred.

Halogenalkanesulphonyl is, in particular, halo-$C_1$–$C_7$alkanesulphonyl, in particular halo-$C_1$–$C_4$alkylsulphonyl, and is, for example, trifluoromethane-, difluoromethane- or 1,1,2-trifluoroethanesulphonoyl.

Naphthyl is 1- or 2-naphthyl.

Pyrroloyl is, for example, 2- or 3-pyrroloyl. Furoyl is 2- or 3-furoyl and thenoyl is 2- or 3-thenoyl, while suitable pyridoyl is 2-, 3- and 4-pyridoyl.

Alkanoyloxy is, in particular, $C_2$–$C_8$alkanoyloxy, in particular, $C_2$–$C_5$alkanoyloxy, such as acetyloxy, propionyloxy or pivaloyloxy.

It is known of derivatives which are derived, for example, from rifamycin SV that they have pronounced antibiotic properties and can be employed, for example, for the treatment of tuberculosis. All the more important is the experimentally verified finding that the compounds of the formula I and Ia and the pharmaceutically utilizable salts thereof show no corresponding antibiotic activity in the customary pharmacological test models.

On the other hand, surprisingly they have a significant lipid-lowering action which can be detected in animal experiments, preferably on mammals, for example rats. Thus, the lowering of very low density, low density and high density lipoproteins (VLDL, LDL and HDL respectively) in the serum can be shown in two designs of test, namely in genetically hypercholesterolaemic male rats (design A) and normolipaemic rats of both sexes (design B).

Albino rats (Sprague-Dawley derivatives of the strain Tif:RAI) with a body weight of 180–240 g, which have free access to standard rat feed and drinking water, are used. The test compound is administered in a supplemented maize starch solution (3% aqueous maize starch with 0.33% Tween 80 and 5% polyethylene glycol solution with a mean molecular weight of 400) orally to groups of 6 rats each day for 5 consecutive days. The animals are sacrificed two hours after the last dose. The animals receive no more food for 16 hours before their death. The blood is collected in a 0.05% strength aqueous ethylenediaminetetraacetic acid solution. After centrifugation until the blood cells have sedimented, the content of cholesterol and triglycerides is analysed enzymatically using, for example, the test systems supplied by Sigma Chemical Co. (St. Louis, Mo. U.S.A.). For the HDL-cholesterol determination, a solution of heparin and manganese chloride (final concentration = 1.3 g/l or 46 mMol) is added to 0.5 ml of EDTA-plasma. The precipitate which forms is sedimented by centrifugation, and the cholesterol concentration in the supernatant is analysed enzymatically as for the total cholesterol. The difference between the latter value and the cholesterol value determined directly on an aliquot of the complete serum is, according to Warnick, G. R. et al., J. Lipid Res. 19; 65–76 (1978), equivalent to the VLDL- and LDL-cholesterol.

The testing for an antibiotic reaction is carried out, for example, on the one hand in vitro by determining the mean effective concentration $EC_{50}$ for the inhibition of RNA polymerase of Escherichia coli, and the minimum inhibitory concentration (MIC) in a conventional plate test, and on the other hand in vivo on infected mice and rats by determining the $ED_{50}$ (effective dose which keeps 50% of the experimental animals alive). The microorganisms used for the present purpose are, in particular, Mycobacterium tuberculosis TB $H_{37}Rv$ and Staphylococcus aureus. In the case of compounds with a lipid-lowering indication, an antibiotic activity is regarded as disadvantageous because it may lead, especially on long-term administration, to the development of strains of microorganisms resistant to antibiotics.

In the test methods described above, the compounds according to the invention display a significant hypolipidaemic activity on repeated administration in the dose range from about 0.1 to about 50 mg/kg/day; by contrast, they have negligible antibiotic activity in the abovementioned tests.

Thus, for example, it is possible to show, depending on the experimental designs, that the minimum effective dose of the compounds according to the invention is about 0.1 to about 10 mg/kg on single administration, and a 50–70% lowering of total cholesterol can be achieved by repeated administration of 30 mg/kg a day. Moreover, the compounds have virtually no antibiotic activity; an $EC_{50}$ for inhibition of RNA polymerase is not yet reached at 100 μg/ml, and the MIC for various pathogenic strains of Staphylococcus aureus is above 130 μg/ml. Such values are about 1000 times higher than concentrations normally necessary for a corresponding effect. Also in vivo, using mice infected with Staphylococcus aureus, the compound proves to have no antibiotic activity at a single dose of 200 mg/kg.

Thanks to their LDL-lowering action, the compounds according to the invention can be used, for example, as hypolipidaemics for the treatment of hyperlipidaemias, principally of types IIa and IIb, and arteriosclerosis, for example when hyperlipoproteinaemia is present as risk factor.

Accordingly, the compounds of the formula I and the pharmaceutically utilizable salts thereof can be used, for example, as pharmaceuticals, for example as hypolipidaemics for the treatment of hyperlipidaemias, principally of types IIa and IIb, and of arteriosclerosis when hyperlipoproteinaemia is present as risk factor. The invention furthermore relates to the use of the compounds according to the invention for the preparation of medicaments, in particular of hypolipidaemics and antiarteriosclerotics, and for therapeutic and prophylactic treatment. Also included therein is the industrial preparation of the active substances.

In opposite to prior art compounds corresponding to formula I in which $R_3$ and $R_3'$ together represent a double bond, those compounds of the present invention in which $R_3$ and $R_3'$ are different from representing a double bond are surprisingly essentially colorless. Furthermore, compounds of the formula I in which $R_2$ is different from hydrogen are considered as more stable than those prior art compounds corresponding to formula I in which $R_2$ represents hydrogen. The compounds of the present invention can additionally be used as starting material.

The invention in particular relates to compounds of the formula I and Ia and salts thereof, in which the structural elements $—A_1—A_2—$, $—A_3—A_4—$ and $—A_5—A_6—$ each denote ethylene or vinylene or the elements $—A_1—A_2—$ and $—A_3—A_4—$ each denote ethylene and $—A_5—A_6—$ denotes vinylene; X represents $>C(R_6)—$ or $>N—$ and $R_6$ is hydrogen; alk denotes an aliphatic hydrocarbon radical; $R_1$ denotes hydrogen or acyl; $R_2$ and $R_3$, independently of one another, denote acyl; $R_3'$ denotes hydrogen; $R_4$ denotes hydrogen, cycloalkyl or aryl; $R_5$ denotes hydrogen or acetyl; $R_7$ denotes hydrogen.

The invention particularly relates to compounds of the formula I and Ia and salts thereof, in which $—A_1—A_2—$, $—A_3—A_4—$, $—A_5—A_6—$ and $R_5$ have the indicated meanings; X represents $>C(R_6)—$ or $>N—$, and $R_6$ denotes hydrogen or $C_1$-$C_7$alkyl; alk denotes $C_1$-$C_7$alkylene, $C_3$-$C_7$alkenylene or $C_3$-$C_7$alkynylene; $R_1$ denotes $C_2$-$C_8$alkanoyl, halogen-$C_2$-$C_8$alkanoyl, alkoxy-$C_2$-$C_8$-alkanoyl, phenyl- or naphthyl-$C_2$-$C_8$alkanoyl, benzoyl, naphthoyl, 5- or 6-membered monocyclic monoaza-, monooxa- or monothiaaroyl, $C_1$-$C_7$alkoxycarbonyl, phenyl- or naphthyl-$C_1$-$C_7$alkoxy-carbonyl, aminocarbonyl which is unsubstituted or mono- or di-substituted by $C_1$-$C_7$alkyl, or $C_1$-$C_7$alkanesulfonyl, halogeno-$C_1$-$C_7$alkanesulfonyl, phenyl- or naphthyl-$C_1$-$C_7$alkanesulfonyl, $C_3$-$C_7$cycloalkanesulfonyl or benzene- or naphthylsulfonyl; $R_2$ denotes $C_2$-$C_8$alkanoyl, halogeno-$C_2$-$C_8$alkanoyl, phenyl- or naphthyl-$C_2$-$C_8$alkanoyl, benzoyl, naphthoyl, 5- or 6-membered monocyclic monoaza-, monooxa- or monothiaaroyl, $C_1$-$C_7$alkoxycarbonyl, phenyl-or naphthyl-$C_1$-$C_7$alkoxy-carbonyl, aminocarbonyl which is unsubstituted or mono- or disubstituted by $C_1$-$C_7$alkyl, or $C_1$-$C_7$alkanesulfonyl, halogeno-$C_1$-$C_7$alkanesulfonyl, phenyl- or naphthyl-$C_1$-$C_7$alkanesulfonyl, $C_3$-$C_7$cycloalkanesulfonyl or benzene- or naphthylsulfonyl, $C_1$-$C_7$alkyl, phenyl- or naphthyl-$C_1$-$C_7$alkyl, $R_3$ and $R_3'$ represent a common bond, or $R_3$ denotes hydrogen or $C_2$-$C_8$alkanoyl, halogeno-$C_2$-$C_8$alkanoyl, phenyl- or naphthyl-$C_2$-$C_8$alkanoyl, benzoyl, naphthoyl, 5- or 6-membered monocyclic monoaza-, monooxa- or monothiaaroyl, $C_1$-$C_7$alkoxycarbonyl, phenyl- or naphthyl-$C_1$-$C_7$alkoxy-carbonyl, aminocarbonyl which is unsubstituted or mono- or di-substituted by $C_1$-$C_7$alkyl, or $C_1$-$C_7$alkanesulfonyl, halogeno-$C_1$-$C_7$alkanesulfonyl, phenyl- or naphthyl-$C_1$-$C_7$alkanesulfonyl, $C_3$-$C_7$cycloalkylsulfonyl or benzene- or naphthylsulfonyl, and $R_3'$ is hydrogen; $R_4$ denotes hydrogen, $C_3$-$C_7$cycloalkyl, phenyl, biphenylyl or naphthyl; $R_7$ denotes hydrogen or $C_1$-$C_7$alkyl; where the aromatic radicals in each case are unsubstituted or substituted one or more times by substituents selected from the group consisting of halogen, $C_1$-$C_7$alkyl, $C_1$-$C_7$alkoxy, hydroxyl, $C_2$-$C_8$alkanoyloxy, trifluoromethyl and nitro.

The invention particularly relates to compounds of the formula I and Ia and salts thereof, in which $-A_1-A_2-$, $-A_3-A_4-$, $-A_5-A_6-$ and $R_5$ have the indicated meanings; X represents $>C(R_6)-$ or $>N-$, and $R_6$ is hydrogen; alk denotes $C_1-C_7$alkylene, $C_3-C_7$alkenylene or $C_3-C_7$alkynylene; $R_1$, $R_2$ and $R_3$, independently of one another, denote $C_2-C_8$alkanoyl, halogeno-$C_2-C_8$alkanoyl, phenyl- or naphthyl-$C_2-C_8$alkanoyl, benzoyl, naphthoyl, 5- or 6-membered monocyclic monoaza-, monooxa- or monothiaaroyl, $C_1-C_7$alkoxycarbonyl, phenyl- or naphthyl-$C_1-C_7$alkoxy-carbonyl, aminocarbonyl which is unsubstituted or mono- or di-substituted by $C_1-C_7$alkyl, or $C_1-C_7$alkanesulfonyl, halogeno-$C_1-C_7$alkanesulfonyl, phenyl- or naphthyl-$C_1-C_7$alkanesulfonyl, $C_3-C_7$cycloalkanesulfonyl or benzene- or naphthylsulfonyl, and $R_1$ additionally and $R_3'$ and $R_7$ denote hydrogen; $R_4$ denotes hydrogen, $C_3-C_7$cycloalkyl, phenyl, biphenylyl or naphthyl; where the aromatic radicals are in each case unsubstituted or substituted one or more times by substituents selected from the group consisting of halogen, $C_1-C_7$alkyl, $C_1-C_7$alkoxy, hydroxyl, $C_2-C_8$alkanoyloxy, trifluoromethyl and nitro.

The invention particularly relates to compounds of the formula I and Ia and salts thereof, in which $-A_1-A_2-$, $-A_3-A_4-$, $-A_5-A_6-$ and $R_5$ have the indicated meanings; X represents $>C(R_6)-$ or $>N-$, and $R_6$ is hydrogen; alk denotes $C_1-C_7$alkylene, $C_3-C_7$alkenylene or $C_3-C_7$alkynylene, in particular $C_1-C_4$alkylene, $C_3-C_4$alkenylene or $C_3-C_4$alkynylene, where the multiple bonds are located in a position higher than $\alpha$ to the piperazine nitrogen; $R_1$ denote $C_2-C_8$alkanoyl, in particular $C_2-C_6$alkanoyl, phenyl-$C_2-C_6$alkanoyl, benzoyl, $C_1-C_7$alkoxy-carbonyl such as $C_1-C_4$alkoxycarbonyl, phenyl-$C_1-C_4$alkoxycarbonyl, $C_1-C_4$alkanesulfonyl or benzenesulfonyl; $R_2$ denotes $C_2-C_8$alkanoyl, in particular $C_2-C_6$alkanoyl, phenyl-$C_2-C_6$alkanoyl, $C_1-C_7$alkoxy-carbonyl such as $C_1-C_4$alkoxycarbonyl, phenyl-$C_1-C_4$alkoxycarbonyl, $C_1-C_4$alkanesulfonyl or benzenesulfonyl, $C_1-C_7$alkyl or phenyl-$C_1-C_7$alkyl; $R_3$ and $R_3'$ together represent a bond or $R_3$ denotes hydrogen, $C_2-C_8$alkanoyl, in particular $C_2-C_6$alkanoyl, phenyl-$C_2-C_6$alkanoyl, benzoyl, $C_1-C_7$alkoxy-carbonyl such as $C_1-C_4$alkoxycarbonyl, phenyl-$C_1-C_4$alkoxycarbonyl, $C_1-C_4$alkanesulfonyl or benzenesulfonyl, and $R_3'$ is hydrogen; $R_4$ denotes hydrogen, $C_3-C_7$cycloalkyl, phenyl, biphenylyl or naphthyl; $R_7$ denotes hydrogen or $C_1-C_7$alkyl; where the aromatic radicals in each case are unsubstituted or substituted one or more times by substituents selected from the group consisting of halogen, $C_1-C_7$alkyl, $C_1-C_7$alkoxy, hydroxyl, $C_2-C_8$alkanoyloxy, trifluoromethyl and nitro.

The invention particularly relates to compounds of the formula I and Ia and salts thereof, in which $-A_1-A_2-$, $-A_3-A_4-$, $-A_5-A_6-$ and $R_6$ have the indicated meanings; X represents $>C(R_6)-$ or $>N-$, and $R_6$ is hydrogen; alk denotes $C_1-C_7$alkylene, $C_3-C_7$alkenylene or $C_3-C_7$alkynylene, in particular $C_1-C_4$alkylene, $C_3-C_4$alkenylene or $C_3-C_4$alkynylene, where the multiple bonds are located in a position higher than $\alpha$ to the piperazine nitrogen; $R_1$, $R_2$ and $R_3$, independently of one another, denote $C_2-C_8$alkanoyl, in particular $C_2-C_6$alkanoyl, phenyl-$C_2-C_6$alkanoyl, $C_1-C_7$alkoxy-carbonyl such as $C_1-C_4$alkoxycarbonyl, phenyl-$C_1-C_4$alkoxycarbonyl, $C_1-C_4$alkanesulfonyl or benzenesulfonyl, and $R_1$ additionally and $R_3$ and $R_7$ denote hydrogen; $R_4$ denotes hydrogen, $C_3-C_7$cycloalkyl, phenyl, biphenylyl or naphthyl; where the aromatic radicals in each case are unsubstituted or substituted one or more times by substituents selected from the group consisting of halogen, $C_1-C_7$alkyl, $C_1-C_7$alkoxy, hydroxyl, $C_2-C_8$alkanoyloxy, trifluoromethyl and nitro.

The invention particularly relates to compounds of the formula I and Ia and salts thereof, in which $-A_1-A_2-$, $-A_3-A_4-$, $-A_5-A_6-$ have the indicated meanings; X represents $>C(R_6)-$ or $>N-$, and $R_6$ is hydrogen; alk denotes $C_1-C_7$alkenylene or $C_3-C_7$alkynylene, in particular $C_1-C_4$alkylene, $C_3-C_4$alkenylene or $C_3-C_4$alkynylene, where the multiple bonds are located in a position higher than $\alpha$ to the piperazine nitrogen; $R_1$, $R_2$ and $R_3$, independently of one another, denote $C_2-C_8$alkanoyl, in particular $C_2-C_6$alkanoyl, $C_1-C_4$alkoxycarbonyl, $C_1-C_4$alkanesulfonyl or benzenesulfonyl, and $R_1$ additionally and $R_3'$ and $R_7$ denote hydrogen; $R_4$ denotes hydrogen, $C_3-C_7$cycloalkyl, phenyl, biphenylyl or naphthyl; $R_5$ is acetyl; where the aromatic radicals in each case are unsubstituted or substituted one or more times by substituents selected from the group consisting of halogen, $C_1-C_4$alkyl, $C_1-C_4$alkoxy, hydroxyl, $C_2-C_6$alkanoyloxy, trifluoromethyl and nitro.

The invention particularly relates to compounds of the formula I and Ia and salts thereof, in which $-A_1-A_2-$, $-A_3-A_4-$, $-A_5-A_6-$ have the indicated meanings; X represents $>C(R_6)-$ or $>N-$, and $R_6$ is hydrogen; alk denotes $C_1-C_7$alkylene, in particular $C_1-C_4$alkylene; $R_1$ denotes $C_2-C_8$alkanoyl, in particular $C_2-C_6$alkanoyl; $R_2$ denotes $C_2-C_8$alkanoyl, in particular $C_2-C_6$alkanoyl, benzoyl, $C_1-C_4$alkanesulfonyl or benzenesulfonyl, $C_1-C_4$alkyl or phenyl-$C_1-C_4$alkyl, $R_3$ and $R_3'$ together represent a bond, or $R_3$ denotes hydrogen, $C_2-C_8$alkanoyl, in particular $C_2-C_6$alkanoyl, benzoyl, $C_1-C_4$alkanesulfonyl or benzenesulfonyl, and $R_3'$ is hydrogen; $R_4$ denotes hydrogen, $C_3-C_7$cycloalkyl, phenyl, biphenylyl or naphthyl, $R_5$ is acetyl; $R_7$ is hydrogen or $C_1-C_4$alkyl; where the aromatic radicals in each case are unsubstituted or substituted one or more times by substituents selected from the group consisting of halogen, $C_1-C_4$alkyl, $C_1-C_4$alkoxy, hydroxyl, $C_2-C_6$alkanoyloxy, trifluoromethyl and nitro.

The invention particularly relates to compounds of the formula I and Ia and salts thereof, in which $-A_1-A_2-$, $-A_3-A_4-$ and $-A_5-A_6-$ have the indicated meanings; X represents $>C(R_6)-$ or $>N-$, and $R_6$ is hydrogen; alk denotes $C_1-C_4$alkylene such as methylene or 2-methyl-1,3-propylene, or $C_3-C_5$alkenylene such as 1,4-but-2-enylene, where the double bond is located in a position higher than $\alpha$ to the piperazine nitrogen; $R_1$ denotes hydrogen or branched $C_3-C_6$alkanoyl such as pivaloyl; $R_2$ denotes $C_2-C_6$alkanoyl such as acetyl, propionyl or pivaloyl, $C_1-C_4$alkoxy-carbonyl such as methoxy- or ethoxy-carbonyl, $C_1-C_4$alkanesulfonyl such as methanesulfonyl, or benzenesulfonyl which is optionally substituted by $C_1-C_4$alkyl or halogen with atomic number up to and including 35, such as p-bromophenyl- or p-toluene-sulfonyl, $R_3$ denotes $C_2-C_6$alkanoyl such as acetyl, propionyl or pivaloyl, $C_1-C_4$alkoxycarbonyl such as methoxy- or ethoxycarbonyl, $C_1-C_4$alkanesulfonyl such as methanesulfonyl, or benzenesulfonyl which is optionally substituted by $C_1-C_4$alkyl or halogen with atom up to and including 35, such as p-bromophenyl- or p-toluenesulfonyl; $R_3'$ is hydrogen; $R_4$ denotes hydrogen, $C_3-C_7$cycloalkyl such as cyclohexyl, optionally $C_1-C_4$alkyl-substituted phenyl, biphenylyl or naphthyl, such as 2,4,6-trimethylphenyl, 4-biphenylyl or 2-naphthyl; $R_5$ is acetyl; $R_7$ is hydrogen.

The invention particularly relates to compounds of the formula I and Ia and salts thereof, in which —$A_1$—$A_2$—, —$A_3$—$A_4$— and —$A_5$—$A_6$— have the indicated meanings; X represents $>C(R_6)$— or $>N$—, and $R_6$ is hydrogen; alk denotes $C_1$-$C_4$alkylene such as methylene, 2-methyl-1,3-propylene or 3-methyl-1,4-butylene; $R_1$ denotes hydrogen or branched $C_3$-$C_6$alkanoyl, in particular pivoloyl; $R_2$ denotes $C_2$-$C_6$alkanoyl such as acetyl, propionyl or pivaloyl, benzoyl or $C_1$-$C_4$alkyl-sulfonyl such as methanesulfonyl, $C_1$-$C_4$alkyl such as methyl or ethyl, phenyl-$C_1$-$C_4$alkyl such as benzyl or 2-phenyl-ethyl; $R_3$ denotes hydrogen, $C_2$-$C_6$alkanoyl such as acetyl, propionyl or pivaloyl, benzoyl or $C_1$-$C_4$alkanesulfonyl such as methanesulfonyl, and $R_3'$ is hydrogen; $R_4$ denotes hydrogen, $C_3$-$C_7$cycloalkyl such as cyclopentyl or -hexyl, phenyl which is optionally substituted by $C_1$-$C_4$alkyl, in particular 2,4,6-trimethylphenyl; $R_5$ is acetyl; $R_7$ denotes hydrogen or $C_1$-$C_4$alkyl such as methyl.

The invention particularly relates to compounds of the formula I and Ia and salts thereof, in which the structural elements —$A_1$—$A_2$—, —$A_3$—$A_4$— and —$A_5$—$A_6$— have the indicated meanings; primarily each denote ethylene; X represents $>N$—; $R_1$ denotes branched $C_3$-$C_6$alkanoyl, in particular pivaloyl; $R_2$ denotes $C_2$-$C_5$alkanoyl such as acetyl; $R_3$ denotes $C_2$-$C_5$alkanoyl such as acetyl, propionyl or pivaloyl; $R_3'$ is hydrogen; $R_5$ is acetyl and, on the one hand, alk denotes $C_1$-$C_4$alkylene, primarily 2-methyl-1,3-propylene and $R_4$ denotes hydrogen or, on the other hand, alk is methylene and $R_4$ denotes 2,4,6-trimethylphenyl, and $R_7$ is hydrogen in each case.

The invention particularly relates to compounds of the formula I and Ia and salts thereof, in which —$A_1$—$A_2$—, —$A_3$—$A_4$— and —$A_5$—$A_6$— have the indicated meanings; X denotes in particular $>N$— or furthermore $>C(R_6)$—, and $R_6$ is hydrogen; $R_1$ denotes hydrogen or branched $C_3$-$C_6$alkanoyl, in particular pivaloyl; $R_2$ denotes $C_2$-$C_6$alkanoyl such as acetyl, furthermore propionyl or pivaloyl, or in particular $C_1$-$C_4$alkyl such as methyl or ethyl; $R_3$ denotes hydrogen, or $C_2$-$C_6$alkanoyl such as acetyl, propionyl or pivaloyl, and $R_3'$ is hydrogen; $R_5$ is acetyl; $R_7$ denotes hydrogen or $C_1$-$C_4$alkyl such as methyl; alk denotes branched $C_3$-$C_5$alkylene such as 2-methyl-1,3-propylene or 2,2-dimethyl-1,3-propylene; and $R_4$ denotes hydrogen; or alk denotes methylene and $R_4$ denotes $C_3$-$C_7$cycloalkyl in particular cyclopentyl or -hexyl, or phenyl which is optionally substituted by $C_1$-$C_4$alkyl, in particular 2,4,6-trimethylphenyl.

The invention primarily relates to compounds of the formula I and Ia and salts thereof, in which the structural elements —$A_1$—$A_2$—, —$A_3$—$A_4$— and —$A_5$—$A_6$— each denote the ethylene; X represents $>N$—; $R_1$ denotes branched $C_3$-$C_6$alkanoyl, in particular pivaloyl; $R_2$ and $R_3$ each denote $C_2$-$C_5$alkanoyl such as acetyl, propionyl or pivaloyl, and $R_3'$ is hydrogen; or $R_2$ denotes $C_2$-$C_5$alkanoyl such as acetyl, propionyl or pivaloyl, or $C_1$-$C_1$alkyl such as methyl or ethyl, $R_3$ denotes hydrogen or $C_2$-$C_5$alkanoyl such as acetyl, propionyl or pivaloyl, and $R_3'$ is hydrogen or $R_3$ and $R_3'$ together represent a bond; $R_5$ is acetyl; alk-$R_4$ denotes isobutyl, cyclopentylmethyl, cyclohexylmethyl, benzyl, 2,4,6-trimethylbenzyl; $R_7$ is hydrogen or $C_1$-$C_4$alkyl such as methyl.

The invention primarily relates to compounds of the formula I and Ia and salts thereof, in which the structural elements —$A_1$—$A_2$—, —$A_3$—$A_4$— and. —$A_5$—$A_6$— each denote the ethylene; X represents $>N$—; $R_1$ denotes branched $C_3$-$C_6$alkanoyl, in particular pivaloyl; $R_2$ and $R_3$ each denote $C_2$-$C_5$alkanoyl such as acetyl, propionyl or pivaloyl, and $R_3'$ is hydrogen; or $R_2$ denotes $C_1$-$C_1$alkyl such as methyl or ethyl, $R_3$ denotes hydrogen or $C_2$-$C_5$alkanoyl such as acetyl, propionyl or pivaloyl, and $R_3'$ is hydrogen; $R_5$ is acetyl; alk-$R_4$ denotes isobutyl, cyclopentylmethyl, cyclohexylmethyl, benzyl, 2,4,6-trimethylbenzyl; $R_7$ is hydrogen, furthermore $C_1$-$C_4$alkyl such as methyl.

The invention primarily relates to compounds of the formula I and Ia and salts thereof, in which the structural elements —$A_1$—$A_2$—, —$A_3$—$A_4$— and —$A_5$—$A_6$— each have the indicated meanings; X represents $>N$—; $R_1$ denotes branched $C_3$-$C_6$alkanoyl, in particular pivaloyl; $R_2$ and $R_3$ each denote $C_2$-$C_5$alkanoyl such as acetyl, propionyl or pivaloyl, and $R_3'$ is hydrogen; or $R_2$ denotes $C_1$-$C_1$alkyl such as methyl or ethyl, and $R_3$ denotes hydrogen or $C_2$-$C_5$alkanoyl such as acetyl, furthermore propionyl or pivaloyl, and $R_3'$ is hydrogen; $R_5$ is acetyl; alk-$R_4$ denotes $C_3$-$C_5$alkyl in particular isobutyl or neopentyl, or $C_3$-$C_6$cycloalkylmethyl in particular cyclopentylmethyl or cyclohexylmethyl, or benzyl substituted by $C_1$-$C_4$-alkyl, especially 2,4,6-tri-$C_1$-$C_4$-alkyl-benzyl, in particular 2,4,6-trimethylbenzyl; $R_7$ is hydrogen, furthermore $C_1$-$C_4$alkyl such as methyl.

The invention primarily relates to compounds of the formula I and Ia and salts thereof, in which the structural elements —$A_1$—$A_2$—, —$A_3$—$A_4$— and —$A_5$—$A_6$— each denote the ethylene; X represents $>N$—; $R_1$ denotes branched $C_3$-$C_6$alkanoyl, in particular pivaloyl; $R_2$ denotes $C_2$-$C_5$alkanoyl such as acetyl, propionyl or pivaloyl; $R_3$ and $R_3'$ together represent a bond; $R_5$ is acetyl; alk-$R_4$ denotes isobutyl, cyclohexylmethyl, benzyl, 2,4,6-trimethylbenzyl, naphthylmethyl or biphenylylmethyl such as 4-biphenylylmethyl; $R_7$ is hydrogen or $C_1$-$C_4$-alkyl such as methyl.

The invention primarily relates to compounds of the formula I and Ia and salts thereof, in which the structural elements —$A_1$—$A_2$—, —$A_3$—$A_4$— and —$A_5$—$A_6$— each denote the ethylene; X represents $>N$—; $R_1$ denotes branched $C_3$-$C_6$alkanoyl, in particular pivaloyl; $R_2$ denotes $C_2$-$C_5$alkanoyl such as acetyl, propionyl or pivaloyl; $R_3$ and $R_3'$ are each hydrogen; $R_5$ is acetyl; alk-$R_4$ denotes isobutyl, cyclohexylmethyl, benzyl, 2,4,6-trimethylbenzyl, naphthylmethyl or biphenylylmethyl such as 4-biphenylylmethyl; $R_7$ is hydrogen.

The invention primarily relates to compounds of the formula I and Ia and salts thereof, in which the structural elements —$A_1$—$A_2$—, —$A_3$—$A_4$— and —$A_5$—$A_6$— each denote ethylene; X represents $>N$—; alk denotes $C_1$-$C_4$alkylene, in particular methylene; $R_1$ denotes branched $C_3$-$C_5$alkanoyl, in particular pivaloyl; $R_2$ denotes $C_2$-$C_5$alkanoyl, in particular acetyl, propionyl or pivaloyl; $R_3$ and $R_3'$ are each hydrogen; $R_4$ denotes 2,4,6-tri-$C_1$-$C_4$alkylphenyl, in particular 2,4,6-trimethylphenyl; $R_5$ denotes acetyl; $R_7$ is hydrogen.

The invention primarily relates to compounds of the formula I and Ia and salts thereof, in which the structural elements —$A_1$—$A_2$—, —$A_3$—$A_4$— and —$A_5$—$A_6$— each denote ethylene; X represents $>N$—; alk denotes $C_1$-$C_4$alkylene, in particular methylene; $R_1$ denotes branched $C_3$-$C_5$alkanoyl, in particular pivaloyl;

$R_2$ is $C_{-C_5}$alkanoyl, in particular acetyl, propionyl or pivaloyl, or $C_1$-$C_4$alkyl, in particular methyl or ethyl; $R_3$ denotes hydrogen or $C_2$-$C_5$alkanoyl, in particular acetyl, propionyl or pivaloyl; $R_3'$ is hydrogen; alk-$R_4$ denotes 2,4,6-tri-$C_1$-$C_4$alkylphenyl-$C_1$-$C_4$alkyl, in particular 2,4,6-trimethylphenylmethyl; $R_5$ denotes acetyl; $R_7$ is hydrogen, furthermore methyl or ethyl.

The invention primarily relates to compounds of the formula I and Ia and salts thereof, in which the structural elements —$A_1$—$A_2$—, —$A_3$—$A_4$— and —$A_5$—$A_6$— each denote ethylene; X represents >N—; alk denotes $C_1$-$C_4$alkylene, in particular methylene; $R_1$ denotes branched $C_3$-$C_5$alkanoyl, in particular pivaloyl; $R_2$ is $C_2$-$C_5$alkanoyl, in particular acetyl, propionyl or pivaloyl, or $C_1$-$C_4$alkyl, in particular methyl or ethyl; $R_3$ and $R_3'$ together represent a bond; alk-$R_4$ denotes 2,4,6-tri-$C_1$-$C_4$alkylphenyl-$C_1$-$C_4$alkyl, in particular 2,4,6-trimethylphenylmethyl; $R_5$ denotes acetyl; $R_7$ is hydrogen, furthermore methyl or ethyl.

The invention primarily relates to compounds of the formula I and Ia and salts thereof, in which the structural elements —$A_1$—$A_2$—, —$A_3$—$A_4$— and —$A_5$—$A_6$— each denote ethylene; X represents >N—; alk denotes $C_1$-$C_4$alkylene, in particular methylene; $R_1$ denotes branched $C_3$-$C_5$alkanoyl, primarily pivaloyl; $R_2$ is $C_2$-$C_5$alkanoyl, in particular acetyl, propionyl or pivaloyl; $R_3$ denotes $C_2$-$C_5$alkanoyl, in particular acetyl, propionyl or pivaloyl; $R_3'$ is hydrogen; alk-$R_4$ denotes 2,4,6-tri-$C_1$-$C_4$alkylphenyl-$C_1$-$C_4$alkyl, in particular 2,4,6-trimethylphenylmethyl; $R_5$ denotes acetyl; $R_7$ is hydrogen.

The invention primarily relates to compounds of the formula I and Ia and salts thereof, in which the structural elements —$A_1$—$A_2$—, —$A_3$—$A_4$— and —$A_5$—$A_6$— each denote ethylene; X represents >N—; alk denotes in particular methylene; $R_1$ denotes branched $C_3$-$C_5$alkanoyl, primarily pivaloyl; $R_2$ is $C_2$-$C_5$alkanoyl, in particular acetyl; $R_3$ denotes $C_2$-$C_5$alkanoyl, in particular acetyl; $R_3'$ is hydrogen; alk-$R_4$ denotes 2,4,6-tri-$C_1$-$C_2$alkylphenyl-methyl, in particular 2,4,6-trimethylphenylmethyl; $R_5$ denotes acetyl; $R_7$ hydrogen.

The invention primarily relates to compounds of the formula I and Ia and salts thereof, in which the structural elements —$A_1$—$A_2$—, —$A_3$—$A_4$— and —$A_5$—$A_6$— each denote ethylene or vinylene, or the elements —$A_1$—$A_2$— and —$A_3$—$A_4$— each denote ethylene and —$A_5$—$A_6$— denotes vinylene; X represents >N—; $R_1$ denotes branched $C_3$-$C_5$alkanoyl, primarily pivaloyl; $R_2$ denotes $C_1$-$C_4$alkyl in particular methyl, furthermore ethyl; $R_3$ and $R_3'$ each denote hydrogen; $R_5$ denotes acetyl; $R_7$ is hydrogen; and alk-$R_4$ denotes 2,4,6-trimethylbenzyl.

The invention primarily relates to compounds of the formula I and Ia and salts thereof, in which the structural elements —$A_1$—$A_2$—, —$A_3$—$A_4$— and —$A_5$—$A_6$— each denote vinylene; X represents >N—; $R_1$ denotes branched $C_3$-$C_5$alkanoyl, primarily pivaloyl; $R_2$ denotes $C_1$-$C_4$alkyl primarily methyl, furthermore ethyl; $R_3$ and $R_3'$ each denote hydrogen; $R_5$ denotes acetyl; $R_7$ is hydrogen; and alk-$R_4$ denotes 2,4,6-trimethylbenzyl.

The invention also relates to compounds of formula I and Ia in which the structural elements —$A_1$—$A_2$—, —$A_3$—$A_4$— and —$A_5$—$A_6$— each have the indicated meanings; X represents >N—; $R_1$ denotes pivaloyl; $R_2$ denotes $C_2$-$C_5$alkanoyl or $C_1$-$C_4$-alkyl; $R_3$ denotes hydrogen or $C_2$-$C_5$alkanoyl; $R_3'$ represents hydrogen; or $R_3$ and $R_3'$ together represent a common bond; alk-$R_4$ denotes $C_3$-$C_5$-alkyl, $C_3$-$C_6$-cycloalkylmethyl, or benzyl 2,4,6-tri-substituted by $C_1$-$C_4$-alkyl; and salts thereof.

The invention further relates to the compounds of formula I and Ia in which the structural elements —$A_1$—$A_2$—, —$A_3$—$A_4$— and —$A_5$—$A_6$— each have the indicated meanings; X represents >N—; $R_1$ denotes pivaloyl; $R_2$ denotes $C_1$-$C_4$-alkyl; $R_3$ and $R_3'$ each denote hydrogen; or $R_3$ and $R_3'$ together represent a common bond; $R_5$ denotes acetyl; $R_7$ denotes hydrogen; and alk-$R_4$ denotes 2,4,6-trimethylbenzyl, neopentyl or cyclohexylmethyl; and salts thereof.

The invention also relates to compounds of formula I and Ia in which the structural elements —$A_1$—$A_2$—, —$A_3$—$A_4$— and —$A_5$—$A_6$— each have the indicated meanings; X represents >N—; $R_1$ denotes aminocarbonyl disubstituted by $C_1$-$C_3$-alkyl; $R_2$ denotes $C_2$-$C_5$-alkanoyl or $C_1$-$C_4$-alkyl; $R_3$ denotes hydrogen or $C_2$-$C_5$-alkanoyl; $R_3'$ represents hydrogen; or $R_3$ and $R_3'$ together represent a common bond; alk-$R_4$ denotes $C_3$-$C_5$-alkyl, $C_3$—$C_6$-cycloalkylmethyl, or benzyl 2,4,6-tri-substituted by $C_1$-$C_4$-alkyl; and salt thereof.

The invention further relates to the compounds of formula I and Ia in which the structural elements —$A_1$—$A_2$—, —$A_3$—$A_4$— and —$A_5$—$A_6$— each have the indicated meanings; X represents >N—; $R_1$ denotes aminocarbonyl disubstituted by $C_1$-$C_3$-alkyl; $R_2$ denotes $C_1$-$C_4$-alkyl; $R_3$ and $R_3'$ each denote hydrogen; or $R_3$ and $R_3'$ together represent a common bond; $R_5$ denotes acetyl; $R_7$ denotes hydrogen; and alk-$R_4$ denotes 2,4,6-trimethylbenzyl, neopentyl or cyclohexylmethyl; and salts thereof.

The invention also relates to compounds of formula I and Ia in which the structural elements —$A_1$—$A_2$—, —$A_3$—$A_4$— and —$A_5$—$A_6$— each have the indicated meanings; X represents >N—; $R_1$ denotes 2-methoxy-2,2-dimethylacetyl; $R_2$ denotes $C_2$-$C_5$-alkanoyl or $C_1$-$C_4$-alkyl; $R_3$ denotes hydrogen or $C_2$-$C_5$-alkanoyl; $R_3'$ represents hydrogen; or $R_3$ and $R_3'$ together represent a common bond; alk-$R_4$ denotes $C_3$-$C_5$-alkyl, $C_3$-$C_6$-cycloalkylmethyl, or benzyl 2,4,6-tri-substituted by $C_1$-$C_4$-alkyl; and salts thereof.

The invention further relates to the compounds of formula I and Ia in which the structural elements —$A_1$—$A_2$—, —$A_3$—$A_4$— and —$A_5$—$A_6$— each have the indicated meanings; X represents >N—; $R_1$ denotes 2-methoxy-2,2-dimethylacetyl; $R_2$ denotes $C_1$-$C_4$-alkyl; $R_3$ and $R_3'$ each denote hydrogen; or $R_3$ and $R_3'$ together represent a common bond; $R_5$ denotes acetyl; $R_7$ denotes hydrogen; and alk-$R_4$ denotes 2,4,6-trimethylbenzyl, neopentyl or cyclohexylmethyl; and salts thereof.

The invention particularly relates to the novel compounds mentioned in the examples, and the preparation thereof.

The invention likewise relates to processes for the preparation of the compounds according to the invention. The preparation of compounds of the formula I and salts thereof is carried out in a manner known per se and is characterized in that, for example, a) for the preparation of compounds of the formula I and salts thereof, in which X represents >N—, a compound of the formula

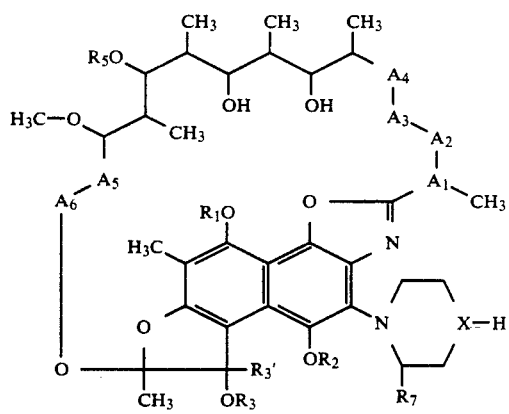

or a salt thereof, in which X represents >N—, is reacted with a compound of the formula Z-alk-R$_4$ (IIb)

in which Z denotes reactive esterified hydroxyl, or
b) a compound of the formula

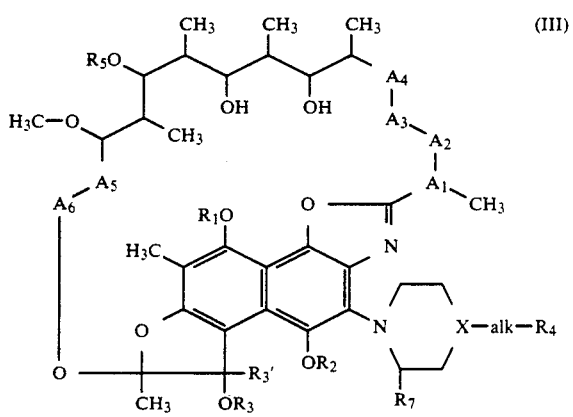

in which R$_2$ is hydrogen, is alkylated and/or in which at least one of the radicals R$_1$, R$_2$ and/or R$_3$ denotes hydrogen is acylated, or
c) a compound of the formula

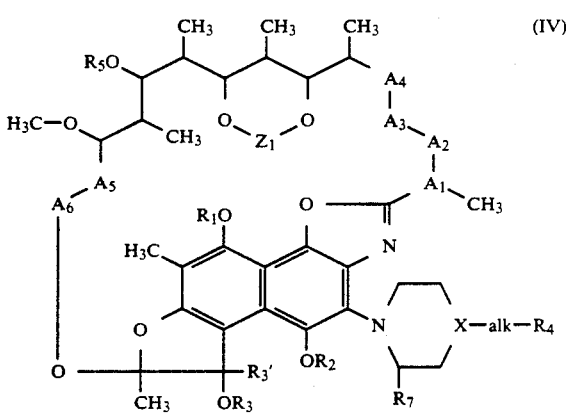

in which Z$_1$ denotes alkylidene or cycloalkylidene, is hydrolysed, and, if desired, a compound of the formula I obtainable according to the process or by other means, or a salt thereof, is converted into another compound according to the invention, or a salt thereof, a free compound of the formula I obtainable according to the process is converted into a salt and/or a salt obtainable according to the process is converted into the free compound of the formula I or into another salt and, if desired, a mixture of isomers obtainable according to the process is fractionated.

Salts of the starting materials of the formulae IIa, III and IV which have an acidic phenolic hydroxyl group are appropriate salts with bases of the type detailed hereinbefore, whereas the starting compounds of the formula IIa, III or IV which have one or two basic centres can form corresponding acid addition salts in analogy to the acid addition salts of the formula I.

Reactive esterified hydroxyl, for example Z, is, in particular, hydroxyl which is esterified with a strong inorganic acid or organic sulfonic acid, for example halogen such as chlorine, bromine or iodine, sulfonyloxy such as hydroxysulfonyloxy, halogenosulfonyloxy, for example fluorosulfonyloxy, optionally substituted, for example by halogen, C$_1$-C$_7$alkanesulfonyloxy, for example methane- or trifluoromethanesulfonyloxy, C$_5$-C$_7$cycloalkanesulfonyloxy, for example cyclohexanesulfonyloxy, or optionally substituted, for example by C$_1$-C$_7$alkyl or halogen, benzenesulfonyloxy, for example p-bromobenzene- or p-toluenesulfonyloxy.

Alkylidene denotes, for example, C$_1$-C$_7$alkylidene, in particular C$_1$-C$_5$alkylidene such as methylene, ethylidene, isopropylidene, 1-methyl-propylidene or -butylidene, whereas cycloalkylidene denotes, for example, C$_3$-C$_7$cycloalkylidene, in particular cyclopentylidene or -hexylidene.

The reactions described hereinbefore and hereinafter in the variants are carried out in a manner known per se, for example, in the absence or customary manner in the presence of a suitable solvent or diluent or of a mixture thereof, and they are carried out, as required, with cooling, at room temperature or with heating, for example in a temperature range from about −80° up to the boiling point of the reaction medium, preferably from about −10° up to about +180° C. and, if necessary, in a closed vessel, under pressure, in an inert gas atmosphere and/or under anhydrous conditions.

Variant a): Z preferably denotes halogen, such as chlorine, bromine or iodine, furthermore sulfonyloxy such as methane- or p-toluenesulfonyloxy.

The reaction is carried out in a manner known per se, advantageously in the presence of a base.

Suitable and preferred bases are non-nucleophilic tertiary amines, for example tri-lower-alkylamines, basic heterocycles and carbocyclic amines such as ethyl-diisopropylamine, triethylamine, pyridine, 1,5-diazabicyclo[4.3.0]non-5-ene (DBN) and 1,8-diaza-bicyclo[5.4.0]undec-7-ene (DBU).

Variant b): The acylation is carried out in a manner known per se using a suitable acylating agent. An example of a suitable acylating agent is a compound of the formula Ac-Z$_2$ (IIIa), where Ac denotes an acyl radical corresponding to the variables R$_1$, R$_2$ and R$_3$, and Z$_2$ denotes hydroxyl or, in particular, reactive activated hydroxyl. Appropriate hydroxyl can be activated, for example, by strong acids such as hydrohalic or carboxylic acid, for example by hydrochloric, hydrobromic acid, an optionally substituted, for example by halogen, alkanecarboxylic acid or by an acid of the formula Ac-OH, or by suitable activating or coupling reagents of the type detailed hereinafter, in particular in situ. Ac-Z$_2$ can furthermore represent an activated ester, where $Z_2$ denotes, in particular, cyanomethoxy, (4-)nitrophenoxy or polyhalogeno-, such as pentachloro-, -phenoxy. Activating and coupling reagents which can be employed are, in particular, carbodiimides, for example N,N'-di-$C_1$-$C_4$alkyl- or N,N'-di-$C_5$-$C_7$cycloalkyl-carbodiimide, such as diisopropylcarbodiimide or N,N'-dicyclohexyl-carbodiimide, advantageously with the addition of an activating catalyst such as N-hydroxysuccinimide or optionally substituted, for example by halogen, $C_1$-$C_7$alkyl or $C_1$-$C_7$alkoxy, N-hydroxy-benzotriazole or N-hydroxy-5-norbornene-2,3-dicarboxamide, furthermore $C_1$-$C_4$alkyl halogenoformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methylisoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, furthermore triphenylphosphine disulfide or 1-$C_1$-$C_4$alkyl-2-halogeno-pyridinium halides, for example 1-methyl-2-chloropyridinium iodide.

$Z_2$ preferably denotes halogen such as chlorine or bromine, and Ac—O—.

The acylation according to the invention is preferably carried out under mild conditions, for example at room temperature or slightly elevated temperatures. Depending on the nature of the starting material of the formula III, the amount of acylating agent must be selected so that one, two or, secondarily, three acyl groups are introduced. The acylating agent can advantageously act as solvent. The course of the reaction is expediently followed by customary analytical methods, in particular using thin-layer chromatography.

If the acylation is carried out with a compound of the formula Ac-$Z_2$ in which $Z_2$ denotes halogen, it is advantageously carried out in the presence of an acid-binding agent such as a base which cannot be acylated. Suitable bases are, for example, alkali metal hydroxides, hydrides, amides, alkanolates, carbonates, triphenylmethylides, di(lower alkyl)amides, aminoalkylamides or lower alkyl silylamides, or naphthaleneamines, lower alkylamines, basic heterocycles, ammonium hydroxides, and also carbocyclic amines. Examples which may be mentioned are sodium hydroxide, sodium hydride, sodium amide, sodium (m)ethoxide, potassium tert-butoxide, caesium carbonate, potassium carbonate, lithium triphenylmethylide, lithium diisopropylamide, potassium 3-(aminopropyl)amide, potassiumbis(trimethylsilyl)amide, dimethylaminonaphthalene, di- or triethylamine, or ethyldiisopropylamine, N-methylpiperidine, pyridine, benzyltrimethylammonium hydroxide, 1,5-diazabicyclo[4.3.0]non-5-ene (DBN) and 1,8-diazabicyclo[5.4.0]undec-7-ene (DBU). In the reaction with an anhydride, in particular a symmetric anhydride, an excess of Ac-O-Ac is used, in particular.

A preferred embodiment of the acylation process according to the invention starts from those compounds of the formula III in which $R_1$ denotes acyl, $R_5$ is acetyl, and $R_2$ and $R_3$ denote hydrogen. Depending on the choice of reaction conditions, the acylation can be controlled in such a way that only the oxygen atom on C-4 of the rifamycin ring system is acylated. This entails, in particular, acylation at room temperature with the particular acylating agent, which simultaneously acts as solvent. If the temperature is raised, or if, for example, a compound of the formula IIIa is employed while using a base in which $Z_2$ denotes halogen, the O atom on C-4 and C-11, in particular, are simultaneously acylated.

If $R_2$ denotes hydrogen, this phenolic 4-hydroxyl group can be etherified in a manner known per se. The etherification can be carried out, for example, with a reactive ester of the alkanol which is optionally substituted by an aromatic radical. Examples of suitable reactive esters of the relevant alcohols are those with strong inorganic or organic acids, such as appropriate halides, sulfates, sulfonates, for example lower alkanesulfonates or optionally substituted benzenesulfonates, in particular chlorides, bromides, iodides, methane-, benzene- or p-toluenesulfonates. The etherification can be carried out, for example, in the presence of a base such as an alkali matel hydride, hydroxide, carbonate or of a basic amine. It is advantageous to start from an appropriate alkali metal salt of the formula III.

If $R_2$ denotes alkanoyl and $R_3$ denotes hydrogen, the corresponding 4-O-acyl derivative may be in equilibrium with the corresponding 11-O-acyl derivative, that is to say the 4-O-acyl group migrates to the 11-hydroxyl group.

The preparation of compounds of the formula I in which $R_2$ denotes alkyl which is optionally substituted by an aromatic radical, and $R_3$ denotes acyl, primarily alkanoyl, can start from corresponding compounds of the formula III in which $R_2$ is acyl and $R_3$ denotes hydrogen, and the latter are alkylated in the indicated manner, preferably under basic conditions.

If both $R_2$ and $R_3$ denote hydrogen, under usual reaction conditions, the 4-OH group is preferably esterified or etherified, respectively, first.

The preparation of the starting material of the formula III starts, for example, from rifamycin S

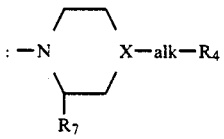

in position 3 in a manner known per se, for example as described in WO 87/02361 (U.S. Pat. No. 4,918,066). The appropriate SV derivative is subsequently converted using an acylating agent, such as pivaloyl chloride, into the corresponding 1,8-di-O-acyl compound and then, by prolonged heating, for example at 100° C., into the corresponding 8-O-acyl-1-deoxy-1,15-oxy derivative of the formula III. Corresponding hydro compounds can be prepared by hydrogenation in a manner known per se, for example as described hereinafter.

Variant c): $Z_1$ primarily represents $C_1$-$C_5$alkylidene such as isopropylidene. The ketal of the formula IV is hydrolysed in a manner known per se, advantageously using an acid such as an inorganic or organic acid, such as mineral acid, for example a hydrohalic acid, sulfuric acid or a phosphorus acid, sulfonic acid, for example methane- or p-toluenesulfonic acid, or a carboxylic acid, for example acetic acid.

The preparation of compounds of the formula IV is carried out in a manner known per se. Thus, for example, it starts from a compound of the formula I in which $R_2$ is hydrogen and $R_3$ and $R_3'$ together represent a bond or each denote hydrogen, and the latter is reacted in the presence of one of the listed acids with an aldehyde or ketone, or a ketal thereof, such as di-$C_1$-$C_4$alkyl or $C_2$-$C_4$alkylene ketal, for example acetone dimethyl ketal, corresponding to $Z_1$. In turn, compounds of the formula I in which —$A_1$—$A_2$—, —$A_3$—$A_4$— and —$A_5$—$A_6$— each denote vinylene, and $R_3$ and $R_3'$ together represent a bond, are described, for example, in EP 314624. Corresponding hydro derivatives (—$A_1$—$A_2$—, —$A_3$—$A_4$— and —$A_5$—$A_6$— denote ethylene, for example) can be obtained, for example, using the hydrogenation processes detailed hereinafter.

The 11-oxo compounds (of formula I, Ia, IIa, III or IV in which $R_3$ and $R_3'$ represents a bond) can be selectively reduced to the 11-hydroxy compounds using e.g. an alkali metal borohydride such as sodium or lithium borohydride.

The invention likewise relates to the novel compounds obtainable by the abovementioned process variants.

A compound of the formula I obtainable according to the invention or in another manner, or salt thereof, can be converted in a manner known per se into another compound of the formula I.

Compounds of the formula I in which the structural elements —$A_1$—$A_2$—, —$A_3$—$A_4$— and —$A_5$—$A_6$— each denote vinylene or —$A_1$—$A_2$— and —$A_3$—$A_4$— each denote ethylene and —$A_5$—$A_6$— denotes vinylene can be converted by reduction, for example by catalytic hydrogenation, into the corresponding tetrahydro- (—$A_1$—$A_2$— and —$A_3$—$A_4$— are each ethylene and —$A_5$—$A_6$— is vinylene) or the corresponding hexahydro derivatives (—$A_1$—$A_2$—, —$A_3$—$A_4$— and —$A_5$—$A_6$— each denote ethylene). Thus the hydrogenation of the multiple bonds takes place in the presence of hydrogenation catalysts, suitable for this purpose being, for example, noble metals or derivatives thereof, for examples oxides, such as nickel, Raney nickel, palladium, platinum oxide, which can optionally be absorbed on support materials, for example on charcoal or calcium carbonate. The hydrogenation can be carried out, in particular, under pressures of 1 to about 100 at.

Acetyl $R_5$ can selectively be replaced by hydrogen in the presence of other acyl groups, for example, if $R_1$ denotes pivaloyl, by treatment with hydrazine (hydrate) or a suitable derivative thereof.

Compounds of the formula I in which, for example one of the radicals $R_1$, $R_2$ and $R_3$ denotes acyl, and at least one of the other radicals is hydrogen, can be acylated in a manner known per se, for example in analogy to the methods described in variant b), for example by reaction with the appropriate carboxylic acid or with a reactive derivative thereof. Examples of reactive derivatives of this type are anhydrides, including mixed anhydrides, such as an acid halide, for example chloride, or anhydrides with a formic ester, activated carboxylic esters such as cyanomethyl, (4-)nitrophenyl, polyhalogenophenyl, for example pentachlorophenyl, esters. The reaction with the carboxylic acid or a salt thereof takes place under water-eliminating conditions, for example with azeotropic removal of the water of reaction, or by treatment with a suitable condensing agent, for example N,N'-dicyclohexyl-carbodiimide. The reaction with a reactive acid derivative is advantageously carried out in the presence of a base. Correspondingly, the acetyl radical $R_5$ can be introduced into compounds of the formula I in which $R_5$ is hydrogen by treatment with an appropriate acetylating agent.

It is possible by treatment with strong bases, such as alkali metal hydroxides, to replace the acetyl radical $R_5$ and the acyl radical $R_1$, $R_2$ and/or $R_3$ by hydrogen. The acyl radical $R_1$ can also be selectively eliminated in the presence of the acetyl radical $R_5$, for example by treatment with a fluoride such as alkali metal, for example sodium or cesium fluoride, or with an ammonium fluoride, for example tetrabutylammonium fluoride.

Compounds of the formula I in which $R_2$ denotes alkyl which is optionally substituted by an aromatic radical can be converted in a manner known per se into those compounds of the formula I in which $R_2$ is hydrogen. The ether cleavage can be carried out, for example, using strong acids such as mineral acids, for example the hydrohalic acids hydrobromic or hydroiodic acid, which can advantageously be in the form of pyridinium halides, or using Lewis acids, for example halides of elements of the 3rd main group or corresponding subgroups of the periodic table of elements. If, for example, $R_2$ denotes benzyl, the latter can be eliminated using methods known per se, for example by catalytic hydrogenation, for example in the manner described hereinbefore. These reactions can, if necessary, be carried out while cooling or heating, for example in a temperature range from about $-20°$ to about $100°$ C., in the presence or absence of a solvent or diluent, under inert gas and/or under pressure and, where appropriate, in a closed vessel.

Salts of compounds of the formula (I) can be prepared in a manner known per se. Thus, for example, acid addition salts of compounds of the formula (I) are obtained by treatment with an acid or with a suitable ion exchanger reagent. Salts can be converted in a customary manner into the free compounds, acid addition salts, for example, by treatment with a suitable basic agent.

Depending on the procedure and reaction conditions, the compounds according to the invention with salt-forming, in particular basic, properties can be obtained in free form or, preferably, in the form of salts.

As a consequence of the close relationship between the novel compound in free form and in the form of salts thereof, hereinbefore and hereinafter by the free compound or salts thereof is meant, where appropriate for the sense and purpose, also the corresponding salts or the free compound.

The novel compounds, including their salts of salt-forming compounds, can also be obtained in the form of hydrates thereof, or include other solvents used for crystallization.

The novel compounds can, depending on the choice of starting materials and procedures, be in the form of one of the possible isomers or as mixtures thereof, for example depending on the number of asymmetric carbon atoms, as pure optical isomers, such as antipodes, or as mixtures of isomers, such as racemates, diastereoisomeric mixtures or racemate mixtures.

Racemate mixtures which are obtained can be separately fractionated on the basis of the physicochemical differences of the components in a known manner into the pure isomers or racemates, for example by fractional crystallization. Racemates which are obtained can, furthermore, be resolved by known methods into the optical antipodes, for example by recrystallization from an optically active solvent, chromatography on chiral adsorbents, using suitable microorganisms, by cleavage with specific, immobilized enzymes, via the formation of inclusion compounds, for example using chiral crown ethers, in which case only one enantiomer is complexed, or by conversion into diastereomeric salts, for example by reaction of a basic final compound racemate with an optically active acid such as carboxylic acid, for example tartaric or mallic acid, or sulfonic acid, for example camphorsulfonic acid, and separation of the diastereomeric mixture obtained in this manner, for example on the basis of their different solubilities, into the diastereomers, from which the desired enantiomer can be liberated by the action of suitable agents. The more active enantiomer is advantageously isolated.

The working up of the reaction product from the reaction mixture obtainable according to the process is carried out in a manner known per se, for example by dilution with water, and/or where appropriate by neutralization or slight acidification (to about pH=3) with an aqueous acid, such as an inorganic or organic acid, for example a mineral acid or, advantageously, citric acid, and addition of a solvent which is immiscible with water, such as chlorinated hydrocarbon, for example chloroform or methylene chloride, in which case the reaction product transfers into the organic phase, from which it can be obtained in pure form in a customary manner, for example by drying, evaporation of the solvent and crystallization and/or chromatography of the residue or other customary purification methods. If the above reaction yields, for example, a mixture of acylated compounds, the latter can be fractionated in a manner known per se, for example by fractional crystallization, chromatography etc., into the desired individual acyl compounds.

The invention also relates to those embodiments of the process which start from a compound obtainable at any one stage of the process as intermediate, and the missing steps are carried out or a starting material is used in the form of a derivative or salt and/or its racemates or antipodes, or, in particular, is formed under the reaction conditions.

In the process of the present invention, the starting materials which are preferably used are those which lead to the compounds described as particularly valuable in the introduction. The invention likewise relates to novel starting materials which have been developed specifically for the preparation of the compounds according to the invention, in particular novel compounds of the formula III, the use thereof and processes for the preparation thereof, where the variables $-A_1-A_2-$, $-A_3-A_4-$, $-A_5-A_6-$, $R_1$, $R_2$, $R_3'$, $R_4$, $R_5$, $R_6$, $R_7$, X and alk have the meanings indicated for the preferred groups of compounds of the formula I in each case.

The present invention also embraces the use of compounds of the formula I and salts thereof alone or together with auxiliaries, as well as in combination with other active compounds, as agents for the therapeutic treatment, namely both curative and preventive, of diseases or pathological states indicated or caused, for example, by an elevated content of cholesterol and/or triglycerides in the blood, in particular in blood serum. The active compounds according to the invention are administered in therapeutically effective amounts, preferably in the form of pharmaceutical compositions together with conventional pharmaceutical vehicles and/or auxiliaries, to the warm-blooded animals, primarily humans, requiring treatment. This entails, for example, administration to warm-blooded animals, depending on the species, body weight, age and individual condition, of daily doses corresponding to about 1 to about 100, in particular about 3 to about 50, mg per kg of body weight, which can be exceeded in severe cases. Accordingly, the invention also embraces the corresponding method for medical treatment.

The invention likewise relates to pharmaceutical products which contain the compounds according to the invention, or pharmaceutically utilizable salts thereof, as active compounds, and to processes for the preparation thereof.

The pharmaceutical products according to the invention which contain the compound according to the invention or pharmaceutically utilizable salts thereof are those for enteral, such as oral furthermore rectal, and parenteral administration to warm-blooded animals(s), the pharmacological active compound being contained alone or together with a pharmaceutically utilizable vehicle. The daily dosage of the active compound depends on the age and the individual condition as well as on the mode of administration.

The novel pharmaceutical products contain, for example, from about 10% to about 80%, preferably from about 20% to about 60%, of the active compound. Examples of pharmaceutical products according to the invention for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated tablets.

Particularly suitable excipients are fillers such as sugars, for example lactose, sucrose, mannitol or sorbitol, cellulose products and/or calcium phosphates, for example tricalcium phosphate or calcium hydrogen phosphate, as well as binders such as starch mucillage using, for example, maize, wheat, rice or potato starch, gelatin, tragacanth, methylcellulose and/or polyvinylpyrrolidone, if desired, disintegrants such as the abovementioned starches, as well as carboxymethyl starch, cross-linked polyvinylpyrrolidone, agar, alginic acid or a salt thereof, such as sodium alginate, auxiliaries are primarily flowability and flow-regulating agents and lubricants, for example silica, talc, stearic acid or salts thereof, such as magnesium or calcium stearate, and/or polyethylene glycol. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound.

Further pharmaceutical products which can be used orally are two-piece capsules made of gelatin, as well as soft, closed capsules made of gelatin and a plasticizer such as glycerol or sorbitol. The two-piece capsules can contain the active compound in the form of granules, for example mixed with fillers such as lactose, binders such as starches, and/or glidants such as talc or magnesium stearate, and, where appropriate, stabilizers. The active compound in soft capsules is preferably dissolved or suspended in suitable liquids such as fatty oils, liquid paraffin or liquid polyethylene glycols, it likewise being possible to add stabilizers.

Examples of pharmaceutical products suitable for rectal use are suppositories which consist of a combination of the active compound and a suppository base. Examples of suitable suppository bases are natural or synthetic triglycerides, paraffin hydrocarbons, polyethylene glycols or higher alkanols. It is furthermore possible to use gelatin rectal capsules which contain a combination of the active compound with a base substance. Examples of suitable base substances are liquid triglycerides, polyethylene glycols or paraffin hydrocarbons.

Primarily suitable for parenteral administration are aqueous solutions of an active compound in water-soluble form, for example of a water-soluble salt, furthermore suspensions of the active compound such as appropriate oily injection suspensions, in which case suitable lipophilic solvents or vehicles such as fatty oils, for example sesame oil, or synthetic fatty acid esters, for example ethyl oleate or triglycerides, are used, or aqueous injection suspensions which contain viscosity-increasing substances, for example sodium carboxymethylcellulose, sorbitol and/or dextran and, where appropriate, also stabilizers.

The dosage of the active compound depends on the warm-blooded species, the age and the individual condition as well as the mode of administration. In the normal case for a warm-blooded animal weighing about 75 kg the estimated approximate daily dose on oral administration is about 150 mg to about 1500 mg, advantageously in several equal part-doses.

The examples which follow illustrate the invention described above; however, they are not intended to restrict the scope of the latter in any way. Temperatures are stated in degrees celsius.

The chemical name of the basic frameworks from which the rifamicyn derivatives of the present invention are derived is as follows:

1-deoxy-15-deoxo-1,15-oxy-rifamycin (A) [$R_3$ and $R_3'$ denote a common bond] and 11-hydroxy-11,15-deoxo-1-deoxy-1,15-oxy-rifamycin (B) [$R_3$ and $R_3'$ each denote hydrogen] can be represented as follows:

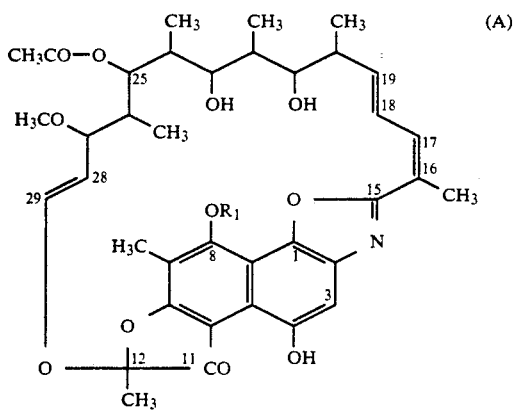

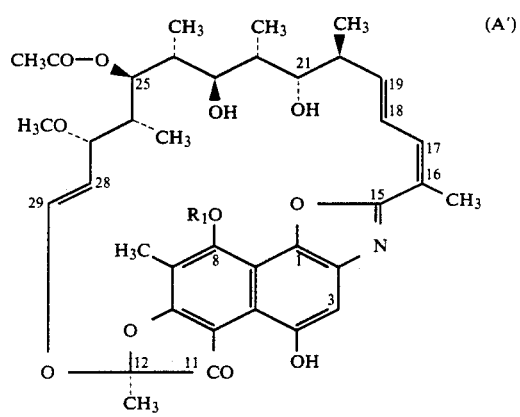

The stereochemical configurations corresponding to compounds of formula Ia (derived from rifamycin SV) are e.g. as follows:
(a) 1-deoxy-15-deoxo-1,15-oxy-rifamycin SV (A') [$R_3$ and $R_3'$ denote a common bond], and (b) 16,17,18,19-tetrahydro-11-hydroxy-11,15-dideoxo-1-deoxy-1,15-oxy-rifamycin SV (B) [$R_3$ an $R_3'$ each denote hydrogen].

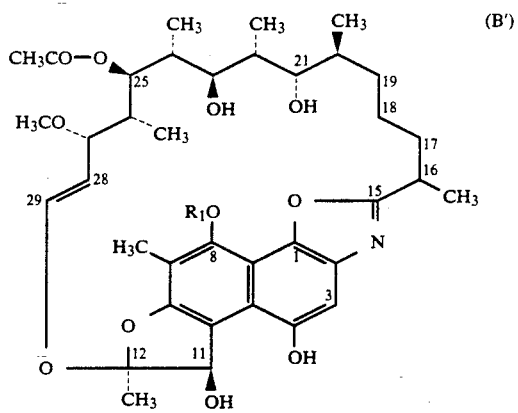

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

melt at 205°-208° with decomposition. $C_{58}H_{83}N_3O_{13}$; MW: 1029 (found: MS, FAB)

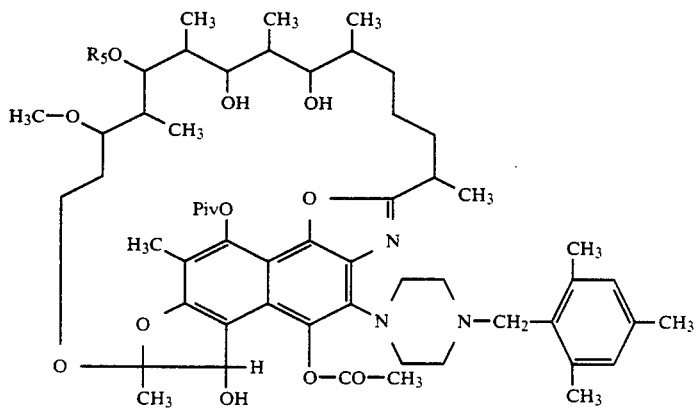

The stereochemical configuration of the products of the examples is, depending on the involved structure, assigned as depicted in formula A' or B', unless otherwise specified.

The configurations are assigned as in rifamycin SV. Furthermore, in 16,17-dihydro derivatives the 16-methyl group is assigned α, and in 11-hydroxy derivatives the 11-hydroxy group is assigned β.

EXAMPLE 1

2 g of 16,17,18,19,28,29-hexahydro-8-O-pivaloyl-11-hydroxy-11,15-dideoxo-1-deoxy-1,15-oxy-3-[4-(2,4,6-trimethylbenzyl)-piperazin-1-yl]-rifamycin SV are dissolved in 25 ml of acetic anhydride and stirred. When starting material is no longer detectable by thin-layer chromatography (on silica gel; hexane/ethyl acetate 2:1), the excess acetic anhydride is decomposed with the addition of methanol and water, and the reaction product is taken up in ethyl acetate. After drying over $Na_2SO_4$ and evaporation of the ethyl acetate extract there remains a colourless residue which crystallizes from diethyl ether/pentane and pentane. Obtained in this way is 16,17,18,19,28,29-hexahydro-4-O-acetyl-8-O-pivaloyl-11-hydroxy-11,15-dideoxo-1-deoxy-1,15-oxy-3-[4-(2,4,6-trimethylbenzyl)-piperazin-1-yl]-rifamycin SV of the formula I in which the structural elements —$A_1$—$A_2$—, —$A_3$—$A_4$— and —$A_5$—$A_6$— each denote ethylene, X represents >N—, alk denotes methylene, $R_1$ denotes pivaloyl, $R_2$ denotes acetyl, $R_3$, $R_3'$ and $R_7$ each denote hydrogen, $R_4$ denotes 2,4,6-trimethylphenyl and $R_5$ is acetyl, in colourless crystals which with stereochemistry as in structural configuration (B').

The starting material can be prepared as follows:

a) A mixture of 5 g of 3-[4-(2,4,6-trimethylbenzyl)-piperazin-1-yl]-rifamycin SV [prepared according to WO 87/02361, U.S. Pat. No. 4,918,066], 50 ml of dry pyridine and 4.5 ml of pivaloyl chloride is maintained at 50° for 30 minutes. The solvent is then evaporated in vacuo. The oily residue is dissolved in ethyl acetate and washed with 2N hydrochloric acid, with buffer solution pH=7 and with brine. After drying over sodium sulfate and evaporation, the yellow residue is crystallized from ether/hexane. Obtained in this way is 1,8-di-O-pivaloyl-3-[4-(2,4,6-trimethylbenzyl)-piperazin-1-yl)-rifamycin SV of melting point 203°-204°. $C_{61}H_{83}N_3O_{16}$; MW: 1081 (found, MS).

b) 30 g of 1,8-di-O-pivaloyl-3-[4-(2,4,6-trimethylbenzyl)-piperazin-1-yl]-rifamycin SV are dissolved in 1000 ml of hot 2-methoxyethanol and, under nitrogen, boiled under reflux for 5 hours. The solvent is then evaporated in vacuo, and the residue is crystallized twice from methanol. The result is 8-O-pivaloyl-1-deoxy-15-deoxo-1,15-oxy-3-[4-(2,4,6trimethylbenzyl)-piperazin-1-yl]-rifamycin SV of the formula I in which the structural elements —$A_1$—$A_2$—, —$A_3$—$A_4$— and —$A_5$—$A_6$— each denote ethylene, X represents >N—, alk denotes methylene, $R_1$ denotes pivaloyl, $R_2$ and $R_7$ each denote hydrogen, $R_3$ and $R_3'$ together represent a bond, $R_4$ denotes 2,4,6-trimethylphenyl and $R_5$ is acetyl. Melting point 160°-165°. $C_{56}H_{73}N_3O_{12}$; M=979, found (MS): 979; $^1$H NMR (360 MHz, CDCl$_3$, TMS): 1.49 (s, 9H, pivaloyl on O-8).

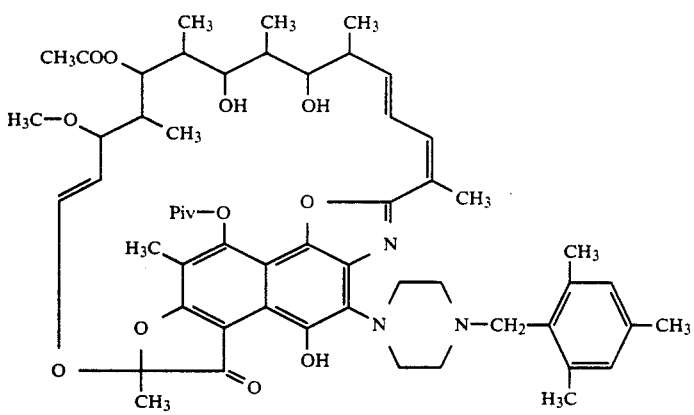

with stereochemistry as in structural configuration (A').

c) 5 g of the reaction product from b) are dissolved in 500 ml of ethanol and hydrogenated in the presence of 0.5 g of PtO$_2$ and 0.7 g of sulfuric acid at room temperature and under atmospheric pressure until 4 equivalents of hydrogen (~460 ml) have been taken up. The catalyst is removed by filtration, the filtrate is neutralized with aqueous sodium bicarbonate solution, saturated brine is added, and the hydrogenation product is extracted by repeated shaking with ethyl acetate. After drying and evaporation of the ethyl acetate extract, the residue is dissolved in ether. After standing for some time there is crystallization of 16,17,18,19,28,29-hexahydro-8-O-pivaloyl-11-hydroxy-11,15-dideoxo-1-deoxy-1,15-oxy-3-[4-(2,4,6-trimethyl-benzyl)-piperazin-1-yl]rifamycin SV of the formula Ia which the structural elements —A$_1$—A$_2$—, —A$_3$—A$_4$— and —A$_5$—A$_6$— each denote ethylene, X represents >N—, alk denotes methylene, R$_1$ denotes pivaloyl, R$_2$, R$_3$, R$_3$' and R$_7$ each denote hydrogen, R$_4$ denotes 2,4,6-trimethylphenyl and R$_5$ is acetyl. The pale brownish-red crystals, which form colourless plates after recrystallization from ether, melt at 225°-227° (decomposition). C$_{56}$H$_{81}$N$_3$O$_{12}$; MW: 987 (found; MS,FD).

oyl-11-hydroxy-1-deoxy-11,15-dideoxo-1,15-oxy-3-[4-(2,4,6-trimethylbenzyl)-piperazin-1-yl]-rifamycin SV of the formula Ia in which the structural elements —A$_1$—A$_2$—, —A$_3$—A$_4$— and —A$_5$—A$_6$— each denote ethylene, X represents >N—, alk denotes methylene, R$_1$ denotes pivaloyl, R$_2$ denotes propionyl, R$_3$, R$_3$' and R$_7$ each denote hydrogen, R$_4$ denotes 2,4,6-trimethylphenyl and R$_5$ is acetyl. Plate-like colourless crystals are formed from hexane and melt at 152°. C$_{59}$H$_{85}$N$_3$O$_{13}$; MW: 1043 (found, MS, FAB and DCI); $^1$H NMR (360 MHz, DMSO-d$_6$, 80°): 5.45 (d, 1H, H-11); 1.25 (t) and 2.73 (q-propionyl).

EXAMPLE 3

A solution of 3 g of 16,17,18,19,28,29-hexahydro-11-hydroxy-1-deoxy-11,15-dideoxo-1,15-oxy-3-[4-(2,4,6-trimethylbenzyl)-piperazin-1-yl]-rifamycin SV in 50 ml of pivalic anhydride is heated at 100° until all the starting material has reached. This is checked by thin-layer chromatography on silica gel with the eluent ethyl acetate/hexane (1:2). The reaction mixture is evaporated under high vacuum, and the colourless residue is dissolved in pentane. After removal of small amounts of insoluble material there is crystallization of

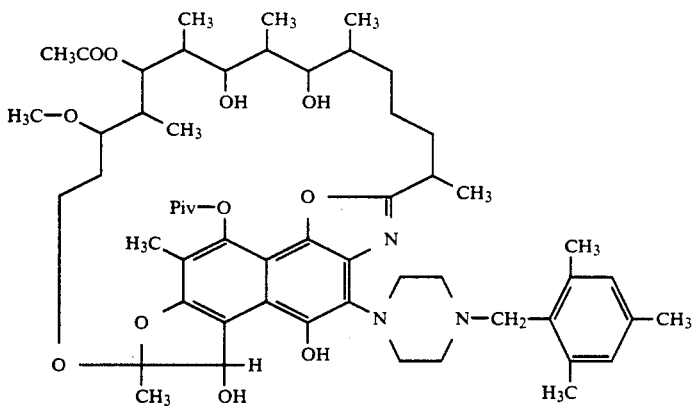

with stereochemistry as in structural configuration (B').

EXAMPLE 2

In an analogous manner, for example as described in Example 1, there is obtained, starting from 2 g of 16,17,18,19,28,29-hexahydro-11-hydroxy-1-deoxy-11,15-dideoxo-1,15-oxy-3-[4-(2,4,6-trimethylbenzyl)-piperazin-1-yl]-rifamycin SV and propionic anhydride, 16,17,18,19,28,29-hexahydro-4-O-propionyl-8-O-pival- 16,17,18,19,28,29-hexahydro-4-O,8-O-di-pivaloyl-11-hydroxy-1-deoxy-11,15-deoxo-1,15-oxy-3-[4-(2,4,6-trimethylbenzyl)-piperazin-1-yl]-rifamycin SV of the formula Ia in which the structural elements —A$_1$—A$_2$—, —A$_3$—A$_4$— and —A$_5$—A$_6$— each denote ethylene, X represents >N—, alk denotes methylene, R$_1$ and R$_2$ denote pivaloyl, R$_3$, R$_3$' and R$_7$ denote hydrogen, R$_4$ denotes 2,4,6-trimethylphenyl and R$_5$ is acetyl, in colourless hexagonal crystal plates of melting point 178°-179°. $C_{61}H_{89}N_3O_{13}$; MW; 1071 (found: MS, DCI):

EXAMPLE 4

0.8 g (0.8 mole) of 16,17,18,19,28,29-hexahydro-8-O-pivaloyl-11-hydroxy-1-deoxy-11,15-dideoxo-1,15-oxy-3-(4-isobutyl-1-piperazinyl)-rifamycin SV are dissolved in 5 ml of acetic anhydride and heated under a nitrogen atmosphere at 50° for one hour. The mixture is further stirred at room temperature for two hours. Excess acetic anhydride is removed in vacuo, and the residue is purified by flash chromatography (methylene chloride/methanol: 95/5). The resulting reddish oil is crystallized from methanol/water. Obtained in this way is 16,17,18,19,28,29hexahydro-4-O-acetyl-8-O-pivaloyl-11-acetyloxy-1-deoxy-11,15-dideoxo-1,15-oxy-3-(4isobutyl-1-piperazinyl)-rifamycin SV of the formula Ia in which $-A_1-A_2-$, $-A_3-A_4-$ and $-A_5-A_6-$ each denote ethylene, X represents >N—, $R_1$ represents pivaloyl, $R_2$, $R_3$ and $R_5$ each denote acetyl, alk denotes 2-methyl-1,3-propylene and $R_3'$, $R_4$ and $R_7$ each denote hydrogen.

Melting point: 142°-143°.

NMR: HO-(21 or 23): 4.25 ppm; HO-(23 or 21): 3.80 ppm. Me-(OOCCH$_3$ at 4): 2.2 ppm, s Me-(14): 2.1 ppm, s Me-(COCH$_3$): 2.08 ppm, s IR: 1643 cm-1 (COCH$_3$) 1735 cm-1 (OOCCH$_3$ at 25) 1760 cm-1 (OOCCH$_3$ at 4)

MS: 996 (M+1), 100

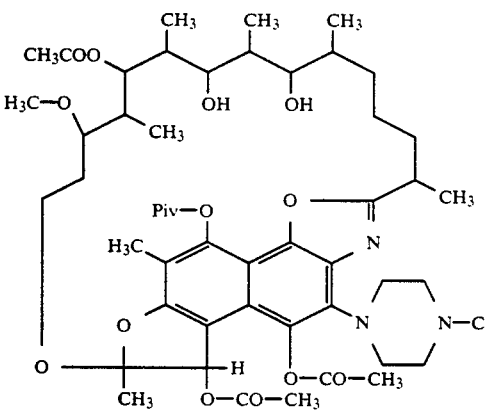

with stereochemistry as in structural configuration (B').

The starting material can be prepared as follows:

a) In a manner analogous to that described in Example 1 b), from 1,8-di-O-pivaloyl-3-(4-isobutyl-1-piperazinyl)-rifamycin SV there is obtained 8-O-pivaloyl-1-deoxy-15-deoxo-1,15-oxy-3-(4-isobutyl-1-piperazinyl)-rifamycin SV corresponding to the formula Ia in which the structural elements $-A_1-A_2-$, $-A_3-A_4-$ and $-A_5-A_6-$ each denote vinylene, X represents >N—, alk denotes 2-methyl-1,3-propylene, $R_1$ is pivaloyl, $R_2$, $R_4$ and $R_7$ each denote hydrogen, $R_3$ and $R_3'$ together represent a bond and $R_5$ is acetyl, of melting point 187°-188° C. (crystallized from methanol/water).

$C_{50}H_{69}N_3O_{12}$; MW: 903 (found, MS, FD). $^1$H NMR (360 MHz, CDCl$_3$): signals of the isobutyl group at 0.92 (6H, (CH$_3$)$_2$CH) 2.16 (d, 2H, CH$_2$N).

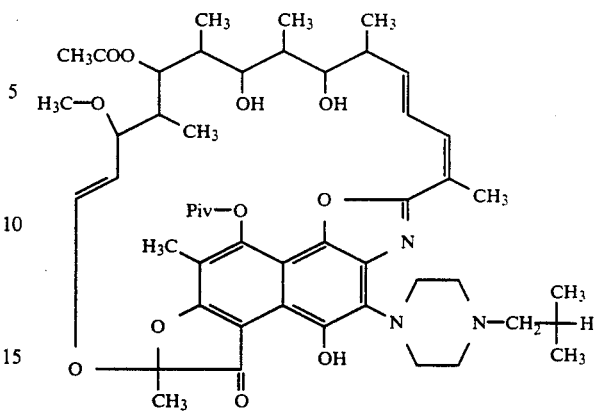

with stereochemistry as in structural configuration (A').

b) In a manner analogous to that described in Example 1 c), there is obtained, by hydrogenation with PtO$_2$ in ethanol with the addition of sulfuric acid, 16,17,18,19,28,29-hexahydro-8-O-pivaloyl-11-hydroxy-1-deoxy-11,15-dideoxo-1,15-oxy-3-(4-isobutyl-1-piperazinyl)-rifamycin SV corresponding to the formula Ia in which the structural elements $-A_1-A_2-$, $-A_3-A_4-$ and $-A_5-A_6-$ each denote ethylene, X represents >N—, alk denotes 2-methyl-1,3-propylene, $R_1$ denotes pivaloyl, $R_2$, $R_3$, $R_3'$, $R_4$ and $R_7$ each denote hydrogen and $R_5$ denotes acetyl. The pale reddish-coloured crystals form after recrystallization from hexane colourless, square plates which melt between 150° and 160°. $C_{50}H_{77}N_3O_{12}$; MW: 911 (found; MS, FD).

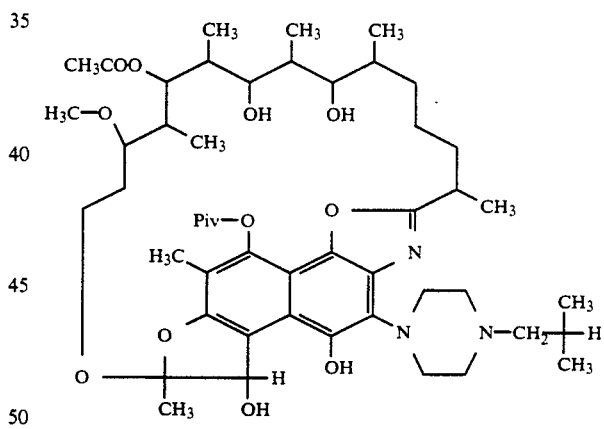

with stereochemistry as in structural configuration (B').

EXAMPLE 5

In an analogous manner, for example as described in Example 1, from 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV and diethyl pyrocarbonate there is obtained 16,17,18,19,28,29-hexahydro-4-O-ethoxycarbonyl-8-O-pivaloyl-11-hydroxy-1-deoxy-11,15-dideoxo-1,15-oxy-3-[4-(2,4,6-trimethylbenzyl)-piperazin-1-yl]-rifamycin SV of the formula Ia in which the structural elements $-A_1-A_2-$, $-A_3-A_4-$ and $-A_5-A_6-$ each denote ethylene, X represents >N—, alk denotes methylene, $R_1$ denotes pivaloyl, $R_2$ is ethoxycarbonyl, $R_4$ denotes 2,4,6-trimethylphenyl, $R_5$ denotes acetyl and $R_3$, $R_3'$ and $R_7$ each denote hydrogen. A small amount of quickly migrating impurities is removed from the reaction product by chromatography on silica gel with the eluent hexane/ethyl acetate (3:1).

$C_{59}H_{85}N_3O_{14}$; MW: 1059 (found: MS, DCI).

$^1$H NMR (360 MHz, DMSO-$d_6$, 80°, ppm): 1.36 (t, about 3H) and 4.28 (q, about 2H): COOCH$_2$CH$_3$; 5.50 (s, 1H): H-11.

EXAMPLE 6

In an analogous manner, for example as described in Example 1, starting from 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV and benzoic anhydride there is obtained 16,17,18,19,28,29-hexahydro-4-O-benzoyl-8-O-pivaloyl-11-hydroxy-1-deoxy11,15-dideoxo-1,15-oxy-3-[4-(2,4,6-trimethylbenzyl)-piperazin-1-yl]-rifamycin SV. A small amount of rapidly migrating impurities is removed from the reaction product by chromatography on silica gel with the eluent hexane/ethyl acetate (3:1). $C_{63}H_{85}N_3O_{12}$; MW: 1091 (found: MS DCI). $^1$H NMR (360 MHz, DMSO-$d_6$, 80°, ppm): 7.5–7.6 (m, about 3H) and about 8.5 (m, 2H): 5-arom. H of the benzoly group; about 5.38 (broad, about 1H): H-11.

EXAMPLE 7

In an analogous manner, for example as described in Example 4, starting from 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV and benzoic anhydride there is obtained 4-O-benzoyl-8-O-pivaloyl-11-benzoyloxy-1-deoxy-11,15-dideoxo-1,15-oxy-3-[4-(2,4,6-trimethylbenzyl)-piperazin-1-yl]-rifamycin SV. $C_{70}H_{89}N_3O_{14}$; MW: 1196 (found: MS, DCI).

EXAMPLE 8

50 ml of 2N aqueous sulfuric acid are added to a solution of 1.7 g of 16,17,18,19-tetrahydro-4-O-acetyl-8-O-pivaloyl-11-acetyloxy-1-deoxy-11,15-dideoxo-1,15-oxy-3-[4-(2,4,6-trimethylbenzyl)-piperazin-1-yl]-rifamycin SV-21,23-acetonide in 50 ml of tetrahydrofuran, and the mixture is left to stand at 25° for 2 hours. Then aqueous NaCl solution is added, the pH is adjusted to 7.5–8, and the reaction mixture is taken up in ether. After drying and evaporation of the solvent, the reaction mixture is separated by chromatography on silica gel with the eluent petroleum ether/ethyl acetate 3:1. First the starting material and finally, as main product, cream-coloured 16,17,18,19-tetrahydro-4-O-acetyl-8-O-pivaloyl-11-acetyloxy-1-deoxy-11,15-dideoxo-1,15-oxy-3-[4-(2,4,6-trimethylbenzyl)-piperazin-1-yl]-rifamycin SV is eluted with the $R_f$0.23. MW: 1069 (found: MS, DCI); $C_{60}H_{83}N_3O_{14}$.

The starting material can be prepared as follows, for example:

A solution of 2 g of 8-O-pivaloyl-1-deoxy-15-deoxo-1,15-oxy-3-[4-(2,4,6trimethylbenzyl)-piperazin-1-yl]-rifamycin is hydrogenated in 100 ml of ethanol in the presence of 0.2 g of palladium on charcoal (10%) at 25° under atmospheric pressure until hydrogen uptake has ceased. The catalyst is then removed by filtration, and the solvent is evaporated in vacuo. The dark-red residue is chromatographed on 200 g of silica gel with the eluent petroleum ether/ethyl acetate (3:1). The eluate of the main band is collected and evaporated. The residue consists of epimerically pure 16,17,18,19-tetrahydro-8-O-pivaloyl-1-deoxy-15-deoxo-1,15-oxy-3-[4-(2,4,6-trimethylbenzyl)piperazin-1-yl]-rifamycin SV. MW: 983 (found: MS).

2.3 g of p-toluenesulfonic acid are added to a solution of 7.95 g of 16,17,18,19-tetrahydro-8-O-pivaloyl-1-deoxy-15-deoxo-1,15-oxy-3-[4-(2,4,6-trimethylbenzyl)-piperazin-1-yl]rifamycin SV in 75 ml of acetone dimethyl ketal, and the mixture is left to stand at room temperature for four hours. It is then neutralized with excess sodium bicarbonate solution and diluted with water, and the reaction product is taken up with ether. After drying over Na$_2$SO$_4$ and evaporation of the ether solution, the residue is chromatographed through 800 g of silica gel with the solvent petroleum ether/ethyl acetate 3:1. The result is 16,17,18,19-tetrahydro-8-O-pivaloyl-1-deoxy-15-deoxo-1,15-oxy-3-[4-(2,4,6-trimethylbenzyl)-piperazin-1-yl]-rifamycin SV-21,23-acetonide as material with a deep red colour in the quickly migrating main band. MW: 1023 (found: MS, DCI); $C_{59}H_{81}N_3O_{12}$.

1% strength methanolic sodium borohydride solution is added dropwise at 25° to a 5% strength methanolic solution of 16,17,18,19-tetrahydro-8-pivaloyl-1-deoxy-15-deoxo1,15-oxy-3-[4-(2,4,6-trimethylbenzyl)-piperazin-1-yl]-rifamycin SV-21,23-acetonide until the red colour of the starting material has disappeared. Saturated brine is then added to the reaction mixture, and the product which has formed is taken up in ether. After the ethereal solution has been washed with buffer solution of pH 7 and with brine and has been dried with sodium sulfate it is evaporated in vacuo, resulting in a residue of 16,17,18,19tetrahydro-8-O-pivaloyl-11-hydroxy-1-deoxy-11,15-dideoxo-1,15-oxy-3-[4-(2,4,6-trimethylbenzyl)-piperazin-1-yl]-rifamycin SV-21,23-acetonide as a cream-coloured foam.

2 ml of acetic anhydride and 0.2 g of 4-dimethylaminopyridine are added to a solution of 1.8 g of this hexahydro derivative in 10 ml of pyridine, and the mixture is left to stand at room temperature for 1 hour. Then water and sodium chloride are added, the reaction product is taken up in ether/ethyl acetate, and the organic phase is washed several times with citric acid solution. After the organic phase has been further washed with sodium bicarbonate solution and saturated brine it is dried with sodium sulfate and evaporated. The result is a colourless residue, of 16,17,18,19-tetrahydro-4-O-acetyl-8-O-pivaloyl11-acetyloxy-1-deoxy-11,15-dideoxo-1,15-oxy-3-[4-(2,4,6-trimethylbenzyl)-piperazin-1-yl]rifamycin SV-21,23-acetonide. MW: 1109 (found: MS); $C_{63}H_{87}N_3O_{14}$.

EXAMPLE 9

0.5 g of 16,17,18,19,28,29-hexahydro-8-O-pivaloyl-11-hydroxy-1-deoxy-11,15-dideoxo-1,15-oxy-3-(4-isobutyl-piperazin-1-yl)-rifamycin SV is dissolved in 10 ml of acetic anhydride. To this is added 0.5 g of sodium acetate, and the solution is stirred at room temperature for 24 hours and at 50° for 5 hours. The solution is filtered through Celite, and the acetic anhydride is evaporated in vacuo. The residue is purified by chromatography on SiO$_2$ (Chromatotron, 4 mm; eluent: CH$_2$Cl$_2$/CH$_3$OH: 97/3) and by precipitation, where the residue is dissolved in 3 ml of CH$_3$OH and, while stirring, up to 30 ml of a 1:1 solution of CH$_3$OH/water is added. Filtration and drying result in 16,17,18,19,28,29-hexahydro-4-O-acetyl-8-O-pivaloyl-11-acetyloxy-1-deoxy-11,15-dideoxo-1,15-oxy-3-(4-isobutyl-piperazin-1-yl)-rifamycin SV as a beige powder, melting point 142°–143°.

The starting material can be prepared as follows, for example:

1 g (1.08 mmol) of 8-O-pivaloyl-1-deoxy-15-deoxo-1,15-oxy-3-(4-isobutyl-piperazin-1-yl)-rifamycin SV is dissolved in 50 ml of absolute ethanol. To this are added 200 mg of hydrogenated $PtO_2$, and the system is purged with hydrogen several times in vacuo. The reaction is carried out at room temperature under 1 atm for 14–18 hours. The colour of the solution changes from deep red to clear yellow. The system is subsequently purged in vacuo and under nitrogen and 500 mg of ascorbic acid are added. The catalyst is then removed by filtration through Celite, and the solution is evaporated. The yellow residue is then dissolved in 30 ml of water and extracted 3 times with 20 ml of ethyl acetate. The organic phase is washed with 30 ml of water, immediately dried with $MgSO_4$, filtered and evaporated. The residue is then suspended in 100 ml of boiling hexane, filtered, crystallized at 0° and dried. Obtained in this way is 16,17,18,19,28,29-hexahydro-8-O-pivaloyl-11-hydroxy-1-deoxy-11,15-dideoxo-1,15-oxy-3-(4-isobutyl-piperazin-1-yl)-rifamycin SV. 200 g of ascorbic acid in 10 ml of methanol are added to 400 mg of 16,17,18,19,28,29-hexahydro-8-O-pivaloyl-11-hydroxy-1-deoxy-11,15-deoxo-1,15-oxy-3(4-isobutyl-piperazin-1-yl)-rifamycin SV. The solution is stirred for 15 minutes and evaporated. The clear residue is dissolved in 10 ml of water, and 15 ml of a saturated NaCl solution are added dropwise and then 2.5 g of NaCl. The solution is stirred for 30 minutes and extracted 3 times with 10 ml of ethyl acetate. The organic phase is washed with 10 ml of a saturated NaCl solution, dried with $MgSO_4$, filtered through Celite and evaporated. The residue crystallizes from ethyl acetate/hexane 3/2. The hydrochloride is obtained in this way as beige crystals, melting point 175°–177°.

EXAMPLE 10

1.0 g of 16,17,18,19,28,29-hexahydro-8-O-pivaloyl-11-hydroxy-1-deoxy-11,15-dideoxo-1,15-oxy-3-(4-isobutyl-piperazin-1-yl)-rifamycin SV, obtained as in Example 1 for example, are dissolved in 20 ml of propionic anhydride. Then 1.0 g of sodium acetate is added, and the solution is stirred under nitrogen at room temperature for four hours and at 50° for one hour. The solution is filtered through Celite. The propionic anhydride is evaporated off in vacuo. The residue is dissolved in 10 ml of ethyl acetate. The organic phase is washed with 5 ml of 1N $NaHCO_3$, 5 ml of saturated NaCl solution, dried over $MgSO_4$, filtered and evaporated in vacuo. The residue is purified by chromatography ($SiO_2$, Chromatotron, 4 mm, hexane/ethyl acetate: 6/1 to 1:1) and by precipitation, where the residue is dissolved in 2 ml of methanol, and up to 50 ml of a methanol/water solution ½ are added. Filtration and drying result in 16,17,18,19,28,29-hexahydro-4-O-propionyl8-O-pivaloyl-11-propionyloxy-1-deoxy-11,15-dideoxo-1,15-oxy-3-(4-isobutyl-piperazin-1-yl)-rifamycin SV as a beige powder, melting point 129°–131°.

EXAMPLE 11

0.76 g of crude 16,17,18,19,28,29-hexahydro-8-O-pivaloyl-11-hydroxy-1-deoxy-11,15-dideoxo-1,15-oxy-3-(4-cyclohexylmethyl-piperazin-1-yl)-rifamycin SV is dissolved in 15 ml of propionic anhydride. The solution is stirred at 40° under nitrogen for 4 hours. The propionic anhydride is evaporated off in vacuo. The residue is dissolved in 15 ml of ethyl acetate. The organic phase is washed with 10 ml of 1N $NaHCO_3$, with saturated NaCl solution, dried over $MgSO_4$, filtered and evaporated in vacuo. The residue is purified by chromatography ($SiO_2$, 100 g, flash chromatography, hexane/acetone: 3:1) and by precipitation, where the residue is dissolved in 3 ml of methanol, and up to 30 ml of a stirred 1:1 methanol/water solution are added. Filtration and drying result in 16,17,18,19,28,29-hexahydro-4-O-propionyl-8-O-pivaloyl-11-propionyloxy-1-deoxy-11,15-dideoxo-1,15-oxy-3-(4-cyclohexylmethyl-piperazin-1-yl)-rifamycin SV of melting point 139°–141°.

The starting material can be prepared as follows, for example:

1 g of 8-O-pivaloyl-1-deoxy-15-deoxo-1,15-oxy-3-(4-cyclohexylmethyl-piperazin-1-yl)-rifamycin SV is dissolved in 50 ml of absolute ethanol. 200 ml of hydrogenated $PtO_2$ are added, and the system is purged with hydrogen several times in vacuo. The reaction is carried out at room temperature under 1 atm for 14–18 hours. The colour of the solution changes from deep red to clear yellow. The system is purged with nitrogen several times in vacuo. The catalyst is removed by filtration through Celite and the solution is evaporated. The residue is dissolved in 5 ml of methanol and stirred at 0° under nitrogen. The product crystallizes after a few minutes, is filtered through paper and dried. 16,17,18,19,28,29-hexahydro-8-O-pivaloyl-11-hydroxy-1-deoxy-11,15-dideoxo-1,15-oxy-3-(4-cyclohexylmethyl-piperazin-1-yl)-rifamycin SV is obtained in this way as a white powder.

EXAMPLE 12

0.5 g of crude 16,17,18,19,28,29-hexahydro-8-O-pivaloyl-11-hydroxy-1-deoxy-11,15-dideoxo-1,15-oxy-3-(4-cyclohexylmethyl-piperazin-1-yl)-rifamycin SV is dissolved in 10 ml of acetic anhydride. The solution is stirred under nitrogen at 40° for 4 hours. The acetic anhydride is evaporated off in vacuo. The residue is dissolved in 10 ml of ethyl acetate. The organic phase is washed with 5 ml of $NaHCO_3$, with 5 ml of saturated NaCl solution, dried over $MgSO_4$, filtered and evaporated in vacuo. The residue is purified by chromatography ($SiO_2$, 50 g, flash chromatography, hexane/ethyl acetate: 1:1) and by precipitation, where the residue is dissolved in 3 ml of methanol, and up to 30 ml of a stirred 1:1 methanol/water solution are added. Filtration and drying result in 16,17,18,19,28,29-hexahydro-4-O-acetyl-8-O-pivaloyl-11-acetyloxy-1-deoxy-11,15-dideoxo-1,15-oxy-3-(4-cyclohexylmethyl-piperazin-1-yl)-rifamycin SV of melting point 147°–149° as a white powder.

EXAMPLE 13

2 ml of acetic acid and 2.4 g of $PtO_2$ are added to a solution of 10 g of 8-O-pivaloyl-1-deoxy-15-deoxo-1,15-oxy-3-[4-(2,4,6-trimethylbenzyl)-piperazin-1-yl]rifamycin SV in 100 ml of ethyl acetate and 100 ml of acetic anhydride, and hydrogenation is carried out at room temperature and under 49 psi. After 53 hours, the catalyst is filtered off, and the residue is evaporated in vacuo. The crude product is purified by flash chromatography on silica gel with the eluent ethyl acetate/hexane 1:3 to 1:1. The amorphous purified product is crystallized from methanol/water. 16,17,18,19,28,29-hexahydro-4-O-acetyl-8-O-pivaloyl-11-acetyloxy-1-deoxy-11,15-dideoxo-1,15-oxy-3-[4(2,4,6-trimethylbenzyl)-piperazin-1-yl]-rifamycin SV are obtained in this way, melting point 150° (decomposition). MW: 1072.45 (found: MS).

EXAMPLE 14

A solution of 800 mg of 16,17,18,19,28,29-hexahydro-8-O-pivaloyl-11-hydroxy-1-deoxy-11,15-deoxo-1,15-oxy-3-[4-(2,4,6-trimethylbenzyl)-piperazin-1-yl]rifamycin SV in 20 ml of methylene chloride is cooled to 0° and 0.12 ml of triethylamine is added. Then a solution of 0.06 ml of methanesulfonyl chloride in 3 ml of methylene chloride is added dropwise while stirring. The mixture is stirred at room temperature for 15 hours, the solvent is then removed in vacuo, the residue is dissolved in ethyl acetate and extracted with saturated sodium bicarbonate solution and brine and dried over MgSO$_4$. The resulting 16,17,18,19,28,29-hexahydro-4-O-methanesulfonyl-8-O-pivaloyl-11-hydroxy-1-deoxy-11,15-dideoxo-1,15-oxy-3-[4-(2,4,6-trimethylbenzyl)-piperazin-1-yl]-rifamycin SV is purified by flash chromatography on silica gel using the eluent ethyl acetate/hexane 1:2, melting point 146°-150°. MW: 1066 (found: MS FAB).

The starting material can be prepared as follows, for example:

5 g of 8-O-pivaloyl-1-deoxy-15-deoxo-1,15-oxy-3-[4-(2,4,6-trimethylbenzyl)-piperazin-1-yl]-rifamycin SV are dissolved in 500 ml of ethanol and hydrogenated at room temperature under atmospheric pressure in the presence of g of PtO$_2$ and 0.7 g of sulfuric acid until 4 equivalents (460 ml) of hydrogen have been taken up. The catalyst is removed by filtration, aqueous sodium bicarbonate solution is used to neutralize, saturated brine is added, and the hydrogenation product is extracted by repeated shaking with ethyl acetate. After standing for some time, 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV crystallizes in pale brownish-red crystals which, after recrystallization from ether, form colourless plates and melt at 226°-227° (decomposition).

EXAMPLE 15

A solution of 400 mg of 8-O-pivaloyl-1-deoxy-15-deoxo-1,15-oxy-3-[2-methyl-4-(2,4,6-trimethylbenzyl)-piperazin-1-yl]-rifamycin SV (isomer A) in 8 ml of ethyl acetate, 8 ml of acetic anhydride and 1.6 ml of acetic acid is hydrogenated under 50 psi and at room temperature over PtO$_2$ for 4.5 hours. The catalyst is filtered off, and the residue is concentrated in vacuo. The resulting residue is purified by flash chromatography on silica gel with the eluent hexane/ethyl acetate 3:1.

16,17,18,19,28,29-Hexahydro-4-O-acetyl-8-O-pivaloyl-11-hydroxy-1-deoxy-11,15-dideoxo-1,15-oxy-3-[2-methyl-4-(2,4,6-trimethylbenzyl)-piperazin-1-yl]-rifamycin SV (isomer A) of melting point 146°-149° is obtained in this way.

The starting material can be prepared as follows, for example:

A solution of 1,8-di-O-pivaloyl-3-[2-methyl-4-(2,4,6-trimethylbenzyl)-piperazin-1-yl]rifamycin SV in 8 ml of 2-methoxyethanol is heated under nitrogen under reflux. After heating for 5 hours, the solvent is removed in vacuo. The crude product is purified by flash chromatography on silica gel and eluted with ethyl acetate/hexane 1:4 to 1:3. 8-OPivaloyl-1-deoxy-15-deoxo-1,15-oxy-3-[2-methyl-4-(2,4,6-trimethylbenzyl)-piperazin-1yl]-rifamycin SV is obtained in this way.

Isomer A (with respect to the methyl group on the piperazine ring) melting point 140° (decomposition); NMR (300 MHz, CD$_3$OD): 6.80 (s, 2H).

Isomer B (with respect to the methyl group on the piperazine ring) melting point 140° (decomposition); NMR (300 MHz, CD$_3$OD): 6.85 (s, 2H).

EXAMPLE 16

A solution of 400 mg of 8-O-pivaloyl-1-deoxy-15-deoxo-1,15-oxy-3-[2-methyl-4-(2,4,6-trimethylbenzyl)-piperazin-1-yl]-rifamycin SV (isomer B, see Example 15) in 8 ml of ethyl acetate, 8 ml of acetic anhydride and 1.6 ml of acetic acid is hydrogenated at room temperature under 45 psi over 80 mg of PtO$_2$ for 4 hours. The catalyst is filtered off, the filtrate is evaporated in vacuo, and the residue is purified by flash chromatography using hexane/ethyl acetate 3:1 to 2:1 as eluent. 16,17,18,19,28,29-Hexahydro-4-O-acetyl-8-O-pivaloyl-11-hydroxy-1-deoxy-11,15-dideoxo-1,15-oxy-3-[2-methyl-4-(2,4,6-trimethylbenzyl)-piperazin-1-yl]-rifamycin SV (isomer B) of melting point 147°-150° is obtained in this way.

EXAMPLE 17

In an analogous manner, for example as described in Example 13, starting from 8-O-pivaloyl-1-deoxy-15-deoxo-1,15-oxy-3-(4-cyclopentylmethyl-1-piperazinyl)-rifamycin SV, it is possible to prepare 16,17,18,19,28,29-hexahydro-4-O-acetyl-8-O-pivaloyl-11-hydroxy-1-deoxy-11,15-dideoxo-1,15-oxy-3-(4-cyclopentylmethyl-1-piperazinyl)rifamycin SV of melting point 148°-152°.

the starting material 8-O-pivaloyl-1-deoxy-15-deoxo-1,15-oxy-3-(4-cyclopentylmethyl-1-piperazinyl)-rifamycin SV can be prepared in an analogous manner, for example as described in Example 1.

EXAMPLE 18

In an analogous manner, for example as described in Example 13, it is possible to prepare 16,17,18,19,28,29-hexahydro-4-O-acetyl-8-O-pivaloyl-11-hydroxy-1-deoxy-11,15-dideoxo-1,15-oxy-3-[4-(2-cyclopentylethyl)-piperazin-1-yl]-rifamycin SV of melting point 130°-132°.

The starting material can be prepared in an analogous manner, for example as described in Example 1.

EXAMPLE 19

In an analogous manner, for example as described in Example 13, it is possible to prepare 16,17,18,19,28,29-hexahydro-4-O-acetyl-8-O-pivaloyl-11-acetyloxy-1-deoxy-11,15-dideoxo-1,15-oxy-3-(4-neopentyl-piperazin-1-yl)-rifamycin SV of melting point 123°-126°.

The starting material can be prepared in an analogous manner, for example as described in Example 1.

EXAMPLE 20

In an analogous manner, for example as described in Example 15, it is possible to prepare 16,17,18,19,28,29-hexahydro-4-O-acetyl-8-O-pivaloyl-11-acetyloxy-1-deoxy-11,15-dideoxo-1,15-oxy-3-(2-methyl-4-cyclohexylmethyl-piperazin-1-yl)-rifamycin SV (isomer A) of melting point 156°-158° and 16,17,18,19,28,29-hexahydro-4-O-acetyl8-O-pivaloyl-11-acetyloxy-1-deoxy-11,15dideoxo-1,15-oxy-3-(2-methyl-4-cyclohexylmethyl-piperazin-1-yl)-rifamycin SV (isomer B) of melting point 152°–156°.

EXAMPLE 21

A solution of 1 g of 8-O-pivaloyl-1-deoxy-15-deoxo-1,15-oxy-3-[4-(2,4,6-trimethylbenzyl)-piperazin-1-yl]-rifamycin SV in 20 ml of acetone is treated with 1.3 g of $K_2CO_3$ in 0.48 ml of dimethyl sulfate and heated under reflux. After three hours, the mixture is cooled, concentrated in vacuo and taken up in 40 ml of methylene chloride and 20 ml of water. The organic phase is washed with 20 ml of brine and dried with $MgSO_4$. The crude product is purified by flash chromatography on silica gel with the eluent ethyl acetate/hexane 1:2. 4-O-Methyl-8-O-pivaloyl-1-deoxy-15-deoxo-1,15-oxy-3-[4-(2,4,6trimethylbenzyl)-piperazin-1-yl]-rifamycin SV is obtained in this way as a yellow amorphous solid, melting point 157°–161°.

EXAMPLE 22

A solution of 0.5 g of 16,17,18,19,-tetrahydro-8-O-pivaloyl-1-deoxy-15-deoxo-1,15-oxy-3-[4-(2,4,6-trimethylbenzyl)-piperazin-1-yl]-rifamycin SV in 15 ml of acetone is treated with 0.57 g of $K_2CO_3$ and 0.1 g of dimethyl sulfate and heated under reflux. After 18 hours, the mixture is cooled, concentrated in vacuo and taken up in 20 ml of methylene chloride and 20 ml of water. The organic phase is washed with brine and dried over $MgSO_4$. The crude product is purified by flash chromatography on silica gel, eluting with ethyl acetate/hexane 1:3 via 1:2 to 2:1. The first main product, 16,17,18,19tetrahydro-4-O-methyl-8-O-pivaloyl-1-deoxy-15-deoxo-1,15-oxy-3-[4-(2,4,6trimethylbenzyl)-piperazin-1-yl]-rifamycin SV, isolated as a yellow amorphous solid, melting point 138°–140°.

EXAMPLE 23

0.5 g of $K_2CO_3$ and 0.1 ml of dimethyl sulfate are added to a stirred solution of 0.75 g of 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV in 10 ml of acetone. After stirring at 25° for 18 hours, the mixture is concentrated in vacuo and taken up in 20 ml of ethyl acetate and 10 ml of water. The organic phase is washed with brine and dried with $MgSO_4$. The crude product is purified by flash chromatography, eluting with ether/hexane 2:1 to 3:1. 16,17,18,19,28,29-Hexahydro-4-O-methyl-8-O-pivaloyl-11-hydroxy-1-deoxy-11,15-dideoxo-1,15-oxy-3-[4-(2,4,6-trimethylbenzyl)-piperazin-1-yl]-rifamycin SV is obtained in this way as a pale pink-coloured solid, melting point 140°–145°.

EXAMPLE 24

0.55 g of $K_2CO_3$ and 0.2 ml of dimethyl sulfate are added to a stirred solution of 1 g of 16,17,18,19,28,29-hexahydro-4-O-acetyl-8-O-pivaloyl-11-hydroxy-1deoxy-11,15-dideoxo-1,15-oxy-3-[4-(2,4,6-trimethylbenzyl)-piperazin-1-yl]-rifamycin SV in 20 ml of acetone. After stirring at 25° for 18 hours, the mixture is concentrated in vacuo and taken up in 50 ml of ethyl acetate and 20 ml of water. The organic phase is washed with brine and dried with $MgSO_4$. The crude product is purified by flash chromatography, eluting with ethyl acetate/hexane 1:2 to 1:1. 16,17,18,19,28,29-Hexahydro-4-O-methyl8-O-pivaloyl-11-acetyloxy-1-deoxy-11,15-dideoxo-1,15-oxy-3-[4-(2,4,6-trimethylbenzyl-piperazine-1-yl]-rifamycin SV is obtained in this way as a white amorphous solid, melting point 125°–130°.

EXAMPLE 25

A solution of 750 mg of 8-O-pivaloyl-1-deoxy-15-deoxo-1,15-oxy-3-[4-(2,4,6-trimethylbenzyl)-piperazin-1-yl]-rifamycin SV in 15 ml of acetone is treated with 420 mg of $K_2CO_3$ and 0.65 ml of ethyl iodide and heated under reflux. After 18 hours, the mixture is cooled, concentrated in vacuo and taken up in 40 ml of methylene chloride and 20 ml of water. The organic phase is washed with 20 ml of brine and dried with $MgSO_4$. The crude product is purified by flash chromatography, eluting with ethyl acetate/hexane 1:3 via 1:2 to 1:1. 4-O-Ethyl-8-O-pivaloyl-1-deoxy-15-deoxo-1,15-oxy-3-[4-(2,4,6trimethylbenzyl)-piperazin-1-yl]-rifamycin SV is obtained in this way as a yellow amorphous solid, melting point 154°–157°.

EXAMPLE 26

A solution of 750 mg of 8-O-pivaloyl-1-deoxy-15-deoxo-1,15-oxy-3-[4-(2,4,6-trimethylbenzyl)-piperazin-1-yl]-rifamycin SV in 15 ml of acetone is treated with 420 mg of $K_2CO_3$ and 0.23 ml of benzyl bromide and heated under reflux. After 4.5 hours, the mixture is cooled, concentrated in vacuo and taken up in 40 ml of methylene chloride and 20 ml of water. The organic phase is washed with 20 ml of brine and dried with $MgSO_4$. The crude product is purified by flash chromatography, eluting with ethyl acetate/hexane 1:3 to 1:2. 4-O-Benzyl-8-O-pivaloyl-11-hydroxy-1-deoxy-11,15-dideoxo-1,15-oxy-3-[4(2,4,6-trimethylbenzyl)-piperazin-1-yl]-rifamycin SV is obtained in this way as a yellow amorphous solid, melting point 142°–146°.

EXAMPLE 27

A solution of 0.5 g of 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV in 15 ml of acetone is treated with 0.28 g of $K_2CO_3$ and 0.5 ml of ethyl iodide and heated under reflux. After 24 hours, the mixture is cooled, concentrated in vacuo and taken up in 40 ml of methylene chloride and 20 ml of water. The organic phase is washed with 20 ml of brine and dried with $MgSO_4$. The crude product is purified by flash chromatography, eluting with ethyl acetate/hexane 1:2 to 1:3. 16,17,18,19,28,29Hexahydro-4-O-ethyl-8-O-pivaloyl-11-hydroxy-1-deoxy-11,15-dideoxo-1,15-oxy-3[4-(2,4,6-trimethylbenzyl)-piperazin-1-yl]-rifamycin SV is obtained in this way as an amorphous solid, melting point 122°–126°.

EXAMPLE 28

A solution of 0.5 g of 16,17,18,19,28,29-hexahydro-8-O-pivaloyl-11-hydroxy-1-deoxy-11,15-dideoxo-1,15-oxy-3-[4-(2,4,6-trimethylbenzyl)-piperazin-1-yl]-rifamycin SV in 15 ml of acetone is treated with 0.28 g of $K_2CO_3$ and 0.5 ml of benzyl bromide and heated under reflux. After 3 hours, the mixture is cooled, concentrated in vacuo and taken up in 40 ml of methylene chloride and 20 ml of water. The organic phase is washed with 20 ml of brine and dried with $MgSO_4$. The crude product is purified by flash chromatography, eluting with ethyl acetate/hexane 1:2 to 1:3. 16,17,18,19,28,29Hexahydro-4-O-benzyl-8-O-pivaloyl-11-hydroxy-1-deoxy-11,15-dideoxo-1,15-oxy3-[4-(2,4,6-trimethylbenzyl)-piperazin-1-yl]-rifamycin SV is obtained in this way as an amorphous solid, melting point 114°–118°.

EXAMPLE 29

A solution of 1 g of 8-O-pivaloyl-1-deoxy-15-deoxo-1,15-oxy-3-[4-(2,4,6-trimethylbenzyl)-piperazin-1-yl]-rifamycin SV in 20 ml of tetrahydrofuran and 20 ml of water is treated with 38 mg of NaBH$_4$ and stirred at 25° for 10 minutes. Then 1 ml of methanol is added and, after 10 minutes, the mixture is concentrated in vacuo and the solvent including water to remove. The yellow solid residue is taken up in 20 ml of acetone and treated with 0.42 g of K$_2$CO$_3$ and 0.2 ml of dimethyl sulfate and stirred. After 18 hours, the mixture is concentrated in vacuo and taken up in 40 ml of ethyl acetate and 10 ml of water. The organic phase is washed with 20 ml of brine, and with MgSO$_4$. The crude product is purified with flash chromatography on silica gel, eluting with ether/hexane 1:1. 4-O-Methyl-8-O-pivaloyl-11-hydroxy-1-deoxy-11,15-dideoxo-1,15-oxy-3-[4-(2,4,6trimethylbenzyl)-piperazin-1-yl]-rifamycin SV is obtained in this way as an amorphous brownish solid, melting point 175°–180°.

EXAMPLE 30

In an analogous manner, for example as described in one of the preceding examples, it is possible to prepare: 4-O-methyl-8-O-pivaloyl-11-hydroxy-1-deoxy-11,15-dideoxo-1,15-oxy-3-(4-cyclohexylmethyl-piperazin-1-yl)-rifamycin SV, mp 130°–134°. 16,17,18,19,28,29-Hexahydro-4-O-methyl-8-O-pivaloyl-11-hydroxy-1-deoxy-11,15-dideoxo-1,15-oxy-3-(4-cyclohexylmethyl-piperazin-1-yl)-rifamycin SV.

EXAMPLE 31

A mixture of 18 ml of propionic anhydride and 3 g of 8-O-pivaloyl-1-deoxy-15-deoxo-1,15-oxy-3-[4-(2,4,6-trimethylbenzyl)-piperazin-1-yl]-rifamycin SV is heated at 140° for 20 minutes. The excess propionic anhydride is removed in vacuo, and the crude product is purified by flash chromatography, using hexane:ethyl acetate 4:1 as eluent. 4-O-Propionyl-8-O-pivaloyl-1-deoxy-15-deoxo-1,15-oxy-3-[4-(2,4,6-trimethylbenzyl)piperazin-1-yl]-rifamycin SV of melting point 136°–139° is obtained in this way. It is possible in an analogous manner to prepare 4-O-acetyl-8-O-pivaloyl-1-deoxy-15-deoxo-1,15-oxy-3-[4-(2,4,6-trimethylbenzyl)-piperazin-1-yl]-rifamycin SV of melting point 156°–160°.

EXAMPLE 32

A solution of 10 ml of acetic anhydride and 1 g of 8-O-pivaloyl-1-deoxy-15-deoxo-1,15-oxy-3-[2-methyl-4-(2,4,6-trimethylbenzyl)-piperazin-1-yl]-rifamycin SV (isomer B) is heated at 140° for 20 minutes. The excess acetic anhydride is removed in vacuo, and the crude product is purified by flash chromatography, using hexane/ethyl acetate (from 3:1 via 2:1 to 1:1) as eluent. 4-O-Acetyl-8-O-pivaloyl-1-deoxy-15-deoxo-1,15-oxy-3-[2-methyl-4-(2,4,6-trimethylbenzyl)-piperazin-1-yl]-rifamycin SV of melting point 148°–152° is obtained in this way.

In an analogous manner, starting from the corresponding A-isomer, it is possible to prepare the corresponding isomer 4-O-acetyl-8-O-pivaloyl-1-deoxy-15-deoxo-1,15-oxy-3-[2-methyl-4-(2,4,6-trimethylbenzyl)-piperazin-1-yl]-rifamycin SV of melting point 145°–148°.

EXAMPLE 33

A solution of 1.0 g of 16,17,18,19,28,29-tetrahydro-8-O-pivaloyl-1-deoxy-15-deoxo-1,15-oxy-3-[4-(2,4,6-trimethylbenzyl)-piperazin-1-yl]-rifamycin SV in 20 ml of tetrahydrofuran and 0.5 ml of water is treated with 45 mg of NaBH$_4$ and stirred for 10 minutes at 25° followed by a quench with 1 ml of methanol. The mixture is concentrated in vacuo in order to remove the solvents including water. The residual yellow sold is taken up in 20 ml of acetone and treated with 690 mg of K$_2$CO$_3$ and 0.2 ml of dimethylsulphate and stirred. After 18 hours the mixture is concentrated in vacuo and taken up in 40 ml of ethylacetate and 10 ml of water. The organic phase is washed with 20 ml of brine and dried with MgSO$_4$. The crude product is purified with flash chromatography over silca gel eluating with ethylacetate/hexane 1:3. The product, 16,17,18,19-tetrahydro-4-O-methyl-8-O-pivaloyl-1-deoxy-11,15-dideoxo-1,15-oxy-11-hydroxy-3-[4-(2,4,6-trimethylbenzyl)-piperazin-1-yl]-rifamycin SV, cristallises in the form of colorless needles.

M.p. 255°–258°. $^1$NMR (300 MHz; DMSO, 80°): d 6,82 (s, 2H); 6,30 (d, 1H); 5,70 (s, 1H); 3,88 (s, 3H).

EXAMPLE 34

A solution of 5.0 g of 4-O-methyl-8-O-pivaloyl-1-deoxy-11,15-dideoxo-1,15-oxy-11-hydroxy-3-[4-(2,4,6-trimethylbenzyl)-piperazin-1-yl]-rifamycin SV in 200 ml of ethanol is hydrogenated in presence of 1 g of 10% Pd-C (Engelhard). After stirring for 18 hours the catalyst is filtered off and the solvent removed in vacuo. The crude product is cristallised from ethanol/water. Thus, 16,17,18,19-tetrahydro-4-O-methyl-8-O-pivaloyl-1-deoxy-11,15-dideoxo-1,15-oxy-11-hydroxy-3-[4-(2,4,6-trimethylbenzyl)-piperazin-1-yl]-rifamycin SV is isolated, m.p. 255°–258°.

EXAMPLE 35

A mixture of 3-(4-neopentylpiperazin-1-yl)-8-O-pivaloyl-1-deoxy-15-deoxo-1,15-oxy-rifamycin SV (700 mg) in tetrahydrofuran (25 ml) and water (3 ml) is treated with sodium borohydride (29 mg) under nitrogen. The color becomes pale yellow and after 5 min the reaction is quenched with acetone (5 ml). The mixture is concentrated to dryness at reduced pressure. The residue is dissolved in dimethylformamide (15 ml), degassed with nitrogen and treated with cesium carbonate (250 mg) followed by ethyl iodide (262 mg) under nitrogen. After 45 min stirring, it is quenched with ice-cold brine solution (50 ml) and extracted with ether. The ether extracts are washed with brine, dried over magnesium sulphate and concentrated to dryness at reduced pressure. The residue is flash chromatographed over silica with 2:1 hexane-ethyl acetate as eluent to give the pure product, 4-O-ethyl-11-hydroxy-3-(4-neopentyl-piperazin-1-yl)-8-O-pivaloyl-1-deoxy-11,15-dideoxo-1,15-oxy-rifamycin SV, mp 154°–157°.

The starting material can be prepared, for example, in the following manner: Bromine (0.63 ml) is added slowly to a mixture of rifamycin S (5 g), ethyl acetate (60 ml) and pyridine (1.74 ml) at −10° under nitrogen with stirring. After 2 hours at −5°, the solution is washed with 5% cold aqueous sodium thiosulphate (20×2 ml), then with cold water, dried over magnesium sulphate and filtered. The solution is treated at room temperature with 1-neopentyl-piperazine and triethylamine (1.2 ml). After 18.5 hours, the mixture is concentrated to dryness at reduced pressure to a dark residue, redissolved in ethyl acetate (100 ml), washed with saturated sodium bicarbonate solution, then with brine, dried over magnesium sulphate and concentrated to dryness at reduced pressure. The residue is chromatographed over silica with 3% methanol in methylene chloride as eluent to purify the desired 3-(4-neopentyl-piperazin-1-yl)-rifamycin S. This solid in methanol (80 ml) is treated with a solution of sodium ascorbate (3 g) in water (15 ml) and methanol (25 ml) dropwise over 40 minutes. It is concentrated to ca. 30 ml at reduced pressure, extracted with methylene chloride and the organic layer is dried over magnesium sulphate and concentrated to dryness at reduced pressure. The residual orange solid is dissolved in ethyl acetate, cooled to −20° and treated with 4-dimethyl-aminopyridine (13 mg) and pivaloyl chloride (0.5 ml). Triethylamine (0.7 ml) is added slowly at −20° and stirred 23 hours at −10°. It is treated with ethyl acetate (15 ml), pivaloyl chloride (0.25 ml) and triethylamine (0.35 ml) for 1 hour to remove all starting material. The mixture is quenched in water (30 ml) and stirred 10 minutes at ice temperature. The organic layer is washed with saturated sodium bicarbonate (30×2 ml), water (30 ml) and then brine and dried over magnesium sulphate to afford a solid. This is dissolved in 2-methoxyethanol (70 ml) and heated at reflux under nitrogen for 70 minutes. The mixture is concentrated to dryness at reduced pressure to afford the starting material mp 130°–140° dec.

EXAMPLE 36

When an equivalent amount of dimethylsulfate is used in place of ethyl iodide in Example 35, the product obtained is 4-O-methyl-11-hydroxy-8-O-pivaloyl-1-deoxy-11,15-dideoxo-1,15-oxy-3-(4-neopentylpiperazin-1-yl)-rifamycin SV.

EXAMPLE 37

A mixture of 3-(4-cyclohexylmethylpiperidin-1-yl)-8-O-pivaloyl-1-deoxy-15-deoxo-1,15-oxy-rifamycin SV (500 mg) and tetrahydrofuran (10 ml) cooled to −10° C. is treated with sodium borohydride (41 mg) in water (0.5 ml) under nitrogen. After 30 minutes at −10° to 0° C., the solvent is evaporated under vacuum and the residue is dissolved in acetone (15 ml) and treated with potassium carbonate (345 mg) and dimethyl sulphate (0.105 ml). After overnight stirring under nitrogen, the solvent is removed at reduced pressure and the residue partitioned between ethyl acetate (100 ml) and water (25 ml). The organic layer is washed with brine, dried over magnesium sulphate and concentrated to dryness at reduced pressure. The residue is flash chromatographed over silica gel with 1:2 ethyl acetate-hexane as eluent to afford 3-(4-cyclohexylmethylpiperidin-1-yl)-11-hydroxy-4-O-methyl-8-O-pivaloyl-1-deoxy-11,15-dideoxo-1,15-oxy-rifamycin SV, mp 112°–115°, [α]D= +435.6, c=3.2, CH$_2$Cl$_2$.

The starting material can be prepared, for example, in the following manner: To a solution of 3-(4-cyclohexyl-methylpiperidin-1-yl)-rifamycin SV (2.87 g, prepared as described by Traxler et al., J. Med. Chem. 1990, 552–560), methylene chloride (80 ml), triethylamine (1.25 ml) and 4-dimethylaminopyridine (20 mg) is added, with stirring under nitrogen at −5° to 0° C., pivaloyl chloride (1.08 ml). After 1 hour, the mixture is washed with water, then with brine, dried over magnesium sulphate and concentrated to dryness at reduced pressure. The residue is flash chromatographed over silica gel with ethyl acetate-hexane as eluent (1:2 followed by 3:5). Evaporation of the fractions containing only the desired material gives 1,8-di-O-pivaloyl-3-(4-cyclohexylmethylpiperidin-1-yl)-rifamycin SV, mp 165°–170°. This intermediate is dissolved in dl-1-methoxy-2-propanol (25 ml) and heated under nitrogen at 135° C. for 5.5 hours. The solvent is removed at reduced pressure and the residue chromatographed on silica gel with ethyl acetate-hexane as eluent (1:3 followed by 1:2). The desired fractions yield pure 3-(4-cyclohexylmethylpiperidin-1-yl)-8-O-pivaloyl-1-deoxy-15-deoxo-1,15-oxy-rifamycin SV as a pink solid, mp 122°–125°.

EXAMPLE 38

A solution of 4-O-methyl-8-O-pivaloyl-1-deoxy-15-deoxo-1,15-oxy-3-[4-(2,4,6-trimethylbenzyl)piperazin-1-yl]-rifamycin SV (150 mg) in tetrahydrofuran (2 ml) is treated with sodium borohydride (12 mg) and water (0.5 ml) under nitrogen. After 10 minutes at room temperature, more borohydride (24 mg) is added and stirring is continued for 30 minutes. The solvents are removed under vacuum and the residue partitioned between ethyl acetate and water. The organic layer is dried over magnesium sulphate and concentrated to dryness at reduced pressure to afford pure 11-hydroxy-4-O-methyl-8-O-pivaloyl-1-deoxy-11,15-dideoxo-1,15-oxy-3-[4-(2,4,6-trimethylbenzyl)-piperazin-1-yl]-rifamycin SV, mp 175°–180°, identical to the product of Example 29.

The starting material can be prepared, for example, in the following manner: A mixture of 8-O-pivaloyl-1-deoxy-15-deoxo-1,15-oxy-3-[4-(2,4,6-trimethylbenzyl)-piperazin-1-yl]-rifamycin SV (400 mg), 2,2-dimethoxypropane (10 ml), 10-camphorsulfonic acid (110 mg) and acetone (10 ml) is stirred overnight under nitrogen. The mixture is concentrated to dryness at reduced pressure and partitioned between ethyl acetate and saturated sodium bicarbonate solution. The organic layer is washed with brine, dried over magnesium sulphate and concentrated to dryness at reduced pressure to afford amorphous solid 21,23-di-O-isopropylidene-8-O-pivaloyl-1-deoxy-15-deoxo-1,15-oxy-3-[4-(2,4,6-trimethyl-benzyl)-piperazin-1-yl]-rifamycin SV (350 mg). This is dissolved in dimethylformamide (3 ml), cooled to 0° and treated with sodium hydride (20 mg, 60% in oil) under nitrogen. After 5 minutes at 0°–5°, the mixture is treated with dimethyl sulfate (0.04 ml) and stirred 1 hour at ambient temperature. The mixture is concentrated to dryness at reduced pressure and partitioned between ether and saturated sodium bicarbonate. The organic layer is washed with brine, dried over sodium sulphate and concentrated to dryness at reduced pressure. The residue is purified through a column of silica gel with 1:3 ethyl acetate-hexane as eluent to afford pure 21,23-di-O-isopropylidene-4-O-methyl-8-O-pivaloyl-1-deoxy-15-deoxo-1,15-oxy-3-[4-(2,4,6-trimethylbenzyl)-piperazin-1-yl]-rifamycin SV as an amorphous solid. The product (200 mg) in tetrahydrofuran (3 ml) is treated with 20% aqueous sulphuric acid (3 ml) at room temperature for 1 hour under nitrogen. The mixture is diluted with brine and extracted with ether. The ether extract is washed with saturated sodium bicarbonate and dried over sodium sulphate to afford the desired starting material as a yellow amorphous solid.

EXAMPLE 39

By the same sequence of reactions, 8-O-pivaloyl-1-deoxy-15-deoxo-1,15-oxy-3-(4-cyclohexylmethylpiperazin-1-yl)-rifamycin SV can be converted to 4-O-methyl-8-O-pivaloyl-1-deoxy-15-deoxo-1,15-oxy-3-(4-cyclohexylmethyl-piperazin-1-yl)-rifamycin SV, mp 115°–120°, and then similarly reduced with sodium borohydride to give 11-hydroxy-4-O-methyl-8-O-pivaloyl-1-deoxy-11,15-dideoxo-1,15-oxy-3-(4-cyclohexylmethylpiperazin-1-yl)-rifamycin SV, mp 130°–134°.

EXAMPLE 40

The product of Example 13, (150 mg) in ethanol (10 ml) is treated with maleic acid (150 mg) under stirring for several minutes and the mixture concentrated to dryness at reduced pressure to afford the maleate salt, mp 158°–160°, $[\alpha]D$ (25°) = +75.25 (c = 1.06, MeOH).

EXAMPLE 41

In the same manner as outlined in Examples 15 and 20, 3-[2-ethyl-4-(2,4,6-tri-methylbenzyl)-piperazin-1-yl]-8-O-pivaloyl-1-deoxy-15-deoxo-1,15-oxy-rifamycin SV, (isomer A), mp 125°–128°, is converted to 16,17,18,19,28,29-hexahydro-4-O-acetyl-11-acetoxy-3-[2-ethyl-4-(2,4,6-trimethylbenzyl)-piperazin-1-yl]-8-O-pivaloyl-1-deoxy-11,15-dideoxo-1,15-oxy-rifamycin SV, mp 152°–155°, MW: 1100 (found: MS); $C_{62}H_{89}N_3O_{14}$.

The starting material can be prepared, for example, in the following way: A mixture of 2-ethylpyrazine (15 g), platinum oxide (800 mg), ethanol (150 ml) and acetic acid (1.5 g) is hydrogenated at 45 psi for 8 hours at room temperature. It is filtered and the filtrate concentrated to an oil which is taken up in methylene chloride, treated with sodium carbonate for 0.5 hour, filtered and concentrated to dryness to white solid 2-ethylpiperazine, mp 56°–57°. The solid (0.8 g) in methylene chloride (15 ml) is treated with 2,4,6-trimethylbenzyl chloride (1.42 g) and triethylamine (2.4 ml) and stirred at reflux for 18 hours under nitrogen. The mixture is cooled, diluted with methylene chloride, washed with water, then with brine, dried over magnesium sulphate and concentrated to dryness to give an oil. This is taken up in ether, extracted into 3N hydrochloric acid and filtered free of solid which forms. The aqueous layer is made basic with cold 40% sodium hydroxide solution, extracted with methylene chloride, dried over magnesium sulphate and concentrated to dryness which gives 3-ethyl-1-(2,4,6-trimethylbenzyl)-piperazine as an oil which solidifies, mp 44°–45°. This amine (1.45 g) is dissolved in methylene chloride (40 ml), triethylamine (0.97 g) added, and the mixture is added dropwise under nitrogen to a solution of 3-bromorifamycin in methylene chloride (80 ml) and stirred 20 hours under nitrogen. The mixture is diluted with methylene chloride (100 ml), washed with saturated sodium bicarbonate, then with brine, dried over magnesium sulphate and concentrated to dryness at reduced pressure to a dark solid. This is flash chromatographed on silica gel with ethyl acetate-hexane as eluent (1:2, then 1:1). The first component from the column is collected and concentrated to a purple solid, mp 111°–114°. This fraction (1.2 g) in methanol (35 ml) is treated with sodium ascorbate (2.3 g) in a mixture of methanol (15 ml) and water (10 ml) under nitrogen for 1 hour. The solvent is evaporated at reduced pressure and the residue is concentrated to dryness to a yellow solid, mp 139°–142°. This material (1.19 g) is dissolved in methylene chloride (24 ml) under nitrogen, cooled to −20°, treated with 4-(N,N-dimethylamino)-pyridine (12 mg) and pivaloyl chloride (0.39 ml) and then, dropwise, treated with triethylamine (0.37 ml) under nitrogen. It is stirred at −17° to −5° over 1 hour, then treated further with pivaloyl chloride (0.39 ml) and triethylamine (0.37 ml) and stirred 1 hour at −5° to 0°. It is diluted with methylene chloride (60 ml), washed with saturated sodium bicarbonate solution, then with brine, dried over magnesium sulphate and concentrated to dryness at reduced pressure. The residue is chromatographed over silica gel with 2:1 hexane-ethyl acetate as eluent. The first component from the column, mp 162°–166°, (1.56 g), is added to dl-1-methoxy-2-propanol (15 ml) and heated under nitrogen at 125° for 4.5 hours. It is concentrated to dryness under high vacuum and chromatographed on silica gel with hexane-ethyl acetate as eluent (4:1, then 3:1, then 2:1). The first product from the column, mp 125°–128°, is the desired starting material.

EXAMPLE 42

The product from Example 29 (320 mg) in methanol (18 ml) is reacted with hydrazine hydrate (3 ml) under argon for 5 days at room temperature. It is treated cautiously with acetone, concentrated to dryness at reduced pressure and retreated with acetone in the same manner several times. The residue is taken up in ether and washed with dilute hydrochloric acid (pH 2–3). The ether solution is washed with water, dried over magnesium sulphate, concentrated to dryness at reduced pressure and flash chromatographed over silica gel with 1:3 ethyl acetate-hexane as eluent. The first product eluted is pure 25-deacetyl-11-hydroxy-4-O-methyl-8-O-pivaloyl-1-deoxy-11,15-dideoxo-1,15-oxy-3-[4-(2,4,6-trimethylbenzyl)-piperazin-1-yl]-rifamycin SV, mp 156°–160°.

EXAMPLE 43

A solution of 8-O-pivaloyl-3-[4-(2,4,6-trimethylbenzyl)piperazin-1-yl]-1-deoxy-15-deoxo-1,15-oxy-rifamycin SV (10 g) in tetrahydrofuran (150 ml) under nitrogen is treated with sodium borohydride (770 mg) in water (10 ml). After stirring at 0°–5° for 15 minutes, the reaction mixture is quenched with acetone (10 ml) and the solvent removed under water vacuum and the residue further dried under high vacuum. The residue is taken up in acetone (200 ml) and stirred under nitrogen with potassium carbonate (7 g) and dimethyl sulphate (1.5 ml) for 18 hours. The mixture is filtered and the filtrate concentrated to dryness at reduced pressure to give a dark residual solid. This is taken up in ethyl acetate (400 ml) washed with water (3×30 ml) then with brine and dried over magnesium sulphate. Evaporation of the solvent gives a yellow amorphous solid. It is dissolved in ethanol (60 ml) and treated with one equivalent of oxalic acid. The resulting solution is poured into water (600 ml) and the precipitate is collected and partitioned between ethyl acetate and saturated aqueous sodium bicarbonate. The organic layer is concentrated to a solid which is further purified by chromatography on silica gel with ethyl acetate-hexane as eluent (1:3 initially, then 1:2). Fractions containing only the desired product are concentrated to dryness to afford the 11-hydroxy-4-O-methyl-8-O-pivaloyl-3-[4-(2,4,6-trimethylbenzyl)piperazin-1-yl]-1-deoxy-11,15-dideoxo-1,15-oxy-rifamycin SV, m.p. 155°–160° (dec),

[α]D= +495.8°, c=0.9, CH$_2$Cl$_2$, as a white amorphous solid.

EXAMPLE 44

A mixture of 8-O-pivaloyl-1-deoxy-15-deoxo-1,15-oxy-3-[4-(2,4,6-trimethylbenzyl)piperazin-1-yl]-rifamycin SV (20 g), platinum oxide (1 g), acetic anhydride (100 ml), acetic acid (2 ml) and ethyl acetate (100 ml) is placed in a stirring Parr apparatus for hydrogenation. The reactor is filled with nitrogen at 40 psi, stirred and vented. It is then filled with hydrogen at 60 psi, stirred and vented. It is filled with hydrogen at 60 psi and stirred at 27°–32° for 24 hours. The mixture is cooled to room temperature, filtered through a celite bed on a filter paper and refiltered to remove all catalyst. The filtrate is concentrated at 60°/27 mm and the residual oil is taken up in ethyl acetate (100 ml), acetic acid (2 ml) and acetic anhydride (100 ml) and stirred at 60° for two hours. The mixture is concentrated at 60°/27 mm to a dark red oil, diluted with ethyl acetate (100 ml) and water (100 ml) with stirring. The mixture is treated with 50% aqueous sodium hydroxide (120 ml) at 25°–30°, saturated aqueous sodium chloride (60 ml) added and the organic layer collected. The organic extract is washed with saturated sodium chloride solution (2×100 ml), the combined aqueous layers re-extracted with ethyl acetate (100 ml) and the combined organic extract is dried over magnesium sulphate (10 g) and concentrated to dryness at reduced pressure to afford 16,17,18,19,28,29-hexahydro-4-O-acetyl-11-acetyloxy-8-O-pivaloyl-1-deoxy-11,15-dideoxo-1,15-oxy-3-[4-(2,4,6-trimethylbenzyl)-piperazin-1-yl]-rifamycin SV as an orange foam.

EXAMPLE 45

A mixture of maleic acid (0.9 g) and 16,17,18,19,28,29-hexahydro-4-O-acetyl-11-acetyloxy-8-O-pivaloyl-1-deoxy-11,15-dideoxo-1,15-oxy-3-[4-(2,4,6-trimethylbenzyl)-piperazin-1-yl]-rifamycin SV (8 g) is added to ethanol (32 ml) preheated to 40°–43°. All the material dissolves and it is slowly treated with water (54.2 ml) over a 20 minute period. The batch is seeded with crystals of the maleate salt obtained previously (0.5 g). More water (24.6 ml) is added slowly over 10 minutes and the turbid solution is cooled to room temperature over about 30 minutes. It is then stirred 2 hours while cooling the batch to about −10°. The crystalline material is collected by filtration, washed with cold (−10°) 50% aqueous ethanol (60 ml) and dried over 18 hours at approximately 20 mm pressure to afford the maleate salt as off-white crystals, m.p. 158°–160°, [α]D= +75.25°, (c=1.06, MeOH).

EXAMPLE 46

1-Deoxy-15-deoxo-1,15-oxy-3-[4-(2,4,6-trimethylbenzyl)-piperazin-1-yl]-4-O-methyl-21,23-isopropylidene-rifamycin SV (10.0 g, 10.5 mmol) and 4-dimethylaminopyridine (643 mg, 5.3 mmol) are dissolved in CH$_2$Cl$_2$ (100 ml) and stirred, under nitrogen, at room temperature. Triethylamine (7.3 ml, 52.5 mmol) is added followed by dimethylcarbamyl chloride (1.45 ml, 15.9 mmol). The mixture is warmed to 40° for 4 hours and then stirred at room temperature for an additional 48 hours. The reaction is diluted with 1:1 Et$_2$O, EtOAc, and washed with water (100 ml), then saturated aqueous NaHCO$_3$ (2×100 ml) and finally brine (100 ml). The filtered solution is concentrated to dryness and then chromatographed on silica-gel using a 7:3 Et$_2$O, pentane eluant to give a yellow solid. The solid is dissolved in tetrahydrofuran (200 ml) and cooled to 0°. Aqueous 20% H$_2$SO$_4$ (5 ml) is added and the reaction stirred for 30 minutes. The reaction is partitioned, in a separatory funnel, between 1:1 Et$_2$O, EtOAc (400 ml) and saturated aqueous NaHCO$_3$ (400 ml). The organic layer is washed with brine (250 ml), dried (MgSO$_4$), filtered and evaporated to dryness. The crude product is chomatographed on a silica-gel column using a 5:1:1 Et$_2$O, CH$_2$Cl$_2$, n-pentane eluant. Upon evaporation 8-O-dimethylcarbanyl-1-deoxy-15-deoxo-1,15-oxy-3-[4-(2,4,6-trimethylbenzyl)-piperazin-1-yl]-4-O-methyl-rifamycin SV is isolated as a yellow-orange solid (mp 153°–7°).

The starting material can be prepared, for example as follows:

8-O-Pivaloyl-1-deoxy-15-deoxo-1,15-oxy-3-[4-(2,4,6-trimethylbenzyl)-piperazin-1-yl]-rifamycin SV (25 g, 25.5 mmol) is dissolved in 2,2-dimethoxypropane (130 ml, 1.1 mol). A solution of (+)-camphor sulfonic acid (9.0 g, 38.7 mmol) in acetone (130 ml, 1.8 mol) is added and the mixture warmed to 45° C. for 2 hours. The reaction is cooled to room temperature and the volatiles are removed. The resulting red solid is dissolved in CH$_2$Cl$_2$ (500 ml), transferred to a separatory funnel, and washed with saturated aqueous Na$_2$CO$_3$ (2×300 ml), followed by brine (200 ml). The organic solution is dried with MgSO$_4$, filtered and then evaporated to give 8-O-pivaloyl-1-deoxy-15-deoxo-1,15-oxy-3-[4-(2,4,6-trimethylbenzyl)-piperazin-1-yl]-21,23-isopropylidene-rifamycin SV as a dark red solid (mp 148°–150°).

A dispersion of 55% sodium hydride in mineral oil (1.34 g, 30.6 mmol) is washed, in a nitrogen atmosphere, with hexane (2×200 ml) to remove the oil. The hexanes are decanted and the NaH is suspended in dimethylformamide (DMF) (75 ml). 8-O-Pivaloyl-1-deoxy-15-deoxo-1,15-oxy-3-[4-(2,4,6-trimethylbenzyl)-piperazin-1-yl]-21,23-isopropylidine-rifamycin SV (25.0 g, 24.5 mmol) is dissolved in DMF (125 ml) and added dropwise to the stirred NaH suspension at 0°. The solution is kept between 0° and 5° for 30 minutes during which time the color is observed to change from deep red to dark blue. Dimethyl sulfate (3.86 g, 30.6 mmol) is added in one portion and the reaction mixture stirred at 15° for 2 hours. After warming to room temperature, ammonium chloride (5 g) is added and the reaction mixture becomes an orange color. The reaction is transferred to a separatory funnel and diluted with 1 liter of 4:1 Et$_2$O, EtOAc. The organic solution is washed with 1M NH$_4$Cl (400 ml), then NaHCO$_3$ (400 ml), then water (2×400 ml) and finally brine (400 ml). The solution is dried with MgSO$_4$, filtered and concentrated to dryness. The resulting orange solid, 8-O-pivaloyl-1-deoxy-15-deoxy-1,15-oxy-3-[4-(2,4,6-trimethylbenzyl)-piperazin-1-yl]-4-O-methyl-21,23-isopropylidene-rifamycin SV (mp 118°–22°) is used directly or can be chromatographed on a silica gel column using a 4:1 hexanes, EtOAc as eluant.

8-O-Pivaloyl-1-deoxy-15-deoxo,1,15-oxy-3-[4-(2,4,6-trimethylbenzyl)-piperazin-1-yl]-4-O-methyl-21,23-isopropylidene-rifamycin SV (20.0 g, 19.3 mmol) is dissolved in absolute ethanol (900 ml). A solution of sodium cyanide (2.5 g, 38.5 mmol) in water (100 ml) is added and the mixture heated to reflux temperature for 2 hours. After cooling to room temperature, the solution is evaporated to give a brown-orange solid. The residue is dissolved in 1 liter of 1:1 Et$_2$O, EtOAc and washed with saturated aqueous NaHCO$_3$ (3×500 ml), then brine (250 ml) and dried with MgSO$_4$. The filtered solution is concentrated and then dissolved to a silica-gel chromatography column. The column is eluted with 1:1:1 Et$_2$O, CH$_2$Cl$_2$, hexanes to give, upon evaporation, 1-deoxy-15-deoxo-1,15-oxy-3-[4-(2,4,6-trimethylbenzyl)-piperazin-1-yl]-4-O-methyl-21,23-isopropylidene-rifamycin SV as an orange solid. The product can be recrystallized from n-heptane to give a bright yellow crystalline material (mp 161°-3°).

EXAMPLE 47

8-O-Dimethylcarbamyl-1-deoxy-15-deoxo-1,15-oxy-3-[4-(2,4,6-trimethylbenzyl)-piperazin-1-yl]-4-O-methyl-rifamycin SV (7.5 g, 7.6 mmol) is dissolved in tetrahydrofuran (THF) (150 ml) and cooled to 15°. LiBH$_4$ in THF (3.8 ml of 2M solution, 7.6 mmol) is added dropwise to the stirred reaction mixture and the color changes from orange to light yellow. The solution is transferred to a separatory funnel, diluted with 1:1 Et$_2$O, EtOAc (500 ml), washed with saturated aqueous NaHCO$_3$ (2×500 ml) and then brine (300 ml). The solution is dried (MgSO$_4$), filtered and concentrated. The crude product is purified by silica-gel column chromatography using a 16:3:1 n-pentane, CH$_2$Cl$_2$, EtOH eluant to give 8-O-dimethylcarbamyl-1-deoxy-11,15-dideoxo-1,15-oxy-3-[4-(2,4,6-trimethylbenzyl)-piperazin-1-yl]-11-hydroxy-4-O-methyl-rifamycin SV as a cream-colored solid (mp 155°-165° dec.)

EXAMPLE 48

1-Deoxy-15-deoxo-1,15-oxy-3-[4-(2,4,6-trimethylbenzyl)-piperazin-1-yl]-4-O-methyl-21,23-isopropylidene-rifamycin SV (1.5 g, 1.58 mmol), 1-methyl-1-cyclohexanecarboxylic acid (225 mg, 1.58 mmol) and 4-dimethylaminopyridine (96 mg, 0.79 mmol) are dissolved in CH$_2$Cl$_2$ and placed under a nitrogen atmosphere. 1-(3-Dimethylaminopropyl)-3-ethylcarbodiimide hydrochloride (605 mg, 3.17 mmol) is added and the reaction stirred, at room temperature, for 48 hours. The solution is transferred to a separatory funnel and diluted with 1:1 Et$_2$O, EtOAc (250 ml). The organic layer is washed with water (3×200 ml) and then brine (150 ml), dried (MgSO$_4$), filtered and concentrated to dryness. The residue is subjected to column chromatography on silica-gel using a 2:1 hexanes, Et$_2$O eluant. The resulting orange solid is dissolved in tetrahydrofuran (200 ml) and cooled to 0°. Aqueous 20% H$_2$SO$_4$ (5 ml) is added and the reaction stirred for 30 minutes. The reaction is partitioned, in a separatory funnel, between 1:1 Et$_2$O, EtOAc (400 ml) and saturated aqueous NaHCO$_3$ (400 ml). The organic layer is washed with brine (250 ml), dried (MgSO$_4$), filtered and evaporated to dryness. The crude product is chromatographed on a silica-gel column using a 2:1 Et$_2$O, n-pentane eluant. Upon evaporation 8-O-(1-methyl-1-cyclohexane-carbonyl)-1-deoxy-15-deoxo-1,15-oxy-3-[4-(2,4,6-trimethylbenzyl)-piperazin-1-yl]-4-O-methyl-rifamycin SV is isolated as a yellow solid (mp 145°-150°).

EXAMPLE 49

(a) In a way analogously as described in example 46, 8-O-(2,6-dimethylbenzoyl)-1-deoxy-15-deoxo-1,15-oxy-3-[4-(2,4,6-trimethylbenzyl)-piperazin-1-yl]-4-O-methyl-rifamycin SV (mp 153°-160°) is prepared using 2,6-dimethylbenzoyl chloride in place of the carbamyl chloride.

(b) In a way analogously as described in example 46, 8-O-(4-biphenylcarbonyl)-1-deoxy-15-deoxo-1,15-oxy-3-[4-(2,4,6-trimethylbenzyl)-piperazin-1-yl]-4-O-methyl-rifamycin SV (mp 154°-161°) is prepared using 4-biphenylcarbonyl chloride in place of the carbamyl chloride.

(c) In a way analogously as described in example 46, 8-O-(4-morpholinocarbonyl-1-deoxy-15-deoxo-1,15-oxy-3-[4-(2,4,6-trimethylbenzyl)-piperazin-1-yl]-4-O-methyl-rifamycin SV (mp 154°-159°) is prepared using 4-morpholino-carbonyl-chloride in place of the carbamyl chloride.

(d) In a way analogously as described in example 47, 8-O-(4-biphenylcarbonyl)-1-deoxy-11,15-dideoxo-1,15-oxy-3-[4-(2,4,6-trimethylbenzyl)-piperazin-1-yl]-11-hydroxy-4-O-methyl-rifamycin SV is prepared (mp 72°-7°).

(e) In a way analogously as described in example 47, 8-O-(2,6-dimethylbenzoyl)-1-deoxy-11,15-dideoxo-1,15-oxy-3-[4-(2,4,6-trimethylbenzyl)-piperazin-1-yl]-11-hydroxy-4-O-methyl-rifamycin SV (mp 168°-173°) is prepared.

(f) In a way analogously as described in example 47, 8-O-(4-morpholinocarbonyl)-1-deoxy-11,15-dideoxo-1,15-oxy-3-[4-(2,4,6-trimethylbenzyl)-piperazin-1-yl]-11-hydroxy-4-O-methyl-rifamycin SV (mp 150°-160°) is prepared.

(g) In a way analogously as described in example 47, 8-O-[1-(2-methoxy-2,2-dimethylacetyl)]-1-deoxy-11,15-dideoxo-1,15-oxy-3-[4-(2,4,6-trimethylbenzyl)-piperazin-1-yl]-11-hydroxy-4-O-methyl-rifamycin SV (mp 150°-5°) is prepared.

(h) In a way analogously as described in example 48, 8-O-[1-(2-methoxy-2,2-dimethylacetyl)]-1-deoxy-15-deoxo-1,15-oxy-3-[4-(2,4,6-trimethylbenzyl)-piperazin-1-yl]-4-O-methyl-rifamycin SV (mp 135°-140°) is prepared using 2-methoxy-2,2-dimethylacetic acid in place of 1-methyl-1-cyclohexanecarboxylic acid.

(i) In a way analogously as described in example 48, 8-O-[1-(2-adamantylcarbonyl)]-1-deoxy-15-deoxo-1,15-oxy-3-[4-(2,4,6-trimethylbenzyl)-piperazin-1-yl]-4-O-methyl-rifamycin SV (mp 190°-2°) is prepared using 1-adamantanecarboxylic acid in place of 1-methyl-1-cyclohexanecarboxylic acid.

(j) In a way analogously as described in example 48, 8-O-[1-(2-N,N-dimethylamino-2,2-dimethylacetyl)]-1-deoxy-15-deoxo-1,15-oxy-3-[4-(2,4,6-trimethylbenzyl)-piperazin-1-yl]-4-O-methyl-rifamycin SV (mp 171°-4°) is prepared using 2-N,N-dimethylamino-2,2-dimethylacetic-acid in place of 1-methyl-1-cyclohexanecarboxylic acid.

(k) In a way analogously as described in example 46, 8-)-t-butylcarbamyl-1-deoxy-15-deoxy-1,15-oxy-3-[4-(2,4,6-trimethylbenzyl)-piperazin-1-yl]-4-O-methyl-rifamycin (m.p. 202°-204°) SV, can be prepared using t-butyl isocyanate instead of dimethylcarbamyl chloride.

EXAMPLE 50

8-O-Pivaloyl-1-deoxy-15-deoxo-1,15-oxy-3-(4-neopentyl-piperazin-1-yl)-rifamycin SV (12.3 g, 13.4 mmol) is dissolved in N,N-dimethylformamide (DMF) (250 ml) and stirred at room temperature. NaBH$_4$ is added (0.5 g, 13.2 mmol) to the stirred reaction mixture and the color changes from red to orange. Cesium carbonate (13.0 g, 39.9 mmol) and diethyl sulfate (4.13 g, 26.8 mmol) are added and the reaction mixture is stirred for 4 hours. The solution is transferred to a separatory funnel, diluted with 1:1 Et$_2$O, EtOAc (1500 ml) and washed with brine (3×1500 ml). The solution is dried (MgSO$_4$), filtered and concentrated. The crude product is purified by silica-gel column chromatography using a 2:1, EtOAc, hexane eluant to give 8-O-pivaloyl-1-deoxy-11,15-dideoxo-1,15-oxy-3-[4-neopentyl-piperazin-1-yl]-11-hydroxy-4-O-ethyl-rifamycin SV as a cream-colored solid (mp 158°-161°).

The starting material can be prepared, for example as follows:

Rifamycin S (48.0 g, 69.0 mmol) is dissolved in ethyl acetate (350 ml) in a round-bottom flask. A solution of pyridine (60 ml, 0.74 mol) in methylene chloride (100 ml) is added and the stirred mixture is cooled to −10°. Bromine (12.2 g, 76 mmol) is added dropwise as a solution in CH$_2$Cl$_2$ and the reaction is stirred at −10° for 30 minutes. The reaction mixture is transferred to a separatory funnel containing pre-chilled (0°) 2:1 Et$_2$O and EtOAc (1500 ml), washed with pre-chilled (0°) brine (3×500 ml) and pre-chilled (0°) saturated aqueous Na$_2$S$_2$O$_3$ (3×500 ml). The organic solution is dried (MgSO$_4$), filtered and transferred to a separatory funnel. A solution of neopentylpiperazine (11.8 g, 75.5 mmol) in CH$_2$Cl$_2$ (60 ml) and triethylamine (60 ml) is added and the solution is mixed by shaking. The organic layer is washed with water (3×500 ml) and brine (500 ml), then dried (MgSO$_4$), filtered and concentrated to dryness. Residual solvent is then removed under high vacuum. The residue is dissolved in toluene (600 ml) and silica-gel (260 g) is added. The suspension is stirred for 1 hour and then filtered using a Buchner funnel. The silica-gel is washed by passing 5:1 Et$_2$O, toluene (2000 ml) and EtOAc (1500 ml) through the filter cake. The combined filtrates are concentrated to give 3-(4-neopentyl-piperazin-1-yl)-rifamycin SV as a purple solid.

3-(4-neopentyl-piperazin-1-yl)-rifamycin SV (41.8 g, 49.0 mmol) is dissolved in toluene (400 ml) in a separatory funnel. A solution of triethylamine (35 ml, 0.25 mol) in toluene (200 ml) is added followed by a solution of 4-dimethylaminopyridine (6.0 g, 48.8 mmol) in toluene (200 ml). The funnel is shaken to mix thoroughly. Trimethylacetyl chloride (13.0 g, 107.8 mmol) is added as a solution in toluene (200 ml) and the reaction is mixed by shaking for 5 minutes. The solution is washed with brine (4×200 ml), dried with MgSO$_4$ and then filtered. The reaction mixture is transferred to a round-bottom flask and heated to reflux temperature for 45 minutes. The reaction is cooled to room temperature and flash silica-gel (400 g) is added. The suspension is stirred for 30 minutes and then filtered using a Buchner funnel. The silica-gel is washed by passing 1:1 Et$_2$O, EtOAc (2500 ml) through the filter cake. The combined filtrates are concentrated to give 8-O-pivaloyl-1-deoxy-15-deoxo-1,15-oxy-3-(4-neopentyl-piperazin-1-yl)-rifamycin SV as a dark red solid (m.p. 130°-140°).

EXAMPLE 51

Capsules containing 250 mg of active compound, for example the compound of the formula I in which the structural elements —A$_1$—A$_2$—, —A$_3$—A$_4$— and —A$_5$—A$_6$— each denote ethylene, X represents >N—, alk denotes methylene, R$_1$ denotes pivaloyl, R$_2$ denotes acetyl, R$_3$, R$_3'$ and R$_7$ each denote hydrogen, R$_4$ denotes 2,4,6-trimethylphenyl and R$_5$ is acetyl can be prepared as follows:

| Composition (for 1000 capsules): | |
|---|---|
| Active Compound | 250.0 g |
| Maize starch | 50.0 g |
| Polyvinylpyrrolidone | 15.0 g |

| -continued | |
|---|---|
| Composition (for 1000 capsules): | |
| Magnesium stearate | 5.0 g |
| Ethanol | q.s. |

The active compound and the maize starch are mixed and moistened with a solution of polyvinylpyrrolidone in 50 g of ethanol. The moist composition is forced through a screen with a mesh width of 3 mm and dried at 45°. The dry granules are screened through a screen with a mesh width of 1 mm and mixed with 5 g of magnesium stearate. The mixture is dispensed in 0.320 g portions into size 0 two-piece capsules.

It is also possible in an analogous manner to use the other compounds prepared as in the preceding examples as active compound component.

We claim:

1. A compound of the formula I

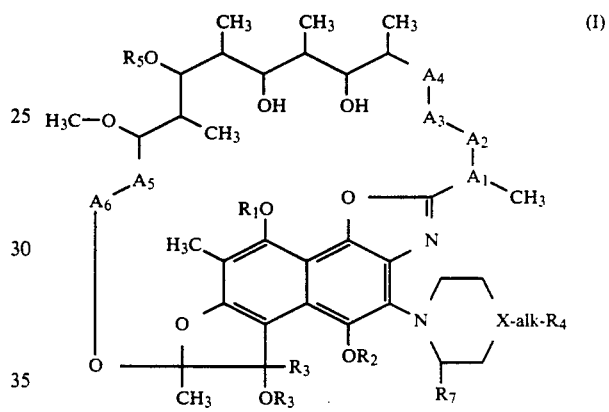

in which —A$_1$—A$_2$—, —A$_3$—A$_4$— and —A$_5$—A$_6$— each denote ethylene or vinylene, or the elements —A$_1$—A$_2$— and —A$_3$—A$_4$— each denote ethylene and —A$_5$—A$_6$— denotes vinylene; X represents >C(R$_6$)— or >N—, and R$_6$ denotes hydrogen or C$_1$-C$_7$alkyl; alk denotes C$_1$-C$_7$alkylene, C$_3$-C$_7$alkenylene or C$_3$-C$_7$alkynylene; R$_1$ denotes C$_2$-C$_8$alkanoyl, halogen-C$_2$-C$_8$alkanoyl, alkoxy-C$_2$-C$_8$-alkanoyl, phenyl- or naphthyl-C$_2$-C$_8$alkanoyl, benzoyl, naphthoyl, 5- or 6-membered monocyclic monoaza-, monooxa- or monothiaaroyl, C$_1$-C$_7$alkoxycarbonyl, phenyl- or naphthyl-C$_1$-C$_7$alkoxy-carbonyl, aminocarbonyl which is unsubstituted or mono- or di-substituted by C$_1$-C$_7$alkyl, C$_1$-C$_7$alkanesulfonyl, halogeno-C$_1$-C$_7$alkanesulfonyl, phenyl- or naphthyl-C$_1$-C$_7$alkanesulfonyl, C$_3$-C$_7$cycloalkanesulfonyl or benzene- or naphthylsulfonyl; R$_2$ denotes C$_2$-C$_8$alkanoyl, halogeno-C$_2$-C$_8$alkanoyl, phenyl- or naphthyl-C$_2$-C$_8$alkanoyl, benzoyl, naphthoyl, 5- or 6-membered monocyclic monoaza aroyl, 5-membered monocyclic monooxa- or monothiaaroyl, C$_1$-C$_7$alkoxycarbonyl, phenyl- or naphthyl-C$_1$-C$_7$alkoxy-carbonyl, aminocarbonyl which is unsubstituted or mono- or disubstituted by C$_1$-C$_7$alkyl, or C$_1$-C$_7$alkanesulfonyl, halogeno-C$_1$-C$_7$alkanesulfonyl, phenyl- or naphthyl-C$_1$-C$_7$alkanesulfonyl, C$_3$-C$_7$cycloalkanesulfonyl or benzene- or naphthylsulfonyl, C$_1$-C$_7$alkyl, phenyl- or naphthyl-C$_1$-C$_7$alkyl; R$_3$ and R$_3'$ represent a common bond, or R$_3$ denotes hydrogen or C$_2$-C$_8$alkanoyl, halogeno-C$_2$-C$_8$alkanoyl, phenyl- or naphthyl-C$_2$-C$_8$alkanoyl, benzoyl, naphthoyl, 5- or 6-membered monocyclic monoaza aroyl, 5-membered monocyclic monooxa- or monothiaaroyl, $C_1$-$C_7$alkoxycarbonyl, phenyl- or naphthyl-$C_1$-$C_7$alkoxy-carbonyl, aminocarbonyl which is unsubstituted or mono- or di-substituted by $C_1$-$C_7$alkyl, or $C_1$-$C_7$alkanesulfonyl, halogeno-$C_1$-$C_7$alkanesulfonyl, phenyl- or naphthyl-$C_1$-$C_7$alkanesulfonyl, $C_3$-$C_7$cycloalkylsulfonyl or benzene- or naphthylsulfonyl, and $R_3'$ is hydrogen; $R_4$ denotes hydrogen, $C_3$-$C_7$-cycloalkyl, phenyl, biphenylyl or naphthyl; $R_5$ denotes hydrogen or acetyl; $R_7$ denotes hydrogen or $C_1$-$C_7$alkyl; where the aromatic radicals in each case are unsubstituted or substituted one, two or three times by substituents selected from the group consisting of halogen, $C_1$-$C_7$alkyl, $C_1$-$C_7$alkoxy, hydroxyl, $C_2$-$C_8$alkanoyloxy, trifluoromethyl and nitro; or a pharmaceutically acceptable salt thereof.

2. A compound according to claim 1 of the formula I in which —$A_1$—$A_2$—, —$A_3$—$A_4$—, —$A_5$—$A_6$— and $R_5$ have the indicated meanings; X represents >$C(R_6)$— or >N—, and $R_6$ is hydrogen; alk denotes $C_1$-$C_7$alkylene, $C_3$-$C_7$alkyeylene or $C_3$-$C_7$alkynylene; $R_1$, $R_2$ and $R_3$, independently of one another, denote $C_2$-$C_8$alkanoyl, halogeno-$C_2$-$C_8$alkanoyl, phenyl- or naphthyl-$C_2$-$C_8$alkanoyl, benzoyl, naphthoyl, 5- or 6-membered monocyclic monoaza-, monooxa- or monothiaaroyl, $C_1$-$C_7$alkoxycarbonyl, phenyl- or naphthyl-$C_1$-$C_7$alkoxy-carbonyl, aminocarbonyl which is unsubstituted or mono- or di-substituted by $C_1$-$C_7$alkyl, or $C_1$-$C_7$alkanesulfonyl, halogeno-$C_1$-$C_7$alkanesulfonyl, $C_3$-$C_7$cycloalkanesulfonyl or benzene- or naphthylsulfonyl, and $R_1$ additionally and $R_3'$ and $R_7$ denote hydrogen; $R_4$ denotes hydrogen, $C_3$-$C_7$cycloalkyl, phenyl, biphenylyl or naphthyl; where the aromatic radicals are in each case unsubstituted or substituted one, two or three times by substituents selected from the group consisting of halogen, $C_1$-$C_7$alkyl, $C_1$-$C_7$alkoxy, hydroxyl, $C_2$-$C_8$alkanoyloxy, trifluoromethyl and nitro; or a pharmaceutically acceptable salt thereof.

3. A compound according to claim 1 of the formula I in which —$A_1$—$A_2$—, —$A_3$—$A_4$—, —$A_5$—$A_6$— and $R_5$ have the indicated meanings; X represents >$C(R_6)$— or >N—, and $R_6$ is hydrogen; alk denotes $C_1$-$C_7$alkylene, $C_3$-$C_7$alkenylene or $C_3$-$C_7$alkynylene, where the multiple bonds are located in a position higher than α to the piperazine nitrogen; $R_1$ denotes $C_2$-$C_8$alkanoyl, phenyl-$C_2$-$C_6$alkanoyl, benzoyl, $C_1$-$C_7$alkoxy-carbonyl, phenyl-$C_1$-$C_4$alkoxycarbonyl, $C_1$-$C_4$alkanesulfonyl or benzenesulfonyl; $R_2$ denotes $C_2$-$C_8$alkanoyl, phenyl-$C_2$-$C_6$alkanoyl, $C_1$-$C_7$alkoxy-carbonyl, phenyl-$C_1$-$C_4$alkoxycarbonyl, $C_1$-$C_4$alkanesulfonyl or benzenesulfonyl, $C_1$-$C_7$alkyl or phenyl-$C_1$-$C_4$alkyl; $R_3$ and $R_3'$ together represent a bond; or $R_3$ denotes hydrogen, $C_2$-$C_8$alkanoyl, phenyl-$C_2$-$C_6$alkanoyl, benzoyl, $C_1$-$C_7$alkoxy-carbonyl, phenyl-$C_1$-$C_4$alkoxycarbonyl, $C_1$-$C_4$alkanesulfonyl or benzenesulfonyl, and $R_3'$ is hydrogen; $R_4$ denotes hydrogen, $C_3$-$C_7$cycloalkyl, phenyl, biphenylyl or naphthyl; $R_7$ denotes hydrogen or $C_1$-$C_7$alkyl; where the aromatic radicals in each case are unsubstituted or substituted one, two or three times by substituents selected from the group consisting of halogen, $C_1$-$C_7$alkyl, $C_1$-$C_7$alkoxy, hydroxyl, $C_2$-$C_8$alkanoyloxy, trifluoromethyl and nitro; or a pharmaceutically acceptable salt thereof.

4. A compound according to claim 1 of the formula I in which —$A_1$—$A_2$—, —$A_3$—$A_4$—, —$A_5$—$A_6$— and $R_5$ have the indicated meanings; X represents >$C(R_6)$— or >N—, and $R_6$ is hydrogen; alk denotes $C_1$-$C_7$alkylene, $C_3$-$C_7$alkenylene or $C_3$-$C_7$alkynylene, where the multiple bonds are located in a position higher than α to the piperazine nitrogen; $R_1$, $R_2$ and $R_3$, independently of one another, denote $C_2$-$C_8$alkanoyl, phenyl-$C_2$-$C_6$alkanoyl, $C_1$-$C_7$alkoxy-carbonyl, phenyl-$C_1$-$C_4$alkoxycarbonyl, $C_1$-$C_4$alkanesulfonyl or benzenesulfonyl; and $R_3'$ and $R_7$ denote hydrogen; $R_4$ denotes hydrogen, $C_3$-$C_7$cycloalkyl, phenyl, biphenylyl or naphthyl; where the aromatic radicals in each case are unsubstituted or substituted one, two or three times by substituents selected from the group consisting of halogen, $C_1$-$C_7$alkyl, $C_1$-$C_7$alkoxy, hydroxyl, $C_2$-$C_8$alkanoyloxy, trifluoromethyl and nitro; or a pharmaceutically acceptable salt thereof.

5. A Compound according to claim 1 of the formula I in which —$A_1$—$A_2$—, —$A_3$—$A_4$—, —$A_5$—$A_6$— have the indicated meanings; X represents >$C(R_6)$— or >N—, and $R_6$ is hydrogen; alk denotes $C_1$-$C_7$alkylene, $C_3$-$C_7$alkenylene or $C_3$-$C_7$alkynylene, where the multiple bonds are located in a position higher than α to the piperazine nitrogen; $R_1$, $R_2$ and $R_3$, independently of one another, denote $C_2$-$C_8$alkanoyl, $C_1$-$C_4$alkoxycarbonyl, $C_1$-$C_4$alkanesulfonyl or benzenesulfonyl; and $R_3'$ and $R_7$ denote hydrogen, $R_4$ denotes hydrogen, $C_3$-$C_7$-cycloalkyl, phenyl, biphenylyl or naphthyl; $R_5$ is acetyl; where the aromatic radicals in each case are unsubstituted or substituted one, two or three times by substituents selected from the group consisting of halogen, $C_1$-$C_4$alkyl, $C_1$-$C_4$alkoxy, hydroxyl, $C_2$-$C_6$alkanoyloxy, trifluoromethyl and nitro; or a pharmaceutically acceptable salt thereof.

6. A compound according to claim 1 of the formula I in which —$A_1$—$A_2$—, —$A_3$—$A_4$—, —$A_5$—$A_6$— have the indicated meanings; X represents >$C(R_6)$— or >N—, and $R_6$ is hydrogen; alk denotes $C_1$-$C_7$alkylene; $R_1$ denotes $C_2$-$C_8$alkanoyl; $R_2$ denotes $C_2$-$C_8$alkanoyl, benzoyl, $C_1$-$C_4$alkanesulfonyl or benzenesulfonyl, $C_1$-$C_4$alkyl or phenyl-$C_1$-$C_4$alkyl, $R_3$ and $R_3'$ together represent a bond, or $R_3$ denotes hydrogen, $C_2$-$C_8$alkanoyl, benzoyl, $C_1$-$C_4$alkanesulfonyl or benzenesulfonyl, and $R_3'$ is hydrogen; $R_4$ denotes hydrogen, $C_3$-$C_7$cycloalkyl, phenyl, biphenylyl or naphthyl, $R_5$ is acetyl; $R_7$ is hydrogen or $C_1$-$C_4$alkyl; where the aromatic radicals in each case are unsubstituted or substituted one, two or three times by substituents selected from the group consisting of halogen, $C_1$-$C_4$alkyl, $C_1$-$C_4$alkoxy, hydroxyl, $C_2$-$C_6$alkanoyloxy, trifluoromethyl and nitro; or a pharmaceutically acceptable salt thereof.

7. A compound according to claim 1 of the formula I in which —$A_1$—$A_2$—, —$A_3$—$A_4$— and —$A_5$—$A_6$— have the indicated meanings; X represents >$C(R_6)$— or >N—, and $R_6$ is hydrogen; alk denotes $C_1$-$C_4$alkylene, or $C_3$-$C_5$alkenylene where the double bond is located in a position higher than α to the piperazine nitrogen; $R_1$ denotes hydrogen or branched $C_3$-$C_6$alkanoyl; $R_2$ denotes $C_2$-$C_6$alkanoyl, $C_1$-$C_4$alkoxy-carbonyl, $C_1$-$C_4$alkanesulfonyl, or benzenesulfonyl which is optionally substituted by $C_1$-$C_4$alkyl or halogen with atomic number up to and including 35, $R_3$ denotes $C_2$-$C_6$alkanoyl, $C_1$-$C_4$alkoxycarbonyl, $C_1$-$C_4$alkanesulfonyl, or benzenesulfonyl which is optionally substituted by $C_1$-$C_4$alkyl or halogen with atom up to and including 35; $R_3'$ is hydrogen; $R_4$ denotes hydrogen, $C_3$-$C_7$cycloalkyl such as cyclohexyl, optionally $C_1$-$C_4$alkyl-substituted phenyl, biphenylyl or naphthyl, $R_5$ is acetyl; $R_7$ is hydrogen; or a pharmaceutically acceptable salt thereof.

8. A compound according to claim 1 of the formula I in which —$A_1$—$A_2$, —$A_3$—$A_4$— and —$A_5$—$A_6$— have the indicated meanings; X represents >$C(R_6)$— or >N—, and $R_6$ is hydrogen; alk denotes $C_1$-$C_4$alkylene;

$R_1$ denotes hydrogen or branched $C_3$-$C_6$alkanoyl; $R_2$ denotes $C_2$-$C_6$alkanoyl, benzoyl or $C_1$-$C_4$alkyl-sulfonyl, $C_1$-$C_4$alkyl, phenyl-$C_1$-$C_4$alkyl; $R_3$ denotes hydrogen, $C_2$-$C_6$alkanoyl, benzoyl or $C_1$-$C_4$alkanesulfonyl, and $R_3'$ is hydrogen; $R_4$ denotes hydrogen, $C_3$-$C_7$cycloalkyl, phenyl which is optionally substituted by $C_1$-$C_4$alkyl; $R_5$ is acetyl; $R_7$ denotes hydrogen or $C_1$-$C_4$alkyl; or a pharmaceutically acceptable salt thereof.

9. A compound according to claim 1 of the formula I in which the structural elements —$A_1$—$A_2$—, —$A_3$—$A_4$— and —$A_5$—$A_6$— each denote ethylene; X represents >N—; $R_1$ denotes branched $C_3$-$C_6$alkanoyl; $R_2$ denotes $C_2$-$C_5$alkanoyl; $R_3$ denotes $C_2$-$C_5$alkanoyl; $R_3'$ is hydrogen; $R_5$ is acetyl; and, on the one hand, alk denotes $C_1$-$C_4$alkylene, and $R_4$ denotes hydrognen; or, on the other hand, alk is methylene and $R_4$ denotes 2,4,6-trimethylphenyl, and $R_7$ is hydrogen; or a pharmaceutically acceptable salt thereof.

10. A compound according to claim 1 of the formula I in which —$A_1$—$A_2$—, —$A_3$—$A_4$— and —$A_5$—$A_6$— have the indicated meanings; X denotes >N— or >C($R_6$)—, and $R_6$ is hydrogen; $R_1$ denotes or branched $C_3$-$C_6$alkanoyl; $R_2$ denotes $C_2$-$C_6$alkanoyl or $C_1$-$C_4$alkyl; $R_3$ denotes hydrogen or $C_2$-$C_6$alkanoyl, and $R_3'$ is hydrogen; $R_5$ is acetyl; $R_7$ denotes hydrogen or $C_1$-$C_4$alkyl; alk denotes branched $C_3$-$C_5$alkylene and $R_4$ denotes hydrogen; or alk denotes methylene and $R_4$ denotes $C_3$-$C_7$cycloalkyl or phenyl which is optionally substituted by $C_1$-$C_4$alkyl; or a pharmaceutically acceptable salt thereof.

11. A compound according to claim 1 of the formula I in which the structural elements —$A_1$—$A_2$—, —$A_3$—$A_4$— and —$A_5$—$A_6$— each denote ethylene; X represents >N—; $R_1$ denotes branched $C_3$-$C_6$alkanoyl; $R_2$ and $R_3$ each denotes $C_2$-$C_5$alkanoyl, and $R_3'$ is hydrogen; or $R_2$ denotes $C_2$-$C_5$alkanoyl or $C_1$-$C_4$alkyl, $R_3$ denotes hydrogen or $C_2$-$C_5$alkanoyl, and $R_3'$ is hydrogen; or $R_3$ and $R_3'$ together represent a bond; $R_5$ is acetyl; alk-$R_4$ denotes isobutyl, cyclopentylmethyl, cyclohexylmethyl, benzyl, 2,4,6-trimethylbenzyl; $R_7$ is hydrogen or $C_1$-$C_4$alkyl; or a pharmaceutically acceptable salt thereof.

12. A compound according to claim 1 of the formula I in which the structural elements —$A_1$—$A_2$—, —$A_3$—$A_4$— and —$A_5$—$A_6$— each denote ethylene; X represents >N—; $R_1$ denotes branched $C_3$-$C_6$alkanoyl; $R_2$ and $R_3$ each denote $C_2$-$C_5$alkanoyl, and $R_3'$ is hydrogen; or $R_2$ denotes $C_1$-$C_4$alkyl, $R_3$ denotes hydrogen or $C_2$-$C_5$alkanoyl, and $R_3'$ is hydrogen; $R_5$ is acetyl; alk-$R_4$ denotes isobutyl, cyclopentylmethyl, cyclohexylmethyl, benzyl, 2,4,6-trimethylbenzyl; $R_7$ is hydrogen, or $C_1$-$C_4$alkyl; or a pharmaceutically acceptable salt thereof.

13. A compound according to claim 1 of the formula I in which the structural elements —$A_1$—$A_2$—, —$A_3$—$A_4$— and —$A_5$—$A_6$— each have the indicated meanings; X represents >N—, $R_1$ denotes branched $C_3$-$C_6$alkanoyl; $R_2$ and $R_3$ each denote $C_2$-$C_5$alkanoyl and $R_3'$ is hydrogen; or $R_2$ denotes $C_1$-$C_4$alkyl and $R_3$ denotes hydrogen or $C_2$-$C_5$alkanoyl, and $R_3'$ is hydrogen; $R_5$ is acetyl; alk-$R_4$ denotes $C_3$-$C_5$alkyl, $C_3$-$C_6$cycloalkyl-methyl, or benzyl substituted by $C_1$-$C_4$-alkyl; $R_7$ is hydrogen, or $C_1$-$C_4$alkyl; or a pharmaceutically acceptable salt thereof.

14. A compound according to claim 1 of the formula I in which the structural elements —$A_1$—$A_2$—, —$A_3$—$A_4$— and —$A_5$—$A_6$— each denote ethylene; X represents >N—; $R_1$ denotes branched $C_3$-$C_6$alkanoyl; $R_2$ denotes $C_2$-$C_5$alkanoyl; $R_3$ and $R_3'$ together represent a bond; $R_5$ is acetyl; alk-$R_4$ denotes isobutyl, cyclohexylmethyl, benzyl, 2,4,6-trimethylbenzyl, naphthylmethyl or biphenylylmethyl; $R_7$ is hydrogen or $C_1$-$C_4$-alkyl; or a pharmaceutically acceptable salt thereof.

15. A compound according to claim 1 of the formula I in which the structural elements —$A_1$—$A_2$—, —$A_3$—$A_4$— and —$A_5$—$A_6$— each denote the ethylene; X represents >N—; $R_1$ denotes branched $C_3$-$C_6$alkanoyl; $R_2$ denotes $C_2$-$C_5$alkanoyl; $R_3$ and $R_3'$ are each hydrogen; $R_5$ is acetyl; alk-$R_4$ denotes isobutyl, cyclohexylmethyl, benzyl, 2,4,6-trimethylbenzyl, naphthylmethyl or biphenylylmethyl; $R_7$ is hydrogen; or a pharmaceutically acceptable salt thereof.

16. A compound according to claim 1 of the formula I in which the structural elements —$A_1$—$A_2$—, —$A_3$—$A_4$— and —$A_5$—$A_6$— each denote ethylene; X represents >N—; alk denotes $C_1$-$C_4$alkylene; $R_1$ denotes branched $C_3$-$C_5$alkanoyl; $R_2$ denotes $C_2$-$C_5$alkanoyl; $R_3$ and $R_3'$ are each hydrogen; $R_4$ denotes 2,4,6-tri-$C_1$-$C_4$alkylphenyl; $R_5$ denotes acetyl; $R_7$ is hydrogen; or a pharmaceutically acceptable salt thereof.

17. A compound according to claim 1 of the formula I in which the structural elements —$A_1$—$A_2$—, —$A_3$—$A_4$— and —$A_5$—$A_6$— each denote vinylene; X represents >N—; $R_1$ denotes branched $C_3$-$C_5$alkanoyl; $R_2$ is $C_2$-$C_5$alkanoyl or $C_1$-$C_4$alkyl; $R_3$ denotes hydrogen or $C_2$-$C_5$alkanoyl; $R_3'$ is hydrogen; alk-$R_4$ denotes 2,4,6-tri-$C_1$-$C_4$alkylphenyl-$C_1$-$C_4$alkyl; $R_5$ denotes acetyl; $R_7$ is hydrogen, methyl or ethyl; or a pharmaceutically acceptable salt thereof.

18. A compound according to claim 1 of the formula I in which the structural elements —$A_1$—$A_2$—, —$A_3$—$A_4$— and —$A_5$—$A_6$— each denote vinylene; X represents >N—; $R_1$ denotes branched $C_3$-$C_5$alkanoyl; $R_2$ is $C_2$-$C_4$alkanoyl, or $C_1$-$C_4$alkyl; $R_3$ and $R_3'$ together represent a bond; alk-$R_4$ denotes 2,4,6-tri-$C_1$-$C_4$alkylphenyl-$C_1$-$C_4$alkyl; $R_5$ denotes acetyl; $R_7$ is hydrogen, methyl or ethyl; or a pharmaceutically acceptable salt thereof.

19. A compound according to claim 1 of the formula I in which the structural elements —$A_1$—$A_2$—, —$A_3$—$A_4$— and —$A_5$—$A_6$— each denote ethylene; X represents >N—; $R_1$ denotes pivaloyl; $R_2$ is acetyl, propionyl or pivaloyl; $R_3$ denotes acetyl, propionyl or pivaloyl; $R_3'$ is hydrogen; alk-$R_4$ denotes 2,4,6-trimethylphenylmethyl; $R_5$ denotes acetyl; $R_7$ is hydrogen; or a pharmaceutically acceptable salt thereof.

20. A compound according to claim 1 of the formula I in which the structural elements —$A_1$—$A_2$—, —$A_3$—$A_4$— and —$A_5$—$A_6$— each denote ethylene; X represents >N—; $R_1$ denotes pivaloyl; $R_2$ is acetyl; $R_3$ denotes acetyl; $R_3'$ is hydrogen; alk-$R_4$ denotes 2,4,6-trimethylphenylmethyl; $R_5$ denotes acetyl; $R_7$ is hydrogen; or a pharmaceutically acceptable salt thereof.

21. A compound according to claim 1 of the formula I in which the structural elements —$A_1$—$A_2$—, —$A_3$—$A_4$— and —$A_5$—$A_6$— denote ethylene or vinylene, or the elements —$A_1$—$A_2$— and —$A_3$—$A_4$— each denote ethylene and —$A_5$—$A_6$— denotes vinylene; X represents >N—; $R_1$ denotes branched $C_3$-$C_5$alkanoyl; $R_2$ denotes $C_1$-$C_4$alkyl; $R_3$ and $R_3'$ each denote hydrogen; $R_5$ denotes acetyl; $R_7$ is hydrogen; and alk-$R_4$ denotes 2,4,6-trimethylbenzyl; or a pharmaceutically acceptable salt thereof.

22. A compound according to claim 1 of the formula I in which the structural elements —$A_1$—$A_2$—, —A₃—A₄— and —A₅—A₆— each denote vinylene; X represents >N—; R₁ denotes pivaloyl; R₂ denotes methyl or ethyl; R₃ and R₃' each denote hydrogen; R₅ denotes acetyl; R₇ is hydrogen; and alk-R₄ denotes 2,4,6-trimethylbenzyl; or a pharmaceutically acceptable salt thereof.

23. A compound according to claim 1 selected from the group consisting of 16,17,18,19,28,29-hexahydro-4-O-acetyl-8-O-pivaloyl-11-hydroxy-11,15-dideoxo-1-deoxy-1,15-oxy-3-[4-(2,4,6-trimethylbenzyl)-piperazin-1-yl]-rifamycin SV;

16,17,18,19,28,29-hexahydro-4-O,8-O-di-pivaloyl-11-hydroxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-acetyl-8-O-pivaloyl-11-acetyloxy-1-deoxy-11,15-dideoxo-1,15-oxy-3-(4-isobutyl-1-piperazinyl)-rifamycin SV;

16,17,18,19,28,29-hexahydro-4-O-ethoxycarbonyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-benzoyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

4-O-benzoyl-8-O-pivaloyl-11-benzoyloxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-acetyl-8-O-pivaloyl-11-acetyloxy-1-deoxy-11,15-deoxo-1,15-oxy-3-(4-isobutyl-piperazin-1-yl)-rifamycin SV;

16,17,18,19,28,29-hexahydro-4-O-propionyl-8-O-pivaloyl-11-propionyloxy-1-deoxy-11,15-dideoxo-1,15-oxy-3-(4-isobutyl-piperazin-1-yl)-rifamycin SV;

16,17,18,19,28,29-hexahydro-4-O-propionyl-8-O-pivaloyl-11-propionyloxy-1-deoxy-11,15-dideoxo-11,15-oxy-3-(4-cyclohexylmethyl-piperazin-1-yl)-rifamycin SV;

16,17,18,19,28,29-hexahydro-4-O-methanesulfonyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-acetyl-8-O-pivaloyl-11-hydroxy-1-deoxy-11,15-dideoxo-1,15-oxy-3-[2-methyl-4-(2,4,6-trimethylbenzyl)-piperazin-1-yl]-rifamycin SV;

16,17,18,19,28,29-hexahydro-4-O-acetyl-8-O-pivaloyl-11-hydroxy-1-deoxy-11,15-dideoxo-1,15-oxy-3-(4-cyclopentylmethyl-1-piperazinyl)-rifamycin SV;

16,17,18,19,28,29-hexahydro-4-O-acetyl-8-O-pivaloyl-11-hydroxy-1-deoxy-11,15-dideoxo-1,15-oxy-3-[4-(2-cyclopentylethyl)-piperazin-1-yl]-rifamycin SV;

16,17,18,19,28,29-hexahydro-4-O-acetyl-8-O-pivaloyl-11-acetyloxy-1-deoxy-11,15-dideoxo-1,15-oxy-3-(4-neopentyl-piperazin-1-yl)-rifamycin SV;

16,17,18,19,28,29-hexahydro-4-O-acetyl-8-O-pivaloyl-11-acetyloxy-1-deoxy-11,15-dideoxo-1,15-oxy-3-(2-methyl-4-cyclohexylmethyl-piperazin-1-yl)-rifamycin SV;

4-O-methyl-8-O-pivaloyl-1-deoxy-15-deoxo-1,15-oxy-3-[4-(2,4,6-trimethylbenzyl)-piperazin-1-yl]-rifamycin SV;

16,17,18,19-tetrahydro-4-O-methyl-8-O-pivaloyl-1-deoxy-15-deoxo-1,15-oxy-3-[4-(2,4,6-trimethylbenzyl)-piperazin-1-yl]-rifamycin SV;

16,17,18,19,28,29-hexahydro-4-O-methyl-8-O-pivaloyl-11-acetyloxy-1-deoxy-11,15-dideoxo-1,15-oxy-3-[4-(2,4,6-trimethylbenzyl)-piperazin-1-yl]-rifamycin SV;

4-O-ethyl-8-O-pivaloyl-1-deoxy-15-deoxo-1,15-oxy-3-[4-(2,4,6-trimethylbenzyl)-piperazin-1-yl]-rifamycin SV;

4-O-benzyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-ethyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

16,17,18,19,28,29-hexahydro-4-O-benzyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

4-O-methyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

4-O-methyl-8-O-pivaloyl-11-hydroxy-1-deoxy-11,15-dideoxo-1,15-oxy-3-(4-cyclohexylmethyl-piperazin-1-yl)-rifamycin SV;

16,17,18,19,28,29-hexahydro-4-O-methyl-8-O-pivaloyl-11-hydroxy-1-deoxy-11,15-dideoxo-1,15-oxy-3-(4-cyclohexylmethyl-piperazin-1-yl)-rifamycin SV;

4-O-acetyl-8-O-pivaloyl-1-deoxy-15-deoxo-1,15-oxy-3-[4-(2,4,6-trimethylbenzyl)-piperazin-1-yl]-rifamycin SV;

4-O-propionyl-8-O-pivaloyl-1-deoxy-15-deoxo-1,15-oxy-3-[4-(2,4,6-trimethylbenzyl)-piperazin-1-yl]-rifamycin SV;

4-O-acetyl-8-O-pivaloyl-1-deoxy-15-deoxo-1,15-oxy-3-[2-methyl-4-(2,4,6-trimethyl-benzyl)-piperazin-1-yl]-rifamycin SV; and 4-O-acetyl-8-O-pivaloyl-1-deoxy-15-deoxo-1,15-oxy-3-[2-methyl-4-(2,4,6-trimethylbenzyl)-piperazin-1-yl]-rifamycin SV; and pharmaceutically acceptable salts thereof.

24. A compound according to claim 1 selected from the group consisting of
16,17,18,19,28,29-Hexahydro-4-O-propionyl-8-O-pivaloyl-11-hydroxy-1-deoxy11,15-dideoxo-1,15-oxy-3-[4-(2,4,6-trimethylbenzyl)-piperazin-1-yl]-rifamycin SV;

16,17,18,19-Tetrahydro-4-O-pivaloyl-11-acetyloxy-1-deoxy-11,15-dideoxo-1,15-oxy-3-[4-(2,4,6-trimethylbenzyl)-piperazin-1-yl]-rifamycin SV;

16,17,18,19,28,29-Hexahydro-4-O-acetyl-8-O-pivaloyl-11-acetyloxy-1-deoxy-11,15-dideoxo-1,15-oxy-3-[4-(2,4,6-trimethylbenzyl)-piperazin-1-yl]-rifamycin SV;

16,17,18,19,28,29-Hexahydro-4-O-acetyl-8-O-pivaloyl-11-acetyloxy-1-deoxy-11,15-dideoxo-1,15-oxy-3-(4-cyclohexylmethyl-piperazin-1-yl)-rifamycin SV; and 16,17,18,19,28,29-Hexahydro-4-O-acetyl-8-O-pivaloyl-11-hydroxy-1-deoxy-11,15-dideoxo-1,15-oxy-3-[2-methyl-4-(2,4,6-trimethylbenzyl)-piperazin-1-yl]-rifamycin SV;

and pharmaceutically acceptable salts thereof.

25. A compound according to claim 1 selected from the group consisting of
4-O-Methyl-8-O-pivaloyl-1-deoxy-15-deoxo-1,15-oxy-3-[4-(2,4,6-trimethylbenzyl)-piperazin-1-yl]-rifamycin SV;

16,17,18,19-Tetrahydro-4-O-methyl-8-O-pivaloyl-1-deoxy-11,15-dideoxo-1,15-oxy-11-hydroxy-3-[4-(2,4,6-trimethylbenzyl)-piperazin-1-yl]-rifamycin SV;

4-O-Ethyl-11-hydroxy-3-(4-neopentyl-piperazin-1-yl)-8-O-pivaloyl-1-deoxy-11,15-dideoxo-1,15-oxy-rifamycin SV;

3-(4-Cyclohexylmethylpiperidin-1-yl)-11-hydroxy-4-O-methyl-8-O-pivaloyl-1-deoxy-11,15-dideoxo-1,15-oxy-rifamycin SV;

11-Hydroxy-4-O-methyl-8-O-pivaloyl-1-deoxy-11,15-dideoxo-1,15-oxy-3-(4-cyclohexylmethylpiperazin-1-yl)-rifamycin SV;

4-O-Methyl-8-O-pivaloyl-11-hydroxy-1-deoxy-11,15-dideoxo-1,15-oxy-3-[4-(2,4,6-trimethylbenzyl)-piperazin-1-yl]-rifamycin SV;

8-O-Dimethylcarbamyl-1-deoxy-15-deoxo-1,15-oxy-3-[4-(2,4,6-trimethylbenzyl)-piperazin-1-yl]-4-O-methyl-rifamycin SV;

8-O-Dimethylcarbamyl-1-deoxy-11,15-dideoxo-1,15-oxy-3-[4-(2,4,6-trimethylbenzyl)-piperazin-1-yl]-11-hydroxy-4-O-methyl-rifamycin SV; and 8-O-[1-(2-Methoxy-2,2-dimethylacetyl)]-1-deoxy-11,15-dideoxo-1,15-oxy-3-[4-(2,4,6-trimethylbenzyl)-piperazin-1-yl]-11-hydroxy-4-O-methyl-rifamycin SV;

and pharmaceutically acceptable salts thereof.

26. 16,17,18,19,28,29-Hexahydro-4-O-acetyl-8-O-pivaloyl-11-acetyloxy-1-deoxy-11,15-dideoxo-1,15-oxy-3-[4-(2,4,6-trimethylbenzyl)-piperazine-1-yl]-rifamycin SV or a pharmaceutically acceptable salt thereof, according to claim 1.

27. 4-O-Ethyl-11-hydroxy-3-(4-neopentyl-piperazin-1-yl)-8-O-pivaloyl-1-deoxy-11,15-dideoxo-1,15-oxy-rifamycin SV or a pharmaceutically acceptable salt thereof, according to claim 1.

28. 4-O-Methyl-8-O-pivaloyl-11-hydroxy-1-deoxy-11,15-dideoxo-1,15-oxy-3-[4-(2,4,6-trimethylbenzyl)-piperazin-1-yl]-rifamycin SV or a pharmaceutically acceptable salt thereof, according to claim 1.

29. 8-O-Dimethylcarbamyl-1-deoxy-11,15-dideoxo-1,15-oxy-3-[4-(2,4,6-trimethylbenzyl)-piperazin-1-yl]-11-hydroxy-4-O-methyl-rifamycin SV or a pharmaceutically acceptable salt thereof, according to claim 1.

30. A compound according to claim 1 of the formula I in which the structural elements $-A_1-A_2-$, $-A_3-A_4-$ and $-A_5-A_6-$ each have the indicated meanings; X represents $>N-$; $R_1$ denotes pivaloyl, 2-methoxy-2,2-dimethylacetyl or aminocarbonyl disubstituted by $C_1-C_3$-alkyl; $R_2$ denotes $C_2-C_5$-alkanoyl or $C_1-C_4$-alkyl; $R_3$ denotes hydrogen or $C_2-C_5$-alkanoyl; $R_3'$ represents hydrogen; or $R_3$ and $R_3'$ together represent a common bond; alk-$R_4$ denotes $C_3-C_5$-alkyl, $C_3-C_6$-cycloalkylmethyl, or benzyl 2,4,6-trisubstituted by $C_1-C_4$-alkyl; or a pharmaceutically acceptable salt thereof.

31. A compound according to claim 1 of the formula I in which the structural elements $-A_1-A_2-$, $-A_3-A_4-$ and $-A_5-A_6-$ each have the indicated meanings; X represents $>N-$; $R_1$ denotes pivaloyl, 2-methoxy-2,2-dimethylacetyl or dimethylaminocarbonyl; $R_2$ denotes $C_1-C_4$-alkyl; $R_3$ and $R_3'$ each denote hydrogen; or $R_3$ and $R_3'$ together represent a common bond; $R_5$ denotes acetyl; $R_7$ denotes hydrogen; and alk-$R_4$ denotes 2,4,6-trimethylbenzyl, neopentyl or cyclohexylmethyl; or a pharmaceutically acceptable salt thereof.

32. A pharmaceutical composition for the treatment of hyperlipidemia comprising a compound according to claim 1 or a pharmaceutically acceptable salt thereof with suitable auxiliaries and additives.

33. A method for the treatment of hyperlipidaemia, characterized in that a therapeutically effective amount of a compound according to claim 1 or a pharmaceutically acceptable salt thereof is administered to a mammal in need thereof.

* * * * *